(12) United States Patent
Watanabe et al.

(10) Patent No.: US 8,299,255 B2
(45) Date of Patent: Oct. 30, 2012

(54) 3,8-DIAMINOTETRAHYDROQUINOLINE DERIVATIVE

(75) Inventors: Takeshi Watanabe, Tokyo (JP); Masaru Terauchi, Tokyo (JP); Masaaki Nagasawa, Tokyo (JP); Kouichirou Tanaka, Tokyo (JP); Masataka Washiduka, Tokyo (JP)

(73) Assignee: Zeria Pharmaceutical Co., Ltd., Tokyo (JP)

( * ) Notice: Subject to any disclaimer, the term of this patent is extended or adjusted under 35 U.S.C. 154(b) by 18 days.

(21) Appl. No.: 12/866,843

(22) PCT Filed: Feb. 6, 2009

(86) PCT No.: PCT/JP2009/000487
§ 371 (c)(1),
(2), (4) Date: Aug. 9, 2010

(87) PCT Pub. No.: WO2009/098901
PCT Pub. Date: Aug. 13, 2009

(65) Prior Publication Data
US 2010/0317693 A1  Dec. 16, 2010

(30) Foreign Application Priority Data

Feb. 8, 2008 (JP) .................. 2008-029781
Oct. 28, 2008 (JP) .................. 2008-277044

(51) Int. Cl.
*C07D 409/14* (2006.01)
(52) U.S. Cl. ...................................................... 546/158
(58) Field of Classification Search .................. None
See application file for complete search history.

(56) References Cited

U.S. PATENT DOCUMENTS

| | | | |
|---|---|---|---|
| 5,206,235 | A | 4/1993 | Fisher et al. |
| 5,310,737 | A | 5/1994 | Fisher et al. |
| 6,864,250 | B1 | 3/2005 | Funamizu et al. |
| 2001/0041720 | A1 | 11/2001 | Ankersen |

FOREIGN PATENT DOCUMENTS

| | | |
|---|---|---|
| JP | 6 172316 | 6/1994 |
| JP | 8 814 | 1/1996 |
| JP | 2001 513565 | 9/2001 |
| JP | 2003 527338 | 9/2003 |
| WO | 2008 116107 | 9/2008 |

OTHER PUBLICATIONS

Li et al., Tetrahydroisoquinoline 1-carboxamides as growth hormone secretagogues, 15 Bioorg. & Med. Chem. Letts., 1799-1802 (2005).*
Zaragoza Dorwald, Side Reactions in Organic Synthesis; A Guide to Successful Synthesis Design, Wiley-VCH, Weinheim, Preface, p. IX (2005).*

Rosauer, G. Keith et al., "Novel 3,4-Dihydroquinolin-2(1H)-ONE Inhibitors of Human Glycogen Phosphorylase a," Bioorganic & Medicinal Chemistry Letters, vol. 13, pp. 4385-4388, (2003).
Bowers, C.V. et al., "Structure-Activity Relationships of a Synthetic Pentapeptide that Specifically Releases Growth Hormone in Vitro", The Endocrine Society, vol. 106, No. 3, pp. 663-667, (1980).
Bowers, C.Y. et al., "On the in Vitro and in Vivo Activity of a New Synthetic Hexapeptide that Acts on the Pituitary to Specifically Release Growth Hormone", The Endocrine Society, vol. 114, No. 5, pp. 1537-1545, (1984).
Patchett, A.A. et al., "Design and biological activities of L-163, 191 (MK-0677): A potent, orally active growth hormone secretagogue", Proc., Natl., Acad., Sci., vol. 92, pp. 7001-7005, (Jul. 1995).
Howard, D. Andrew et al., "A Receptor in Pituitary and Hypothalamus That Functions in Growth Hormone Release", Science, vol. 273, pp. 974-977, (Aug. 16, 1996).
Kojima, Masayasu et al., "Ghrelin is a growth-hormone-releasing acylated peptide from stomach", Nature, vol. 402, pp. 656-660, (Dec. 9, 1999).
Bednarek, A. Maria et al., "Structure-Function Studies on the New Growth Hormone-Releasing Peptide, Ghrelin: Minimal Sequence of Ghrelin Necessary for Activation of Growth Hormone Secretagogue Receptor 1a", Journal of Medicinal Chemistry, vol. 43, No. 23, pp. 4370-4376, (2000).

(Continued)

*Primary Examiner* — Janet Andres
*Assistant Examiner* — Timothy R Rozof
(74) *Attorney, Agent, or Firm* — Oblon, Spivak, McClelland, Maier & Neustadt, L.L.P.

(57) ABSTRACT

To provide a compound which has a potent agonistic activity on GHS-R and which is useful as a therapeutic agent for systemic wasting diseases such as cachexia.
A 3,8-diaminotetrahydroquinoline derivative represented by formula (1a) (wherein X represents $CH_2$, C=O, CH—OR, CH—SR, or CH—NRR'; m is a number of 1 or 2; Ar represents a phenyl group, a naphthyl group, a 5-membered or 6-membered aromatic heterocyclic group having one or two elements selected from S, N, and O, or a similar group; $R^1$ and $R^2$, which may be identical to or different from each other, each represent a hydrogen atom or a methyl group; $R^3$ represents a C1 to C6 alkyl group or a similar group; n is a number of 0 or 1; $R^4$ and $R^5$, which may be identical to or different from each other, each represent a hydrogen atom, or a C1 to C6 alkyl group, etc.; and $R^6$, $R^7$, R, and R', which may be identical to or different from one another, each represent a hydrogen atom or a C1 to C6 alkyl group), or a salt thereof.

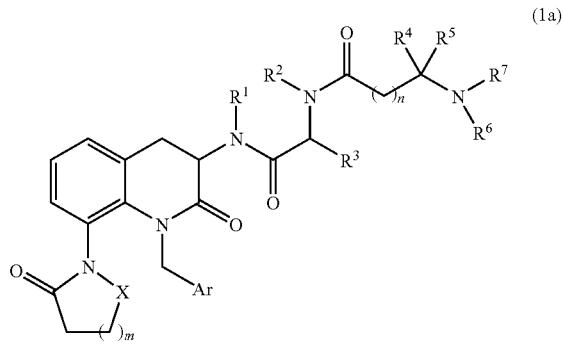

(1a)

12 Claims, No Drawings

OTHER PUBLICATIONS

Date, Yukari et al., "Ghrelin, a Novel Growth Hormone-Releasing Acylated Peptide, Is Synthesized in a Distinct Endocrine Cell Type in the Gastrointestinal Tracts of Rats and Humans", The Endocrine Society, vol. 141, No. 11, pp. 4255-4261, (2000).

Smith, G. Roy et al., "Peptidomimetic Regulation of Growth Hormone Secretion", The Endocrine Society, vol. 18, No. 5, pp. 621-645, (Oct. 1997).

Shuto, Yujin et al., "Generation of polyclonal antiserum against the growth hormone secretagogue receptor (GHS-R) Evidence that the GHS-R exists in the hypothalamus, pituitary and stomach of rats", Life Sciences, vol. 68, pp. 991-996, (2001).

Date, Yukari et al., "Central Effects of a Novel Acylated Peptide, Ghrelin, on Growth Hormone Release in Rats", Biochemical and Biophysical Research Communications, vol. 275, No. 2, pp. 477-480, (2000).

Nakazato, Masamitsu et al., "A role ghrelin in the central regulation of feeding", Nature, vol. 409, pp. 194-198, (Jan. 11, 2001).

Ariyasu, Hiroyuki et al., "Stomach is a Major Source of Circulating Ghrelin, and Feeding State Determines Plasma Ghrelin-Like Immunoreactivity Levels in Humans", The Journal of Clinical Endocrinology & Metabolism, vol. 86, No. 10, pp. 4753-4758, (Oct. 2001).

Date, Yukari et al., "The Role of the Gastric Afferent Vagal Nerve in Ghrelin-Induced Feeding and Growth Hormone Secretion in Rats", Gastroenterology, vol. 123, No. 4, pp. 1120-1128, (Oct. 2002).

Tschoep, Matthias et al "Ghrelin induces adiposity in rodents", Nature, vol. 407, pp. 908-913, (Oct. 2000).

Nagaya, Noritoshi et al., "Hemodynamic, Renal, and Hormonal Effects of Ghrelin Infusion in Patients with Chronic Heart Failure", The Journal of Clinical Endocrinology & Metabolism, vol. 86, No. 12, pp. 5854-5859, (Dec. 2001).

Okumura, Hiroyuki et al., "Vasodilatory Effect of Ghrelin, an Endogenous Peptide From the Stomach", Journal of Cardiovascular Pharmacology, vol. 39, No. 6, pp. 779-783, (2002).

Nagaya, Noritoshi et al., "Chronic Administration of Ghrelin Improves Left Ventricular Dysfunction and Attenuates Development of Cardiac Cachexia in Rats With Heart Failure", Circulation Journal of the American Heart Association, vol. 104, pp. 1430-1435, (Sep. 18, 2001).

Masauda, Yutaka et al., "Ghrelin Stimulates Gastric Acid Secretion and Motility in Rats", Biochemical and Biophysical Research Communications, vol. 276, No. 3, pp. 905-908, (2000).

* cited by examiner

3,8-DIAMINOTETRAHYDROQUINOLINE DERIVATIVE

TECHNICAL FIELD

The present invention relates to a compound which has a potent agonistic activity on a growth hormone secretagogue receptor, and to use of the compound as a drug.

BACKGROUND ART

In the 1970s, a substance that has a weak growth hormone (GH)-releasing activity was found among opiate peptide derivatives (Non-Patent Document 1). Thereafter, more potent peptidyl growth hormone secretagogues (GHSs) were synthesized (Non-Patent Document 2). In the 1990s, a group of nonpeptidyl GHSs which shows GH-releasing activity after oral administration was synthesized (Non-Patent Document 3). GHSs collectively refer to a family of peptidyl and nonpeptidyl compounds having GH-releasing activity. Studies on the action mechanism thereof revealed that GHSs stimulate GH release by binding to a growth hormone secretagogue receptor (GHS-R), which differs from growth hormone-releasing hormone (GHRH) (Non-Patent Document 2).

In 1996, the GHS-R was identified by expression cloning using a nonpeptidyl GHS and found to be a G protein-coupled receptor (GPCR) based on the primary structure. However, GHS-R was an orphan receptor whose endogenous ligand was not identified (Non-Patent Document 4).

In 1999, a search for the endogenous ligand was carried out using a cell line stably expressing the GHS-R by monitoring increase in intracellular $Ca^{2+}$ level. As a result, a substance that exhibits potent GH-releasing activity was isolated from the stomach and designated ghrelin (Non-Patent Document 5). Ghrelin is synthesized as a prepro form composed of 117 amino acid residues and secreted as a peptide composed of 28 amino acid residues after processing. The third serine residue (Ser3) at N-terminus is esterified with octanoic acid (fatty acid), and a peptide derived from the first four amino acids including the esterified serine at N-terminus exhibits physiological activity (Non-Patent Documents 5 and 6).

Ghrelin is predominantly expressed in the stomach and is also expressed in the intestinal tract, pancreas, and hypothalamus (Non-Patent Document 5). At present, GHS-R, which is a ghrelin receptor, is known to have two subtypes (1a, 1b). Subtype 1b lacks a C-terminal portion of 1a and does not actually function, whereas subtype 1a is widely distributed in many organs including the hypothalamus, pituitary, stomach, intestinal tract, heart, lung, pancreas and adipose tissue (Non-Patent Documents 7 to 9).

Ghrelin has multiple physiological functions in addition to GH-releasing activity from the pituitary, such as a potent orexigenic activity, regulation of energy metabolism, protective cardiovascular effects and stimulation of gastric motility and gastric acid secretion.

Ghrelin, which exhibits potent GH-releasing activity (Non-Patent Document 5 and 10), is a useful therapeutic agent for short stature, which is a growth-hormone-deficient disease. In addition, GH is thought to be a hormone that is closely related to aging as well as growth. In fact, a decrease in GH secretion causes loss of muscle and bone mass, resulting in impairment of QOL of the aged. Therefore, the GH-releasing activity of ghrelin is expected to ameliorate the GH-related dysfunctions, suggesting that ghrelin is useful as a prophylactic and therapeutic agent for aging.

Ghrelin is only a humoral factor showing a potent orexigenic activity by oral administration (Non-Patent Document 11). In human, the blood ghrelin level is high during fasting and decreases after a meal. Therefore, ghrelin is thought to be a hormone that initiates food intake (Non-Patent Document 12). Hunger signal has been elucidated to be transmitted to the feeding center via afferent vagal nerves from the stomach (Non-Patent Document 13). The potent orexigenic activity is expected to ameliorate eating disorders such as anorexia nervosa, suggesting that ghrelin is useful as a therapeutic agent therefor.

Subcutaneous daily administrations of ghrelin cause considerable weight gain and increase in the weight of adipose tissue, although food intake remains virtually unchanged (Non-Patent Document 14). Furthermore, subcutaneous administrations of ghrelin at high dose cause increase in respiratory quotient, suggesting increase in fat mass and suppressed utilization of body fat by ghrelin (Non-Patent Document 14). Thus, ghrelin is closely related to regulation of peripheral lipid metabolism and has function in regulating energy metabolism.

As described above, ghrelin shows anabolic effects, orexigenic effects, and regulatory effects on energy metabolism, which are associated with activation of GH-IGF1 (insulin-like growth factor 1) pathway by the GH-releasing activity. Therefore, ghrelin is useful as, for example, a therapeutic agent for cachexia (i.e., systemic wasting diseases involving anorexia, weight loss, muscle mass loss, fat loss, decreased muscle strength, etc.) caused by cancer, aging, serious heart failure, chronic obstructive pulmonary disease (COPD), infection, inflammatory disease, etc.; and a therapeutic agent for ameliorating hyposthenia caused by anorexia during chemotherapy (drug, e.g., anticancer agent) and radiotherapy.

Ghrelin has positive cardiovascular effects (Non-Patent Documents 15 and 16). Intravenous administration of ghrelin in patients with chronic heart failure reduces blood pressure and increases cardiac output without varying cardiac rate, clearly indicating amelioration of cardiac functions. In a post-heart-infarction heart failure model, ghrelin exhibits amelioration of cardiac functions and hypo-nutrition conditions (cachexia). This indicates utility of ghrelin as a therapeutic agent for heart failure (Non-Patent Document 17).

Ghrelin stimulates gastric motility via the vagal nerves (Non-Patent Document 18). This function is expected to provide a therapeutic agent for a disease involving a gastric motility disorder such as postoperative ileus or diabetic gastroparesis.

As described above, ghrelin or a GHS-R agonist is useful as a therapeutic agent for short stature; a therapeutic agent for aging; a therapeutic agent for eating disorder such as anorexia nervosa; a therapeutic agent for cachexia caused by cancer, aging, serious heart failure, chronic obstructive pulmonary disease (COPD), infection, inflammatory disease, etc.; a therapeutic agent for ameliorating anorexia during chemotherapy (drug, e.g., anticancer agent) and radiotherapy; a therapeutic agent for heart failure; and a therapeutic agent for postoperative ileus or diabetic gastroparesis.

From the aforementioned viewpoints, ghrelin or a GHS-R agonist has been investigated (Patent Documents 1 and 2). In fact, anamorelin hydrochloride represented by the following formula is known to be a useful agent for ameliorating cachexia (Patent Document 2).

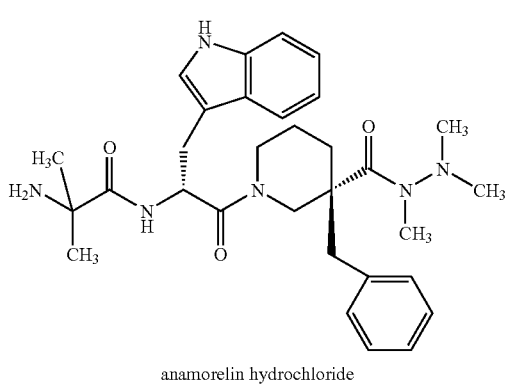

anamorelin hydrochloride

A glucokinase-activating agent which is a compound having a dipeptide structure is reported (Patent Document 3). However, the document does not disclose the compounds of the present invention.

RELATED ART DOCUMENT

[Patent Document 1]
JP-B-1996-814
[Patent Document 2]
JP-A-2003-527338
[Patent Document 3]
WO 2008/116107A2
[Non-Patent Document 1]
Bowers C. Y., et al., Endocrinology 106, 663-667, 1980
[Non-Patent Document 2]
Bowers C. Y., et al., Endocrinology 114, 1537-1545, 1984
[Non-Patent Document 3]
Patchett A. A., et al., Proc. Natl. Acad. Sci. USA 92, 7001-7005, 1995
[Non-Patent Document 4]
Howard A. D., et al., Science 273, 974-977, 1996
[Non-Patent Document 5]
Kojima M., et al., Nature 402, 656-660, 1999
[Non-Patent Document 6]
Bednarek M. A., et al., J. Med. Chem. 43, 4370-4376, 2000
[Non-Patent Document 7]
Date Y., et al., Endocrinology 141, 4255-4261, 2000
[Non-Patent Document 8]
Smith R. G., et al., Endocrine Reviews 18, 621-645, 1997
[Non-Patent Document 9]
Shuto Y., et al., Life Sci. 68, 991-996, 2001
[Non-Patent Document 10]
Date Y., et al., Biochem. Biophys. Res. Commun 275, 477-480, 2000
[Non-Patent Document 11]
Nakazato M., et al., Nature 409, 194-198, 2001
[Non-Patent Document 12]
Ariyasu H., et al., J. Clin. Endocrinol. Metab. 86, 4753-4758, 2001
[Non-Patent Document 13]
Date Y., et al., Gastroenterology 123, 1120-1128, 2002
[Non-Patent Document 14]
Tschop M., et al., Nature 407, 908-913, 2000
[Non-Patent Document 15]
Nagaya N., et al., J. Clin. Endocrinol. Metab. 86, 5854-5859, 2001
[Non-Patent Document 16]
Okumura H., et al., J. Cardiovasc. Pharmacol. 39, 779-783, 2002
[Non-Patent Document 17]
Nagaya N., et al., Circulation 104, 1430-1435, 2001

[Non-Patent Document 18]
Masuda Y., et al., Biochem. Biophys. Res. Commun. 276, 905-908, 2000

DISCLOSURE OF THE INVENTION

Problems to be Solved by the Invention

However, conventional agents for ameliorating cachexia or the like exhibit unsatisfactory agonistic activity on GHS—R, safety, etc., and no effective agent for ameliorating cachexia or the like has been present on the market.

Thus, an object of the present invention is to provide a compound which has a potent agonistic activity on GHS-R and which is useful as a therapeutic agent for systemic wasting diseases such as cachexia.

Means for Solving the Problems

The present inventors have synthesized a variety of compounds having a 3-aminotetrahydroquinoline skeleton and investigated pharmacological activity thereof. As a result, the inventors have found that 3,8-diaminotetrahydroquinoline derivatives represented by the following formula (1) exhibit an agonistic activity on GHS-R 10- to 1,000-fold potent with respect to that exhibited by compounds disclosed in Patent Document 1 and having no amino group at the 8-position of the tetrahydroquinoline skeleton, and have high safety, and therefore are a useful therapeutic agents for systemic wasting diseases. The present invention has been accomplished on the basis of this finding.

Accordingly, the present invention provides a 3,8-diaminotetrahydroquinoline derivative represented by formula (1):

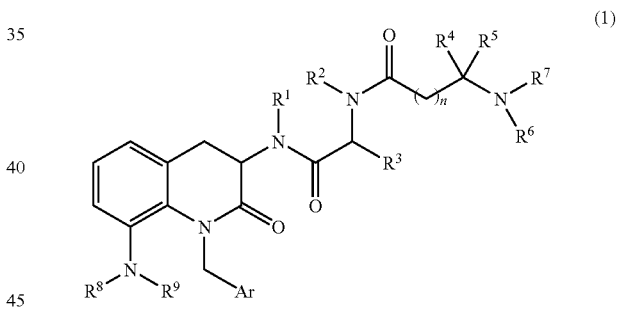

(1)

(wherein $R^8$ and $R^9$, which may be identical to or different from each other, each represent a hydrogen atom, a C1 to C6 alkyl group, a formyl group, or a C2 to C6 alkanoyl group optionally substituted by 1 to 3 halogen atoms; or $R^8$ and $R^9$ may be linked to the adjacent nitrogen atom to form a 5-membered or 6-membered heterocyclic ring having one nitrogen atom;

Ar represents a phenyl group, a naphthyl group, a 5-membered or 6-membered aromatic heterocyclic group having one or two elements selected from S, N, and O, or a condensed aromatic heterocyclic group formed between a benzene ring and a 5-membered or 6-membered heterocyclic ring having one or two elements selected from S, N, and O (wherein the phenyl, naphthyl, or aromatic heterocyclic groups may be substituted by 1 to 3 halogen atoms, a C1 to C6 alkyl group, or a C1 to C6 alkoxy group);

$R^1$ and $R^2$, which may be identical to or different from each other, each represent a hydrogen atom or a methyl group;

$R^3$ represents a C1 to C6 alkyl group (the alkyl group optionally being substituted by a methylthio or benzyloxy group), a phenyl group, a phenyl-$C_{1-4}$ alkyl group, or an indolyl-$C_{1-4}$ alkyl group (the phenyl group or the indolyl group optionally being substituted by a C1 to C6 alkyl group, a halogen atom, a hydroxyl group, or a C1 to C6 alkoxy group);

n is a number of 0 or 1;

$R^4$ and $R^5$, which may be identical to or different from each other, each represent a hydrogen atom, or a C1 to C6 linear, branched, or cyclic alkyl group (the alkyl group optionally being substituted by a halogen atom, a hydroxyl group, a C1 to C6 alkoxy group, a phenyl group, a benzyloxy group, or a hydroxyphenyl group), or $R^4$ or $R^5$, and $R^6$ or $R^7$ may be linked to the adjacent nitrogen atom to form a pyrrolidine ring or a piperidine ring (the pyrrolidine ring or the piperidine ring optionally being substituted by a hydroxyl group); and $R^6$ and $R^7$, which may be identical to or different from each other, each represent a hydrogen atom or a C1 to C6 alkyl group) or a salt thereof.

Among the compounds represented by formula (1), compounds represented by formula (1a):

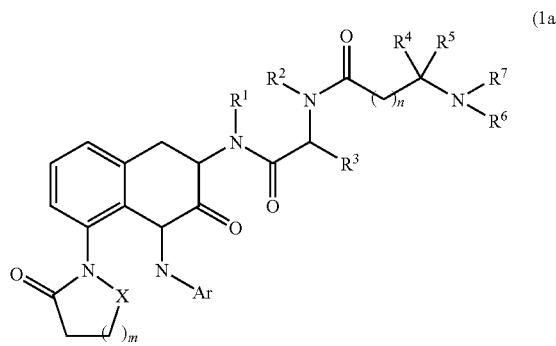

(wherein X represents $CH_2$, C=O, CH—OR, CH—SR, or CH—NRR'; m is a number of 1 or 2; R and R', which may be identical to or different from each other, each represent a hydrogen atom or a C1 to C6 linear, branched, or cyclic alkyl group; and Ar, n and $R^1$ to $R^7$ have the same meanings as defined above) are particularly preferred, since they exhibit a potent agonistic activity on GHS-R and high safety.

The present invention also provides a drug containing the 3,8-diaminotetrahydroquinoline derivative (1) or a salt thereof.

The present invention also provides a pharmaceutical composition comprising the 3,8-diaminotetrahydroquinoline derivative (1) or a salt thereof, and a pharmaceutically acceptable carrier.

The present invention also provides use of the 3,8-diaminotetrahydroquinoline derivative (1) or a salt thereof, for producing a therapeutic agent for a systemic wasting disease.

The present invention also provides a method for treatment of a systemic wasting disease, which comprises administering, to a subject in need thereof, an effective amount of the 3,8-diaminotetrahydroquinoline derivative (1) or a salt thereof.

Effects of the Invention

The compound (1) of the present invention or a salt thereof exhibits a potent agonistic activity on GHS-R and high safety and is useful as, for example, the following agents: a therapeutic agent for short stature; a therapeutic agent for aging; a therapeutic agent for eating disorder such as anorexia nervosa; a therapeutic agent for cachexia caused by cancer, aging, serious heart failure, chronic obstructive pulmonary disease (COPD), infection, inflammatory disease, etc.; a therapeutic agent for ameliorating anorexia during chemotherapy (e.g., anticancer agent) and radiotherapy; a therapeutic agent for heart failure; and a therapeutic agent for postoperative ileus or diabetic gastroparesis.

Modes for Carrying Out the Invention

In formula (1), the C1 to C6 alkyl group represented by $R^8$ or $R^9$ may be linear or branched, and a C1 to C4 alkyl group is preferred. Specific examples include methyl, ethyl, n-propyl, isopropyl, n-butyl, isobutyl, sec-butyl, and tert-butyl. Of these, methyl, ethyl, and isopropyl are particularly preferred. Examples of the C2 to C6 alkanoyl group which may be substituted by 1 to 3 halogen atoms include acetyl, propionyl, butyryl, chloropropionyl, chlorobutyryl, and trifluoroacetyl.

Examples of the 5-membered or 6-membered heterocyclic ring formed through linking of $R^8$ and $R^9$ with the adjacent nitrogen atom include saturated or unsaturated heterocyclic rings having one nitrogen atom. Specific examples include a pyrrolidine ring, a piperidine ring, a pyrrolidinone ring, a succinimide ring, a piperidinone ring, a glutarimide ring, and a pyrrole ring. Of these, saturated heterocyclic rings are preferred.

Examples of more preferred heterocyclic rings include those having the following structure (a):

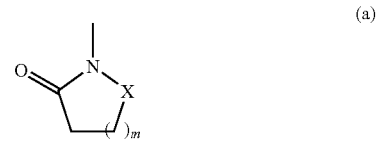

(wherein X and m have the same meanings as defined above).

In the structure (a), m is particularly preferably 1.

Examples of the 5-membered or 6-membered aromatic heterocyclic ring represented by Ar and having one or two elements selected from S, N, and O include thienyl, furyl, thiazolyl, pyrrolyl, pyridyl, imidazolyl, and pyrimidinyl. Examples of the condensed aromatic heterocyclic group formed between a benzene ring and the aforementioned 5-membered or 6-membered heterocyclic ring include benzothienyl, benzofuryl, indolyl, benzothiazolyl, quinazolinyl, quinolyl, isoquinolyl, and benzoimidazolyl.

The phenyl, naphthyl, or aromatic heterocyclic groups represented by Ar may be substituted by 1 to 3 halogen atoms, a C1 to C6 alkyl group, or a C1 to C6 alkoxy group. Examples of the halogen atom include a chlorine atom, a fluorine atom, a bromine atom, and an iodine atom. The C1 to C6 alkyl group may be linear or branched and is more preferably a C1 to C4 alkyl group. Specific examples of the alkyl group include methyl, ethyl, n-propyl, isopropyl, n-butyl, isobutyl, sec-butyl, and tert-butyl. Of these, methyl, ethyl, and n-propyl are particularly preferred. The C1 to C6 alkoxy group may be linear or branched and is more preferably a C1 to C3 alkoxy group. Specific examples of the alkoxy group include methoxy, ethoxy, n-propyloxy, and isopropyloxy. Of these, methoxy is particularly preferred.

Among these groups Ar, phenyl, pyridyl, thienyl, and furyl are more preferred, with phenyl, pyridyl, and thienyl being even more preferred, thienyl being particularly preferred.

Examples of the group represented by $R^1$ or $R^2$ include a hydrogen atom and a methyl group. Of these, a hydrogen atom is particularly preferred.

The C1 to C6 alkyl group represented by $R^3$ may be linear or branched and is preferably a C1 to C4 alkyl group. Specific examples of the alkyl group include methyl, ethyl, n-propyl, isopropyl, n-butyl, isobutyl, sec-butyl, and tert-butyl. Of these, isobutyl is particularly preferred. The alkyl group may be substituted by a methylthio or benzyloxy group.

Examples of the phenyl-$C_{1-4}$ alkyl group represented by $R^3$ include benzyl and phenylethyl. Examples of the indolyl-$C_{1-4}$ alkyl group include indolylmethyl and indolylethyl. The phenyl group, phenyl-$C_{1-4}$ alkyl group, or indolyl-$C_{1-4}$ alkyl group represented by $R^3$ may be substituted by a C1 to C6 alkyl group, a halogen atom, a hydroxyl group, or a C1 to C6 alkoxy group. Examples of the halogen atom include a chlorine atom, a fluorine atom, a bromine atom, and an iodine atom. The C1 to C6 alkyl group may be linear or branched and is preferably a C1 to C4 alkyl group. Specific examples of the alkyl group include methyl, ethyl, n-propyl, isopropyl, n-butyl, isobutyl, sec-butyl, and tert-butyl. Of these, methyl, ethyl, and n-propyl are particularly preferred. The C1 to C6 alkoxy group may be linear or branched and is preferably a C1 to C3 alkoxy group. Specific examples of the alkoxy group include methoxy, ethoxy, n-propyloxy, and isopropyloxy. Of these, methoxy is particularly preferred.

$R^3$ is preferably a C1 to C6 alkyl group, a benzyl group, or an indolylmethyl group (the indolyl group optionally being substituted at the nitrogen atom thereof by a C1 to C6 alkyl group). Of these, isobutyl, benzyl, and indolylmethyl are more preferred, with isobutyl being particularly preferred.

The "n" is a number of 0 or 1, with 0 being particularly preferred.

The C1 to C6 alkyl group represented by $R^4$ or $R^5$ may be linear, branched, or cyclic and is preferably a C1 to C4 alkyl group. Specific examples of the alkyl group include methyl, ethyl, n-propyl, isopropyl, n-butyl, isobutyl, sec-butyl, tert-butyl, and cyclobutyl. Of these, methyl, ethyl, n-propyl, and cyclobutyl are particularly preferred. The alkyl group may be substituted by a halogen atom, a hydroxyl group, a C1 to C6 alkoxy group, a phenyl group, a benzyloxy group, or a hydroxyphenyl group. Examples of the halogen atom include a chlorine atom and a fluorine atom. The alkoxy group may be linear or branched, and examples include methoxy, ethoxy, and isopropyloxy.

$R^4$ or $R^5$ is preferably a hydrogen atom, or a C1 to C6 linear, branched, or cyclic alkyl group. In particular, the cases in which both $R^4$ and $R^5$ are methyl or ethyl, and in which a cyclobutyl group formed from $R^4$ and $R^5$ are preferred.

Regarding $R^3$, $R^4$, and $R^5$, particularly preferred is the case in which $R^3$ is a C4 alkyl group, and each of $R^4$ and $R^5$, which may be identical to or different from each other, is hydrogen atom, a methyl group, or an ethyl group.

$R^4$ or $R^5$, and $R^6$ or $R^7$ may be linked to the adjacent nitrogen atom to form a pyrrolidine ring or a piperidine ring. The pyrrolidine ring or the piperidine ring may be substituted by a hydroxyl group.

The C1 to C6 alkyl group represented by $R^6$ and $R^7$ may be linear or branched and is preferably a C1 to C4 alkyl group. Specific examples of the alkyl group include methyl, ethyl, n-propyl, isopropyl, n-butyl, isobutyl, sec-butyl, and tert-butyl. Of these, methyl, ethyl, and n-propyl are particularly preferred.

Particularly preferably, each of $R^6$ and $R^7$ is a hydrogen atom.

The C1 to C6 alkyl group represented by R or R' may be linear, branched, or cyclic and is preferably a C1 to C4 alkyl group. Specific examples of the alkyl group include methyl, ethyl, n-propyl, isopropyl, n-butyl, isobutyl, sec-butyl, tert-butyl, and cyclobutyl. Of these, methyl, ethyl, n-propyl, and cyclobutyl are particularly preferred. Particularly preferably, each of R and R' is a hydrogen atom.

Particularly preferably, X is $CH_2$, $C=O$, or $CH-OH$.

No particular limitation is imposed on the salt of the compound (1) of the present invention, so long as the salt is a pharmaceutically acceptable salt. Examples of the salt include inorganic acid salts such as hydrochlorides, sulfates, nitrates, and phosphates; and organic acid salts such as acetates, succinates, lactates, tartrates, maleates, fumarates, mandelates, and methanesulfonates.

The compound (1) of the present invention or a salt thereof also encompasses a hydrate and a solvate thereof. Since the compound (1) of the present invention has one or a plurality of asymmetric carbon atoms, some specific compounds each have a plurality of chiral centers. The compound of the present invention encompasses corresponding optical isomers, diastereomers, and isomers attributed to steric hindrance. In the present invention, steric hindrance and other factors should be taken into consideration in some cases.

The compound (1) of the present invention or a salt thereof may be produced through, for example, the following reaction scheme:

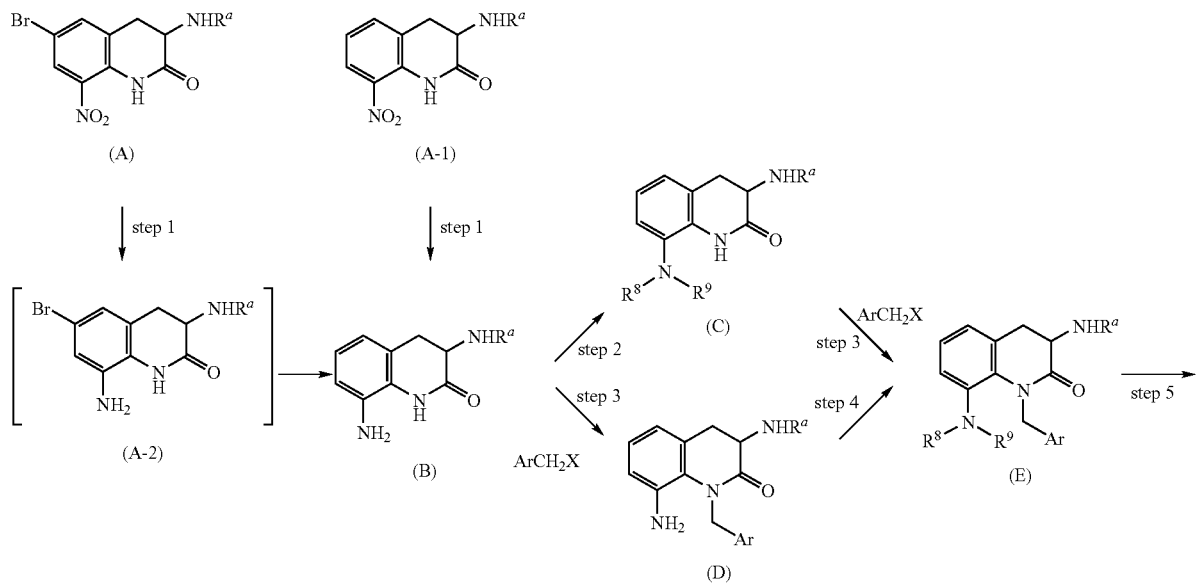

-continued

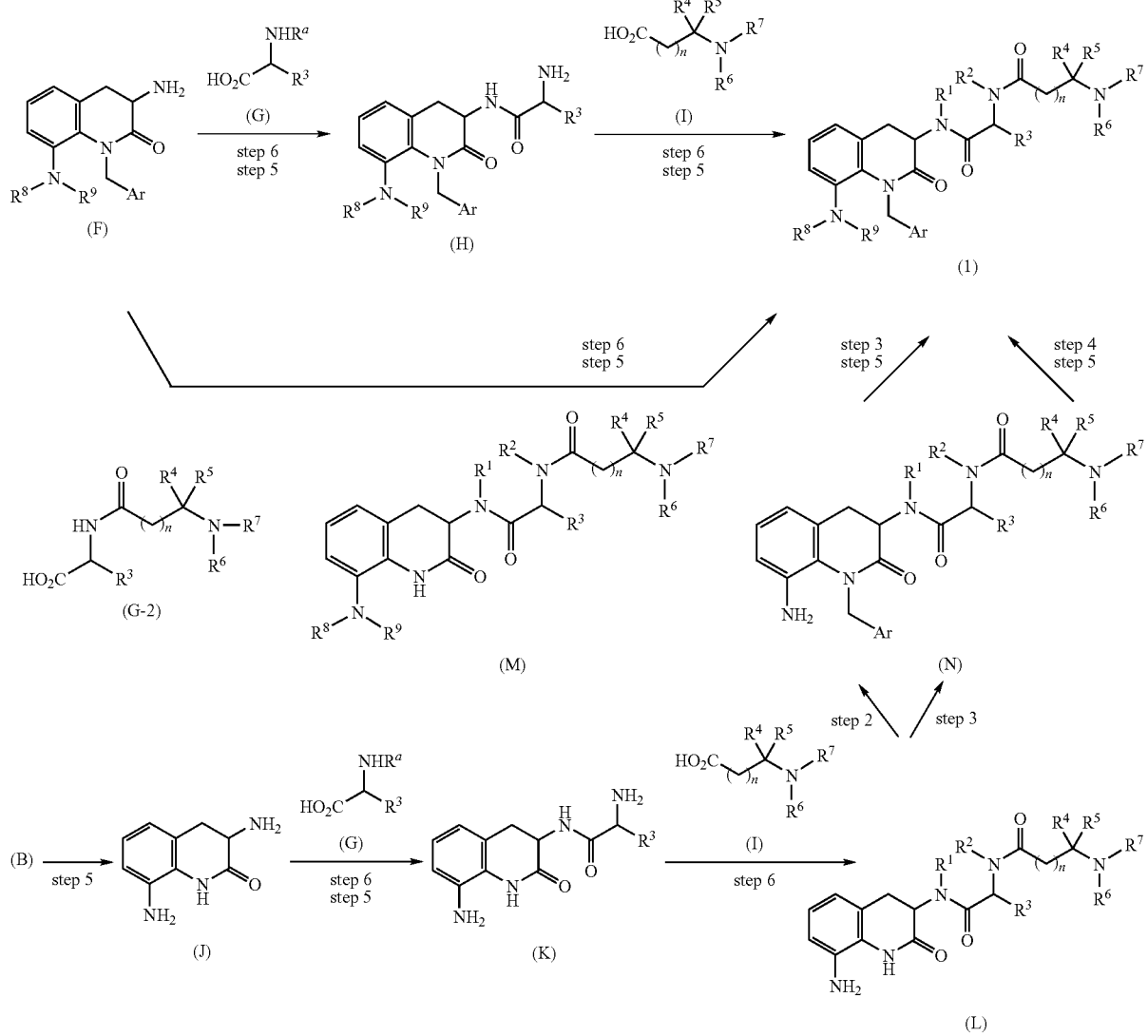

(wherein $R^a$ represents an amino-group-protective group, and $R^1$ to $R^9$, n, and Ar have the same meanings as defined above).

Each reaction step will next be described.

Step 1

Through reduction of Compound (A) or Compound (A-1), Compound (B) is yielded. Generally, the protective group $R^a$ is, for example, a tert-butoxycarbonyl group, an acetyl group, or a benzyloxycarbonyl group. Reduction is preferably catalytic reduction in the presence of a catalyst such as palladium, platinum, or nickel. For example, in a preferred manner, hydrogenation is performed in the presence of a catalyst such as Pd—C, Pt—C, platinum oxide, or Raney nickel. In a more preferred manner, hydrogen gas or ammonium formate is used as a hydrogen source in the presence of Pd—C.

Alternatively, through reduction of Compound (A) in the presence of a metal catalyst such as iron, tin, or zinc, Compound (A-2) is yielded. Through catalytic reduction of Compound (A-2) in the presence of a catalyst such as palladium, platinum, or nickel, Compound (B) is yielded.

Step 2

Through incorporation of substituents $R^8$ and $R^9$ into the 8-position amino group of Compound (B), Compound (C) is yielded. When $R^8$ and $R^9$ each are an alkanoyl group or the like, general amidation may be employed.

Through the same procedure, Compound (M) is yielded by use of Compound (L).

Hereinafter, the case in which $R^8$ and $R^9$ form a heterocyclic ring; e.g., a pyrrolidinone ring or a pyrrolidinedione ring, will be described.

Through reaction of Compound (B) or (L) with 4-halogenobutyryl chloride or succinic anhydride, a 4-halogenobutanoyl group or a 3-hydroxycarbonylpropanoyl group is incorporated into the 8-position amino group of Compound (B) or (L). Subsequently, through cyclization via intramolecular alkylation or amido-bond formation, Compound (C) or (M), in which —N($R^8$)$R^9$ is a pyrrolidin-2-one-1-yl group or a pyrrolidine-2,5-dione-1-yl group, can be yielded. Further, the compound in which —N($R^8$)$R^9$ is a pyrrolidin-2-one-1-yl group is oxidized, to thereby yield a compound in which —N($R^8$)$R^9$ is a pyrrolidine-2-hydroxy-5-one-1-yl group.

Step 3

Through reaction of Compound (B) with a reagent such as ArCH$_2$ halide, ArCH$_2$ methanesulfonate, or ArCH$_2$ p-toluenesulfonate, Compound (D) is yielded. Preferably, this reaction is performed in the presence of a base such as an alkali metal hydroxide, an alkali metal hydride, or an alkali metal carbonate. Alternatively, Compound (D) is yielded from Compound (B) and ArCH$_2$OH through Mitsunobu reaction.

In a similar manner, Compound (E) is yielded by use of Compound (C); Compound (N) is yielded by use of Compound (L); and the compound (1) of the present invention which may have a protected or unprotected amino group is yielded by use of Compound (M).

Step 4

Through incorporation of substituents R$^8$ and R$^9$ into the 8-position amino group of Compound (D), Compound (E) is yielded. When R$^8$ and R$^9$ each are an alkyl group or the like, monoalkylation or dialkylation can be performed through conventional reductive amination.

Hereinafter, the case in which R$^8$ and R$^9$ are alkyl groups or an alkyl group and an alkanoyl group will be described.

Through reaction of Compound (D) with alkylaldehyde and a reducing agent (e.g., sodium cyanoborohydride or sodium triacetoxyborohydride), a mono- or di-alkyl group can be incorporated into the 8-position amino group of Compound (D). Subsequently, into the compound in which the monoalkyl group has been incorporated, an alkanoyl group can be incorporated into the compound through conventional amidation.

In a similar manner, the compound (1) of the present invention which may have a protected or unprotected amino group is yielded by use of Compound (N).

Step 5

Through removal of the amino-group-protective group of Compound (E) via conventional deprotection reaction, Compound (F) is yielded. Preferably, Compound (F) is subjected to optical resolution in advance.

In a similar manner, Compound (H) is yielded by use of Compound (H) which has a protected amino group; the compound (1) of the present invention is yielded by use the compound (1) which has a protected amino group; Compound (J) is yielded by use of Compound (B); and Compound (K) is yielded by use of Compound (K) which has a protected amino group.

Step 6

Through condensation of Compound (F) with an amino acid (G), Compound (H) in which an amino group is protected is yielded. In formula (G), le represent a conventional protective group for amino group, and examples of the protective group include a carbamate-type protective group (e.g., tert-butoxycarbonyl or benzyloxycarbonyl). Condensation reaction between Compound (F) and an amino acid (G) is preferably performed through a reaction by use of a conventional coupling agent or through amino acid condensation reaction based on the mixed anhydride method. When Compound (F) is a salt with a dicarboxylic acid such as tartaric acid, preferably, a base (e.g., alkali metal hydroxide) is added to Compound (F) in an equimolar amount to the amount of Compound (F), and an aqueous solution prepared therefrom is used in the condensation reaction.

In a similar manner, through condensation of Compound (J) with an amino acid (G), Compound (K) in which an amino group is protected is yielded. Also in a similar manner, through condensation of Compound (F) with an amino acid (G-2) (wherein one or two of R$^6$ and R$^7$ may be an amino-group-protective group), the compound (1) of the present invention which may have a protected or unprotected amino group is yielded.

Through condensation of Compound (H) with an amino acid (I) (wherein one or two of R$^6$ and R$^7$ may be an amino-group-protective group), the compound (1) of the present invention which may have a protected or unprotected amino group is yielded.

In a similar manner, through condensation of Compound (K) with an amino acid (I), Compound (L) in which an amino group is protected is yielded.

The compound (1) of the present invention or a salt thereof produced through the aforementioned reactions may be purified through crystallization, recrystallization, washing, chromatographic techniques, or other purification means.

Compound (A) and Compound (A-1), serving as starting materials in the aforementioned reaction scheme, may be produced through the following reaction scheme:

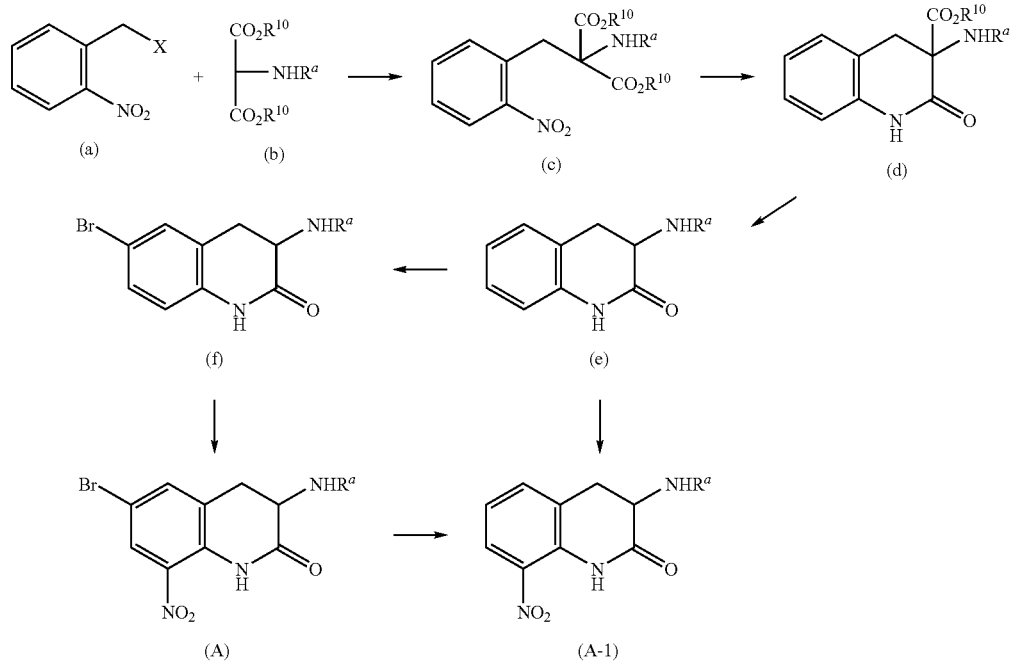

(wherein X represents a halogen atom, $R^{10}$ represents an alkyl group or an aralkyl group; and $R^a$ has the same meaning as defined above).

Specifically, Compound (a) is reacted with Compound (b) in the presence of a base, to thereby yield Compound (c). The nitro group of the thus-produced Compound (c) is reduced, and cyclization is performed, to thereby yield Compound (d). Compound (d) is reacted with an alkali, to thereby yield Compound (e). Compound (e) is nitrated to thereby produce Compound (A-1). Alternatively, Compound (e) is brominated and nitrated, to thereby produce Compound (A). Through catalytic reduction of Compound (A), Compound (A-1) is yielded.

The reaction steps from Compound (a) to Compound (e) are preferably performed sequentially without isolating intermediates. The sequential reaction steps can be performed by use of a common solvent and by adding a reagent after confirmation of completion of each reaction step. The sequential reaction steps are simply performed, since no particular post-treatment is needed except filtration of the used catalyst after conversion of Compound (c) to Compound (d). The solvent is preferably a non-protic polar solvent such as dimethylacetamide, dimethylformamide, N-methylpyrrolidone, or dimethyl sulfoxide, with dimethylacetamide being particularly preferred.

The halogen atom (X) in Compound (a) is preferably a bromine atom or a chlorine atom. The alkyl or aralky group ($R^{10}$) is preferably a C1 to C6 alkyl group such as methyl, ethyl, or propyl, or a benzyl group. Examples of the protective group ($R^a$) include a t-butoxycarbonyl group, an acetyl group, and a benzyloxycarbonyl group. Of these, an acetyl group is preferred.

The reaction between Compound (a) and Compound (b) is preferably performed in the presence of a base and in a non-protic polar solvent. The base employed is preferably an alkali metal alkoxide, an alkali metal halide, an alkali metal carbonate, etc., with sodium ethoxide and potassium ethoxide being particularly preferred. Reduction of Compound (c) is preferably performed through hydrogenation in the presence of a catalyst such as Pd/C, Pt/C, platinum oxide, Raney nickel, etc. In the reaction for yielding Compound (e) from Compound (d), preferably, heating is performed at 70 to 80° C. in the presence of an alkali such as an alkali metal hydroxide.

Through the sequential reaction steps from Compound (a) to Compound (e), a high yield of 90% or higher is attained, which is very advantageous from an industrial aspect.

Nitration of Compound (e) may be performed through reaction with acetyl nitrate, which is prepared from fuming nitric acid and acetic anhydride. Bromination of Compound (e) may be performed through reaction with bromine in the presence of a base. Nitration of Compound (f) may be performed through a conventional reaction with nitric acid and sulfuric acid.

In the aforementioned reaction scheme, Compounds (C), (D), (E), (F), (H), (J), (K), (L), (M), and (N) (Compounds (H), (K), (L), (M), and (N) including amino-group-protected compounds thereof) or salts thereof are useful intermediates for producing the compound (1) of the present invention.

Among these intermediates, the following Compounds (F1) and (H1):

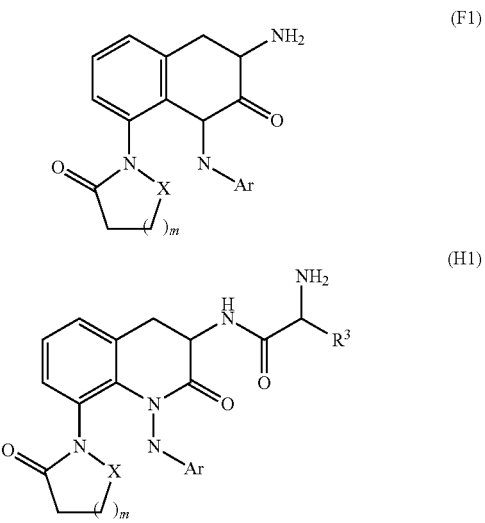

(wherein Ar, X, $R^3$, and m have the same meanings as defined above) are particularly useful intermediates.

As shown in the Examples hereinafter, the compound (1) of the present invention or a salt thereof has a potent agonistic activity on GHS-R. In addition, by virtue of high peroral absorbability, the compound (1) of the present invention can be administered perorally. The compound (1) of the present invention is highly safe, since it exhibits less central transport and a weak inhibitory effect on metabolic enzymes in the liver. Thus, the compound (1) of the present invention or a salt thereof exhibits an agonistic activity on GHS-R and safety higher than those of conventional compounds and is useful as, for example, the following agents: a therapeutic agent for short stature; a therapeutic agent for aging; a therapeutic agent for eating disorder such as anorexia nervosa; a therapeutic agent for cachexia caused by cancer, aging, serious heart failure, chronic obstructive pulmonary disease (COPD), infection, inflammatory disease, etc.; a therapeutic agent for ameliorating anorexia during chemotherapy (drug, e.g., anti-cancer agent) and radiotherapy; a therapeutic agent for heart failure; a therapeutic agent for postoperative ileus or diabetic gastroparesis; and a therapeutic agent for functional dyspepsia.

In particular, the compound (1) of the present invention or a salt thereof is useful as a therapeutic agent for cachexia caused by cancer, aging, infection, and inflammatory disease; and a therapeutic agent for ameliorating anorexia during chemotherapy (e.g., anticancer agent) and radiotherapy.

To the drug of the present invention, a pharmaceutically acceptable carrier or auxiliary agent may be added, and the mixture may be administered to a subject in need thereof perorally or parenterally. For peroral administration, solid preparation such as tablets, granules, powders, and capsules may be provided. Such solid preparations may be combined with appropriate additives such as excipients such as lactose, mannit, cornstarch, and crystalline cellulose; binders such as cellulose derivatives, gum arabic, and gelatin; disintegrants such as calcium carboxymethyl cellulose and crospovidone; and lubricants such as talc and magnesium stearate.

These solid preparations may be coated with a coating base such as hydroxymethyl cellulose phthalate, hydroxypropyl-methyl cellulose acetate succinate, cellulose acetate phthalate, or a methacrylate copolymer, to thereby provide release-controlled preparations. Alternatively, the drug of the invention may be formed into liquid preparations such as liquid, suspension, and emulsion.

For parenteral administration, an injection may be provided. The injection may be combined with, for example, water, ethanol, glycerin, or a conventional surfactant. The drug of the invention may be formed into suppositories by use of an appropriate base.

The dose of the drug of the present invention (as compound (1)) is appropriately determined for individual patients in accordance with the administration route, preparation form, the condition, age, sex, etc. of the patients, etc. Generally, the daily peroral dose for one adult is 10 to 1000 mg, preferably 30 to 600 mg.

EXAMPLES

The present invention will next be described in detail by way of examples, which should not be construed as limiting the invention thereto.

Example 1

Synthesis of N-(2-oxo-1,2,3,4-tetrahydroquinolin-3-yl)acetamide

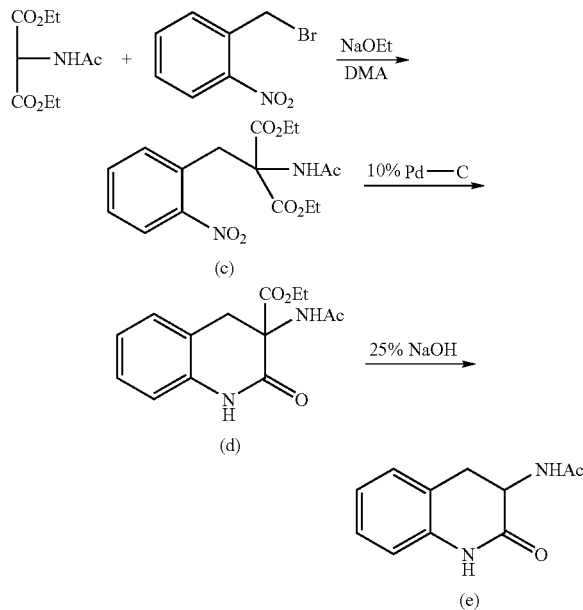

Under a stream of argon, N,N-dimethylacetamide (2.0 L) was added to a mixture of diethyl acetamidomalonate (553 g) and 2-nitrobenzyl bromide (500 g) while the mixture was cooled on ice. 21% NaOEt-ethanol solution (749.97 g) was added dropwise to the mixture over 30 minutes while the inside temperature was maintained at 10 to 22° C. After completion of dropwise addition, the resultant mixture was stirred for one hour while the inside temperature was maintained at 20 to 25° C. (formation of Compound c). The thus-obtained reaction mixture was divided into two equiamount portions, and each portion was subjected to the following procedure.

Specifically, 10% Pd—C (26.1 g) was added to the portion, and hydrogen displacement was performed five times. While maintained at an inside temperature of 60 to 85° C., the mixture was vigorously stirred for five hours (formation of Compound d). The reaction mixture was cooled to 30° C. and filtered with Celite. The filtrate was washed with N,N-dimethylacetamide (250 mL). To the washed liquid, water (3,750 mL) and 25% sodium hydroxide (221.1 g) were added at room temperature, and the mixture was heated at an inside temperature of 74° C. for two hours under stirring (formation of Compound e). Stirring was further performed for one hour at an inside temperature of 10° C. or lower, and the precipitates were recovered through filtration (two batches were combined upon filtration). The recovered precipitates were washed with water (250 mL×2), whereby the title compound (405.9 g) was yielded as a powdery compound.

Compound c: Ms(FAB)m/z353(M+H)$^+$
$^1$H-NMR(400 MHz, DMSO-d$_6$):
δ(ppm)1.15(6H, t, J=7.0 Hz), 1.86(3H, s), 3.83(2H, s), 4.04-4.17(4H, m), 7.23(1H, dd, J=1.0, 8.0 Hz), 7.48-7.55(1H, m), 7.61-7.68(1H, m), 7.88(1H, dd, J=1.5, 8.0 Hz), 8.16(1H, m).

Compound d: Ms(FAB)m/z277(M+H)$^+$
$^1$H-NMR(400 MHz, DMSO-d$_6$):
δ(ppm)0.94(3H, t, J=7.0 Hz) 1.86(3H, s), 3.33(1H, d, J=16.0 Hz)3.41(1H, d, J=16.0 Hz), 3.59-4.01(2H, m), 6.86 (1H, d, J=8.0 Hz), 6.89-6.95(1H, m), 7.11-7.18(2H, m), 8.34 (1H, s), 10.54(1H, s).

Compound e: Ms(FAB)m/z205(M+H)$^+$
$^1$H-NMR(400 MHz, DMSO-d$_6$):
δ(ppm)1.91(3H, s), 2.85(1H, t, J=14.5 Hz), 3.02(1H, dd, J=6.5, 15.5 Hz), 4.40-4.49(1H, m), 6.87(1H, d, J=8.0 Hz), 6.91-6.97(1H, m), 7.13-7.22(2H, m), 8.20(1H, d, J=8.0 Hz), 10.33(1H, s).

Example 2

Synthesis of N-(6-bromo-2-oxo-1,2,3,4-tetrahydroquinolin-3-yl)acetamide

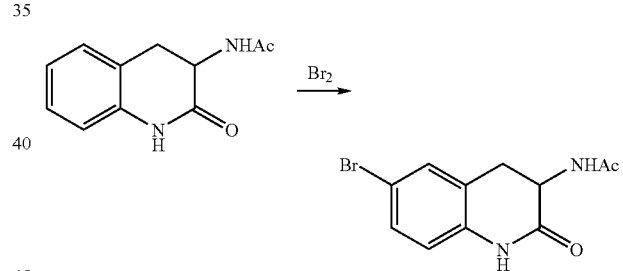

Acetic acid (3,240 mL) was added to N-(2-oxo-1,2,3,4-tetrahydroquinolin-3-yl)acetamide (405.8 g), and the acetamide was dissolved in acetic acid at an inside temperature of 51° C. The reactor was cooled to an inside temperature of 25° C., and sodium acetate was added thereto. To the mixture maintained at an inside temperature of 25° C., bromine was dropwise added over 30 minutes under stirring. The reaction mixture was added to water (35 L), and the reactor was washed with water (3.24 L). The thus-obtained mixture was stirred at 24° C. for one hour.

Separately, the above procedure was repeated, and the obtained two batches were combined. The mixture was filtered, to thereby recover precipitates. The recovered precipitates were sequentially washed with water (405 mL×2) and ethanol (1,500 mL) and then dried in air, whereby the title compound (768.0 g) was yielded.

Ms(FAB)m/z283(M+H)$^+$
$^1$H-NMR(400 MHz, DMSO-d$_6$):
δ(ppm)1.90(3H, s), 2.87(1H, t, J=14.0 Hz), 3.04(1H, dd, J=6.5, 15.5 Hz), 4.40-4.41(1H, m), 6.81(1H, d, J=8.5 Hz), 7.35(1H, dd, J=2.0, 8.5 Hz), 7.42(1H, d, J=2.0 Hz), 8.19(1H, d, J=8.0 Hz), 10.41(1H, s).

Example 3

Synthesis of N-(6-bromo-8-nitro-2-oxo-1,2,3,4-tetrahydroquinolin-3-yl)acetamide

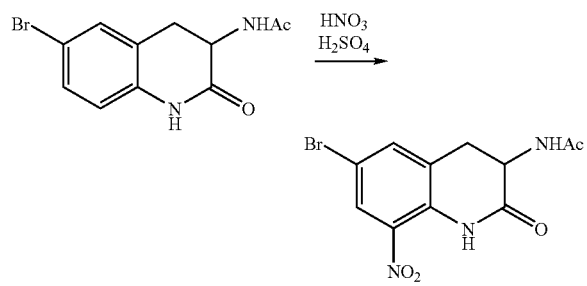

N-(6-Bromo-2-oxo-1,2,3,4-tetrahydroquinolin-3-yl)acetamide (497.0 g) was added to sulfuric acid (4 L) under stirring, while the inside temperature was maintained at 26 to 46° C. (washed with sulfuric acid (500 mL)). Then, while the inside temperature was maintained at 15° C. or lower, 600 nitric acid (193.6 g) was added thereto (washed with sulfuric acid (470 mL)).

Separately, the above procedure was repeated, and the obtained reaction mixtures were sequentially poured to 50% ethanol (15.9 L). The reactor was washed with water (7.95 L), and the mixture was stirred at 20° C. for one hour. The precipitates were recovered through filtration and washed sequentially with water (7.95 L×2) and ethanol (954 mL). The washed product was dried at 60° C. under reduced pressure, whereby the title compound (908.0 g) was yielded.

Ms(FAB)m/z328(M+H)$^+$
$^1$H-NMR(400 MHz, DMSO-d$_6$):
δ(ppm)1.91(3H, s), 3.05(1H, t, J=14.0 Hz), 3.21(1H, dd, J=6.0, 16.0 Hz), 4.58-4.68(1H, m), 7.92(1H, d, J=1.0 Hz), 8.16(1H, d, J=2.0 Hz), 8.33(1H, d, J=8.0 Hz), 10.01(1H, s).

Example 4

Synthesis of 3-amino-6-bromo-8-nitro-3,4-dihydroquinolin-2(1H)-one hydrochloride

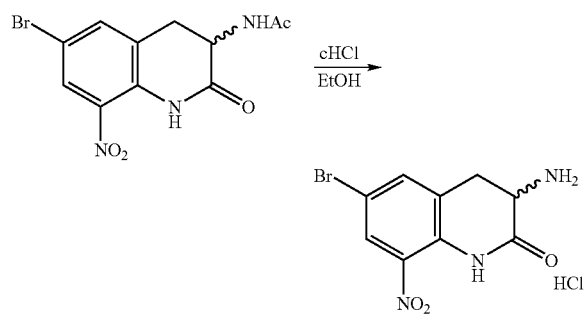

Aqueous hydrochloric acid-ethanol solution was prepared (from commercial aqueous concentrated hydrochloric acid (3 L) and ethanol (6 L)), and N-(6-bromo-8-nitro-2-oxo-1,2,3,4-tetrahydroquinolin-3-yl)acetamide (known compound: Chem. Abst., 4150 (1947)) (604 g) was added to the solution, followed by heating for 14 hours under stirring and reflux. The reaction mixture was cooled on an ice bath, and the precipitates were recovered through filtration. The thus-obtained solid was washed with ethanol and dried, whereby the title compound (571 g) was yielded as a powdery compound.

$^1$H-NMR (400 MHz, DMSO-d$_6$):
δ(ppm)3.25(1H, t, J=15.0 Hz), 3.42(1H, dd, J=6.5, 15.0 Hz), 4.33-4.45(1H, m), 8.04(1H, br s), 8.18(1H, d, J=2.0 Hz), 8.84(3H, br s), 10.45(1H, s).

Example 5

Synthesis of tert-butyl 6-bromo-8-nitro-2-oxo-1,2,3,4-tetrahydroquinolin-3-ylcarbamate

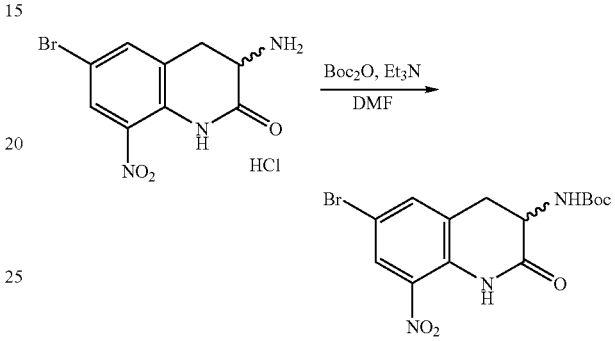

3-Amino-6-bromo-8-nitro-3,4-dihydroquinolin-2(1H)-one hydrochloride (610 g) was added to N,N-dimethylformaldehyde (3 L), and triethylamine (554 mL) was added dropwise to the mixture under cooling on ice. Subsequently, di-tert-butyl carbonate (454 g) was added thereto, and the resultant mixture was stirred at room temperature for 30 minutes. Water (3 L) was added to the reaction mixture, and stirring was performed for 30 minutes under cooling on ice. The precipitates were recovered through filtration and washed sequentially with water and diisopropyl ether. The thus-obtained solid was dried, whereby the title compound (674 g) was yielded as a powdery compound.

MS(FAB)m/z387(M+H)$^+$
$^1$H-NMR(400 MHz, DMSO-d$_6$:
δ(ppm)1.41(9H, s), 3.09(1H, t, J=15.5 Hz), 3.19(1H, dd, J=7.0, 15.5 Hz), 4.29-4.39(1H, m), 7.24(1H, d, J=8.5 Hz), 7.91(1H, br s), 8.14(1H, d, J=2.0 Hz), 9.94(1H, br s).

Example 6

Synthesis of tert-butyl 8-amino-2-oxo-1,2,3,4-tetrahydroquinolin-3-ylcarbamate

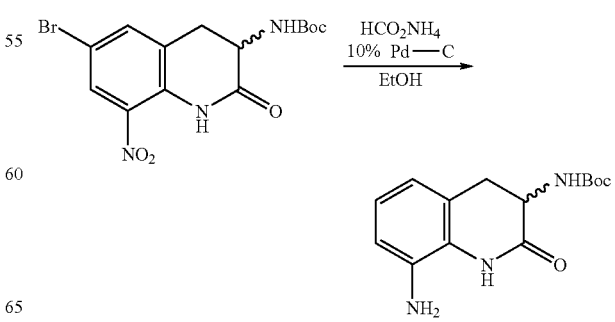

tert-Butyl 6-bromo-8-nitro-2-oxo-1,2,3,4-tetrahydroquinolin-3-ylcarbamate (628 g) was added to ethanol (3.1 L), and the mixture was heated at 65° C. To the mixture, 10% Pd—C (water content: 53%) (67.1 g) and ammonium formate (1.03 kg) were sequentially added, and the resultant mixture was stirred for 10 minutes under heating and reflux. Tetrahydrofuran (2.5 L) was added to the reaction mixture so as to dissolve the precipitates, and undissolved matter was removed through filtration with Celite. The filtrate was concentrated under reduced pressure, and water was added to the residue. The formed precipitates were recovered through filtration. The thus-obtained solid was dried, whereby the title compound (418 g) was yielded as a powdery compound.

MS(FAB)m/z278(M+H)$^+$ $^1$H-NMR(400 MHz, DMSO-$d_6$):

δ(ppm)1.41(9H, s), 2.78-2.92(2H, m), 4.03-4.14(1H, m), 5.05(2H, br s), 6.41(1H, d, J=7.5 Hz), 6.53(1H, d, J=7.5 Hz), 6.69(1H, t, J=7.5 Hz), 6.94(1H, d, J=7.5 Hz), 9.45(1H, br s).

Example 7(a)

Synthesis of tert-butyl 2-oxo-8-(2-oxopyrrolidin-1-yl)-1-(thiophen-3-ylmethyl)-1,2,3,4-tetrahydroquinolin-3-ylcarbamate

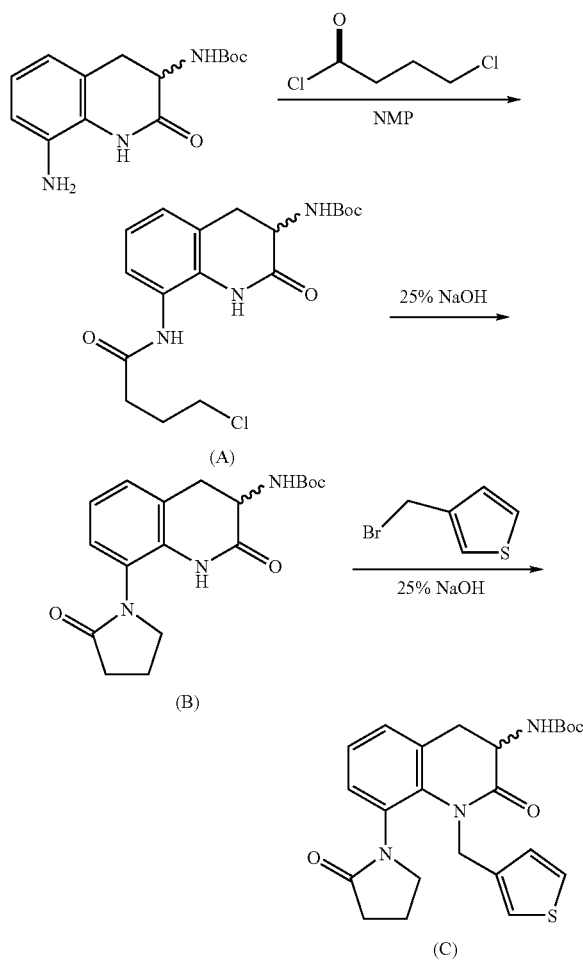

tert-Butyl 8-amino-2-oxo-1,2,3,4-tetrahydroquinolin-3-ylcarbamate (50 g) was dissolved in N-methylpyrrolidinone (250 mL). 4-Chlorobutyryl chloride (22.2 mL) was added dropwise to the solution under cooling with ice, and the mixture was stirred at room temperature for 25 minutes (formation of Compound A). Subsequently, 25% aqueous sodium hydroxide solution (66.2 mL) was added dropwise thereto under cooling with ice, and the mixture was stirred for 25 minutes (formation of Compound B). Then, 25% aqueous sodium hydroxide solution (22.8 mL) and 3-bromomethylthiophene (41.6 g) were sequentially added thereto, and the mixture was stirred at room temperature for one hour. Ethyl acetate and water were added to the reaction mixture for extraction, and the water layer was further subjected to extraction with ethyl acetate. The organic layers were combined, and the combined mixture was dried with sodium sulfate. The solvent was removed under reduced pressure, and diisopropyl ether was added to the residue. The formed precipitates were recovered through filtration and washed with diisopropyl ether-ethyl acetate (10:1). The thus-obtained solid was dried under reduced pressure, whereby the title compound (C) (63.0 g) was yielded.

Alternative Method:

The separately isolated Compound B (50 mg) was dissolved in THF (1.5 mL), and 3-thiophenemethanol (16.5 mg) and triphenylphosphine (38.0 mg) were added to the solution. Under cooling on ice, diethyl azodicarboxylate (ca. 2.2 mol/L toluene solution) (65.9 μL) was added dropwise thereto, and the mixture was stirred at room temperature for 15 hours. Ethyl acetate and water were added to the reaction mixture for extraction, and the water layer was further subjected to extraction with ethyl acetate. The organic layers were combined, and the combined mixture was dried with sodium sulfate. The solvent was removed under reduced pressure, and the residue was purified through silica gel column chromatography (chloroform:methanol=50:1), whereby the title compound (C) (48.2 mg) was yielded.

Compound (A): MS(FAB)m/z382(M+H)$^+$ $^1$H-NMR(400 MHz, DMSO-$d_6$:

δ(ppm)1.41(9H, s), 1.98-2.07(2H, m), 2.46-2.56(2H, m), 2.93-3.02(2H, m), 3.71(2H, t, J=6.5 Hz), 4.07-4.18(1H, m), 6.93(1H, t, J=8.0 Hz), 7.00-7.07(2H, m), 7.31(1H, d, J=8.0 Hz), 9.37(1H, br s), 9.58(1H, br s).

Compound (B): MS(FAB)m/z346(M+H)$^+$ $^1$H-NMR(400 MHz, DMSO-$d_6$):

δ(ppm)1.41(9H, s), 2.08-2.18(2H, m), 2.36-2.43(2H, m), 2.93-3.06(2H, m), 3.56-3.62(2H, m), 4.08-4.19(1H, m), 6.95-7.07(2H, m), 7.10(1H, d, J=7.5 Hz), 7.16(1H, d, J=7.5 Hz), 9.66(1H, s).

Compound (C): MS(FAB)m/z442(M+H)$^+$ $^1$H-NMR(400 MHz, DMSO-$d_6$, 80° C.):

δ(ppm)1.41(9H, s), 1.83-2.07(2H, m), 2.25-2.36(2H, m), 2.79-2.94(2H, m), 3.13-3.40(1H, m), 3.72-3.79(1H, m), 4.08-4.17(1H, m), 4.56(1H, d, J=15.5 Hz), 5.17(1H, d, J=15.5 Hz), 6.52-6.61(1H, m), 6.79(1H, d, J=5.0 Hz), 7.00-7.04(1H, m), 7.06-7.12(1H, m), 7.13-7.18(2H, m), 7.31(1H, dd, J=3.0, 5.0 Hz).

Example 7(b)

Synthesis of tert-butyl 1-benzyl-2-oxo-8-(2-oxopyrrolidin-1-yl)-1,2,3,4-tetrahydroquinolin-3-ylcarbamate

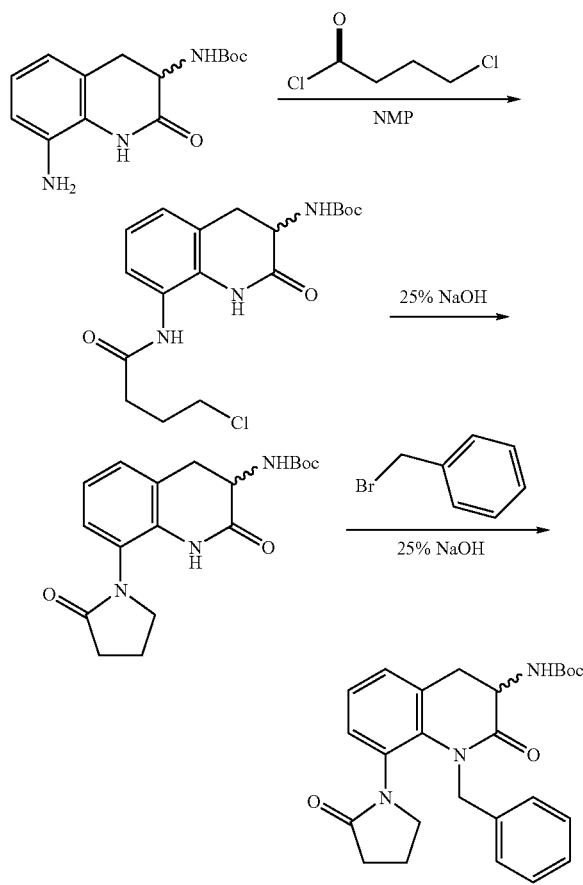

Instead of 3-bromomethylthiophene, benzylbromide (1.48 mL) was used with respect to tert-butyl 2-oxo-8-(2-oxopyrrolidin-1-yl)-1,2,3,4-tetrahydroquinolin-3-ylcarbamate (Compound B) (4.3 g), which had been produced through the same method as employed in Example 7(a), whereby the title compound (5.87 g) was yielded.

MS(FAB)m/z436(M+H)$^+$ $^1$H-NMR(400 MHz, CDCl$_3$):

δ(ppm)1.47(9H, s), 1.71-1.84(1H, m), 2.10-2.42(2H, m), 2.70(1H, t, J=14.5 Hz), 3.19-3.56(3H, m), 4.37-4.46(1H, m), 4.88-5.11(2H, m), 5.82(1H, d, J=4.5 Hz), 7.06-7.30(9H, m).

Example 8

Synthesis of tert-butyl 8-amino-1-benzyl-1,2,3,4-tetrahydro-2-oxoquinolin-3-ylcarbamate

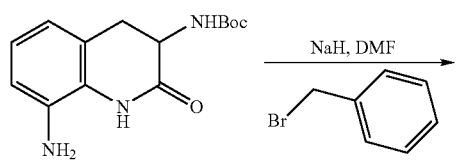

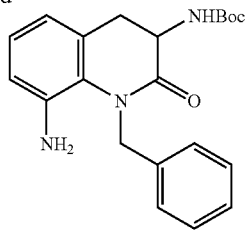

tert-Butyl 8-amino-2-oxo-1,2,3,4-tetrahydroquinolin-3-ylcarbamate produced in Example 6 (10 g) was added to N,N-dimethylformamide (100 mL), and sodium hydride (1.65 g) was added thereto under cooling on ice. The mixture was stirred at room temperature for one hour. Subsequently, under cooling on ice, benzyl bromide (6.48 g) was added to the mixture, and stirring was performed at room temperature for one hour. The reaction mixture was filtered, and the filtrate was concentrated under reduced pressure, to thereby recover a residue. The residue was purified through silica gel column chromatography (ethyl acetate: n-hexane=1:2), whereby the title compound (10.8 g) was yielded.

MS(FAB)m/z368(M+H)$^+$ $^1$H-NMR(400 MHz, CDCl$_3$):

δ(ppm)1.45(9H, s), 2.53(1H, t, J=14.5 Hz), 3.15(1H, dd, J=5.0, 14.5 Hz), 3.50(2H, br s), 4.21-4.33(1H, m), 5.04(1H, d, J=15.0 Hz), 5.17(1H, d, J=15.0 Hz), 5.53-5.84(1H, m), 6.62 (2H, d, J=8.0 Hz), 6.91(1H, t, J=7.5 Hz), 7.17-7.28(5H, m).

Example 9

Synthesis of tert-butyl 1-benzyl-8-ethylamino-1,2,3,4-tetrahydro-2-oxoquinolin-3-ylcarbamate

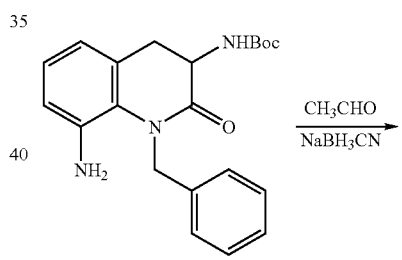

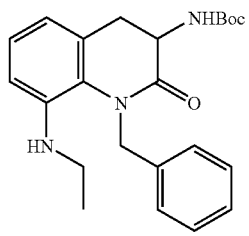

tert-Butyl 8-amino-1-benzyl-1,2,3,4-tetrahydro-2-oxoquinolin-3-ylcarbamate (1.0 g) was dissolved in methanol (10 mL), and acetaldehyde (599 mg), acetic acid (10 mg), and sodium cyanoborohydride (171 mg) were sequentially added to the solution under cooling on ice. The mixture was stirred at room temperature for 30 minutes, and the reaction mixture was concentrated under reduced pressure. The thus-recovered residue was dissolved in ethyl acetate, and the solution was sequentially washed with water, saturated aqueous sodium bicarbonate solution, and saturated aqueous sodium chloride solution. The organic layer was dried over sodium sulfate, and solvent was evaporated under reduced pressure. The recovered residue was purified through silica gel column chromatography (ethyl acetate: n-hexane=1:3), whereby the title compound (600 mg) was yielded.

MS(FAB)m/z396(M+H)+

$^1$H-NMR(400 MHz, CDCl$_3$):
δ(ppm)0.90(3H, t, J=7.0 Hz), 1.45(9H, s), 2.58(1H, t, J=14.5 Hz), 2.88-3.20(4H, m), 4.26-4.36(1H, m), 4.80(1H, d, J=15.0 Hz), 5.21(1H, d, J=15.0 Hz), 5.75-5.86(1H, m), 6.58 (2H, d, J=8.0 Hz), 7.02(1H, t, J=8.0 Hz), 7.16-7.31(5H, m).

Example 10

Synthesis of tert-butyl 1-benzyl-8-(N-ethylacetamido)-2-oxo-1,2,3,4-tetrahydroquinolin-3-ylcarbamate

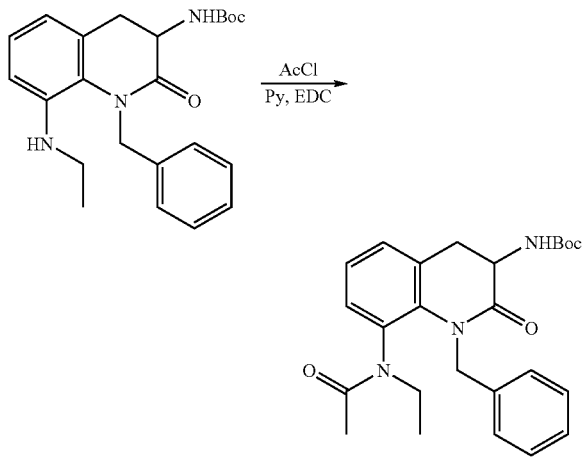

tert-Butyl 1-benzyl-8-ethylamino-1,2,3,4-tetrahydro-2-oxoquinolin-3-ylcarbamate (300 mg) was dissolved in 1,2-dichloroethane (2.5 mL), and pyridine (180 mg) was added to the solution. Under cooling on ice, a solution of acetyl chloride (179 mg) in 1,2-dichloroethane (2.5 mL) was added dropwise to the mixture. The resultant mixture was stirred at room temperature for two hours, and the reaction mixture was concentrated under reduced pressure. Water was added to the thus-recovered residue, and the mixture was subjected to extraction with ethyl acetate. The organic layer was sequentially washed with 0.1N HCl, saturated aqueous sodium bicarbonate solution, and saturated aqueous sodium chloride solution, and dried over sodium sulfate. Solvent was evaporated under reduced pressure, whereby the title compound (330 mg) was yielded.

MS(FAB)m/z438(M+H)+

$^1$H-NMR(400 MHz, CDCl$_3$):
δ(ppm) 0.91-1.00(2.4H, m), 1.34(0.6H, t, J=7.0 Hz), 1.45 (0.9H, s), 1.47(8.1H, s), 1.58(2.1H, s), 1.75(0.9H, s), 2.68-3.15(2H, m), 3.24-3.43(1H, m), 4.10-4.42(2H, m), 4.60-4.70 (0.9H, m), 5.10(0.1H, d, J=16.5 Hz), 5.45(0.1H, d, J=16.5 Hz), 5.72-5.88(1.9H, m), 6.87-7.32(8H, m).

Example 11(a)

Synthesis of 3-amino-8-(2-oxopyrrolidin-1-yl)-1-(thiophen-3-ylmethyl)-3,4-dihydroquinolin-2(1H)-one

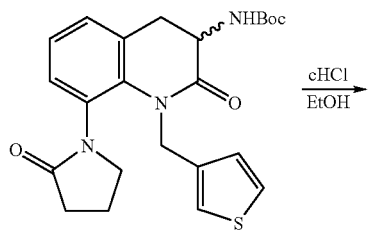

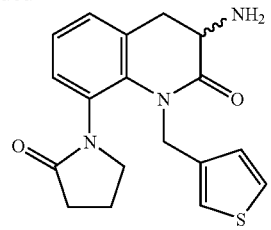

tert-Butyl 2-oxo-8-(2-oxopyrrolidin-1-yl)-1-(thiophen-3-ylmethyl)-1,2,3,4-tetrahydroquinolin-3-ylcarbamate (399 g) was suspended in ethanol (2 L), and concentrated hydrochloric acid (555 mL) was added to the suspension, followed by stirring at 60° C. for 30 minutes. The reaction mixture was neutralized with 25% aqueous sodium hydroxide solution under cooling on ice. The resultant mixture was partitioned between chloroform and water, and the aqueous layer was extracted with chloroform. The organic layers were combined, and the combined organic layer was dried over sodium sulfate. The solvent was evaporated under reduced pressure, whereby the title compound (418 g) in a crude form was yielded, which was employed in the subsequent reaction step without performing further purification.

MS(FAB)m/z342(M+H)+

$^1$H-NMR(400 MHz, DMSO-d$_6$, 80° C.):
δ(ppm)1.78-2.03(4H, m), 2.22-2.39(2H, m), 2.62(1H, t, J=14.5 Hz), 2.86(1H, dd, J=5.0, 14.5 Hz), 3.32-3.39(1H, m), 3.46(1H, dd, J=5.0, 13.0 Hz), 3.62-3.37(1H, m), 4.61(1H, d, J=15.5 Hz), 5.13(1H, d, J=15.5 Hz), 6.75-6.80(1H, m), 6.96-7.14(4H, m), 7.27-7.33(1H, m).

Example 11(b)

Synthesis of 3-amino-1-benzyl-8-(2-oxopyrrolidin-1-yl)-3,4-dihydroquinolin-2(1H)-one

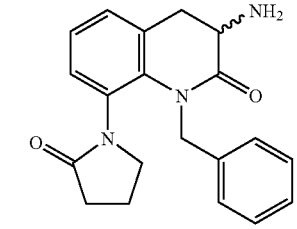

The procedure of Example 11(a) was repeated, except that tert-butyl 1-benzyl-2-oxo-8-(2-oxopyrrolidin-1-yl)-1,2,3,4-tetrahydroquinolin-3-ylcarbamate (5.87 g) was used, whereby the title compound (3.6 g) was yielded.

MS(FAB)m/z336(M+H)+

$^1$H-NMR(400 MHz, DMSO-d$_6$):
δ(ppm)1.60-2.37(6H, m), 2.74(1H, t, J=15.0 Hz), 2.91(1H, dd, J=5.0, 15.0 Hz), 3.10-4.09(3H, m), 4.41-5.25(2H, m), 7.02-7.32(8H, m).

Example 11(c)

Synthesis of N-(3-amino-1-benzyl-1,2,3,4-tetrahydro-2-oxoquinolin-8-yl)-N-ethylacetamide

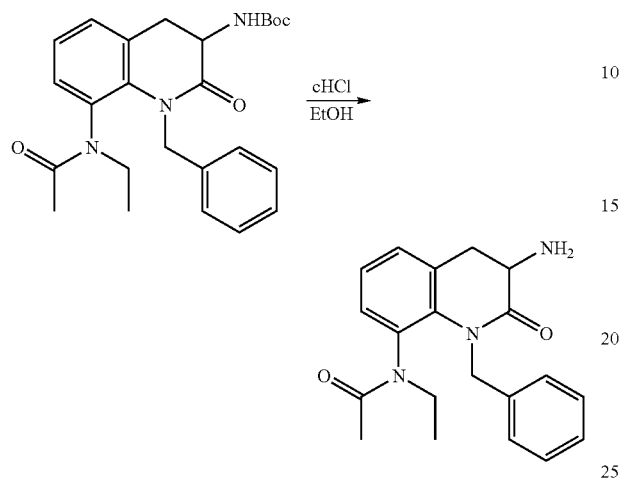

The procedure of Example 11(a) was repeated, except that tert-butyl 1-benzyl-8-(N-ethylacetamido)-2-oxo-1,2,3,4-tetrahydroquinolin-3-ylcarbamate (323 mg) was used, whereby the title compound (240 mg) was yielded.

MS(FAB)m/z338(M+H)$^+$ $^1$H-NMR(400 MHz, CDCl$_3$):

δ(ppm)0.93-1.10(2.4H, m), 1.27(0.6H, t, J=7.0 Hz), 1.50 (2.1H, s), 1.69(0.6; H, s), 1.75(0.3H, s), 1.88(2H, br s), 2.73-3.10(3H, m), 3.49-3.80(2H, m), 4.62(0.9H, d, J=16.0 Hz), 4.87(0.1H, d, J=16.0 Hz), 5.13(0.1; H, d, J=16.0 Hz), 5.34 (0.2H, d, J=16.0 Hz), 5.84(0.7H, d, J=16.0 Hz), 6.84-7.33 (8H, m).

Example 12(a)

Synthesis of 3-amino-8-(2-oxopyrrolidin-1-yl)-1-(thiophen-3-ylmethyl)-3,4-dihydroquinolin-2(1H)-one D-(−)-tartrate

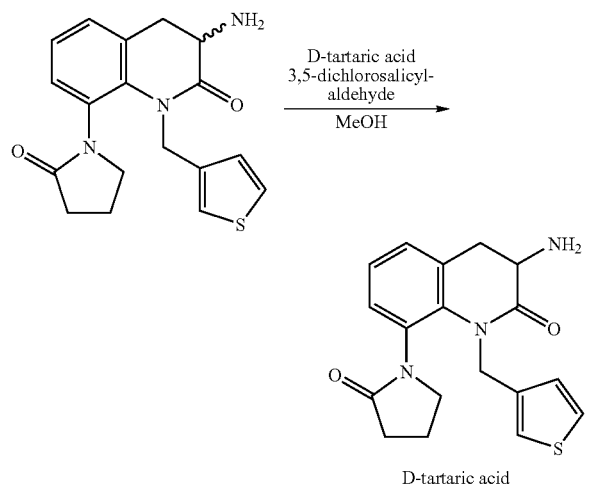

3-Amino-8-(2-oxopyrrolidin-1-yl)-1-(thiophen-3-ylmethyl)-3,4-dihydroquinolin-2(1H)-one (418 g) was dissolved in methanol (3.1 L), and 3,5-dichlorosalicylaldehyde (17.2 g) and D-(−)-tartaric acid (136 g) were added thereto, followed by stirring at 60° C. for 11 hours. The reaction mixture was left to stand to cool, and the formed precipitates were recovered through filtration. The thus-obtained solid was washed with methanol and dried, whereby the title compound (271 g) (97.8% ee) was yielded as a powdery compound.

$^1$H-NMR(400 MHz, DMSO-d$_6$, 80° C.):

δ(ppm)1.79-2.06(2H, m), 2.23-2.40(2H, m), 2.79(1H, t, J=14.5 Hz), 2.95(1H, dd, J=5.0, 14.5 Hz), 3.32-3.39(1H, m), 3.67-3.78(2H, m), 4.05(2H, s), 4.61(1H, d, J=15.5 Hz), 5.16 (1H, d, J=15.5 Hz), 6.80(1H, d, J=5.0 Hz), 7.00-7.04(1H, m), 7.08-7.20(3H, m), 7.33(1H, dd, J=3.0, 5.0 Hz).

Example 12(b)

Synthesis of 3-amino-1-benzyl-8-(2-oxopyrrolidin-1-yl)-3,4-dihydroquinolin-2(1H)-one D-(−)-tartrate

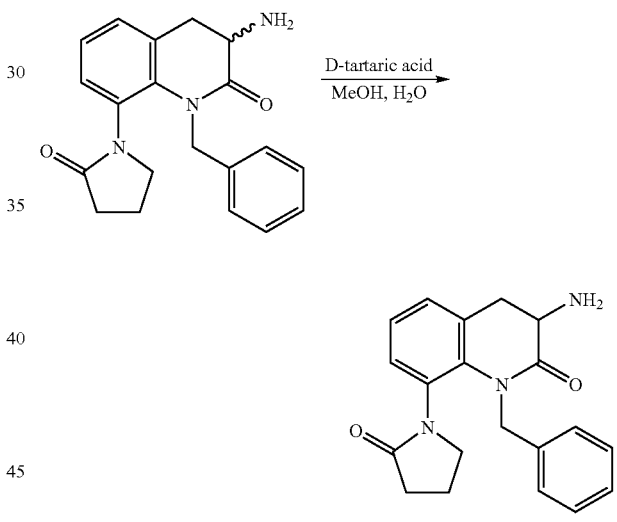

3-Amino-1-benzyl-8-(2-oxopyrrolidin-1-yl)-3,4-dihydroquinolin-2(1H)-one (1.0 g) was dissolved in a mixture of methanol and water (2:1) (20 mL), and D-(−)-tartaric acid (447 mg) was added thereto, followed by stirring at room temperature for two hours. The formed precipitates were recovered through filtration, washed with a mixture of methanol and water (2:1), and dried, whereby the title compound (587 mg) (98.5% ee) was yielded as a powdery compound.

$^1$H-NMR(400 MHz, DMSO-d$_6$, 80° C.):

δ(ppm)1.55-1.73(1H, m), 1.82-1.95(1H, m), 2.11-2.32 (2H, m), 2.83(1H, t, J=14.5 Hz), 2.99(1H, dd, J=5.0, 14.5 Hz), 3.28-3.37(1H, m), 3.60-3.71(1H, m), 3.76(1H, dd, J=5.5, 13.5 Hz), 4.07(2H, s), 4.69(1H, d, J=15.5 Hz), 5.08(1H, d, J=15.5 Hz), 7.01-7.26(8H, m).

Example 13(a)

Synthesis of (−)-3-amino-8-(2-oxopyrrolidin-1-yl)-1-(thiophen-3-ylmethyl)-3,4-dihydroquinolin-2(1H)-one

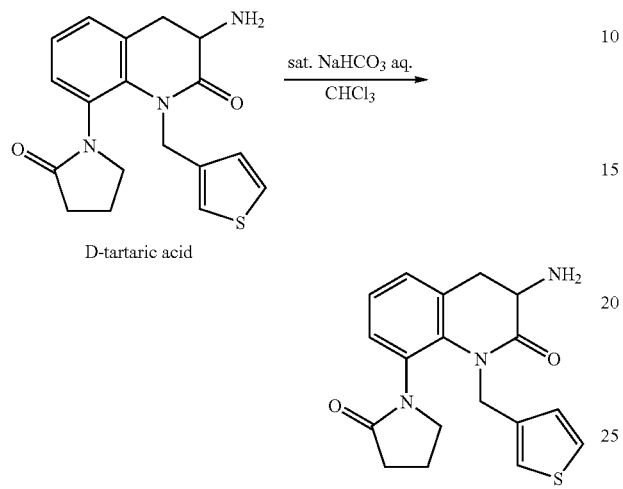

3-Amino-8-(2-oxopyrrolidin-1-yl)-1-(thiophen-3-ylmethyl)-3,4-dihydroquinolin-2(1H)-one D-(−)-tartrate (254 g) was suspended in chloroform (1.3 L), and the suspension was extracted with saturated aqueous sodium bicarbonate solution (1.3 L). The organic layers were combined, and the combined organic layer was dried over sodium sulfate. The solvent was evaporated, and ethyl acetate was added to the thus-recovered residue. The precipitates were recovered through filtration and dried, whereby the title compound (153 g) was yielded.

$[\alpha]_D^{25}$=−6.1° (c1.0, MeOH)
MS(FAB)m/z342(M+H)$^+$
$^1$H-NMR(400 MHz, DMSO-d$_6$, 80° C.):
δ(ppm)1.78-2.03(4H, m), 2.22-2.39(2H, m), 2.62(1H, t, J=14.5 Hz), 2.86(1H, dd, J=5.0, 14.5 Hz), 3.32-3.39(1H, m), 3.46(1H, dd, J=5.0, 13.0 Hz), 3.62-3.37(1H, m), 4.61(1H, d, J=15.5 Hz), 5.13(1H, d, J=15.5 Hz), 6.75-6.80(1H, m), 6.96-7.14(4H, m), 7.27-7.33(1H, m).

Example 13(b)

Synthesis of (−)-3-amino-1-benzyl-8-(2-oxopyrrolidin-1-yl)-3,4-dihydroquinolin-2(1H)-one

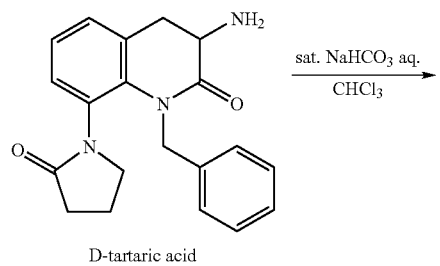

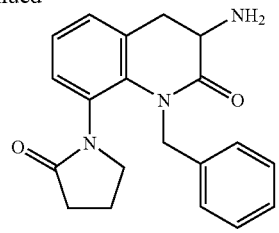

The procedure of Example 10(a) was repeated, except that 3-amino-1-benzyl-8-(2-oxopyrrolidin-1-yl)-3,4-dihydroquinolin-2(1H)-one D-(−)-tartrate (250 mg) was used, whereby the title compound (150 mg) was yielded.

$[\alpha]_D^{25}$=−13.5° (c1.0, MeOH)
MS(FAB)m/z336(M+H)$^+$
$^1$H-NMR(400 MHz, DMSO-d$_6$):
δ(ppm)1.60-2.37(6H, m), 2.74(1H, t, J=15.0 Hz), 2.91(1H, dd, J=5.0, 15.0 Hz), 3.10-4.09(3H, m), 4.41-5.25(2H, m), 7.02-7.32(8H, m).

Referential Example 1(a)

Synthesis of (R)-2-(tert-butoxycarbonylamino)-3-(1-methyl-1H-indol-3-yl) propanoic Acid

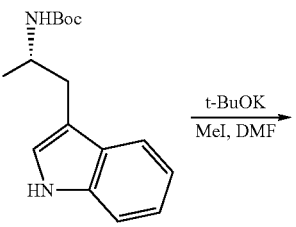

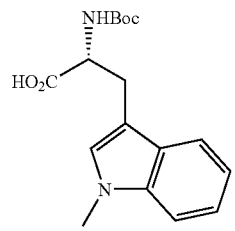

N-tert-Butoxycarbonyl-D-tryptophan (3.0 g) was dissolved in N,N-dimethylformaldehyde (30 mL) under argon, and potassium tert-butoxide (as 12% tetrahydrofuran solution) (17.7 g) was added dropwise thereto under cooling on ice, followed by stirring for 15 minutes. A solution of iodomethane (2.1 g) in N,N-dimethylformaldehyde (3.0 mL) was added to the mixture, and stirring was performed for 10 minutes. The resultant mixture was partitioned between 30% aqueous citric acid solution and ethyl acetate, and the organic layer was sequentially washed with 30% aqueous citric acid solution and saturated aqueous sodium chloride solution, followed by drying over sodium sulfate. The solvent was evaporated under reduced pressure, and diisopropyl ether was added to the thus-recovered residue. The precipitates were recovered through filtration, washed with diisopropyl ether, and dried under reduced pressure, whereby the title compound (1.89 g) was yielded.

MS(FAB)m/z319(M+H)$^+$
$^1$H-NMR(400 MHz, DMSO-d$_6$):
δ(ppm)1.33(9H, s), 2.97(1H, dd, J=9.5, 14.5 Hz), 3.12(1H, dd, J=4.5, 14.5 Hz), 3.72(3H, s), 4.13(1H, dt, J=4.5, 9.5 Hz), 6.99-7.06(2H, m), 7.10-7.17(2H, m), 7.38(1H, d, J=8.0 Hz), 7.54(1H, d, J=8.0 Hz), 12.58(1H, br s).

Referential Example 1(b)

Synthesis of (R)-2-(tert-butoxycarbonylamino)-3-(1-ethyl-1H-indol-3-yl)propanoic Acid

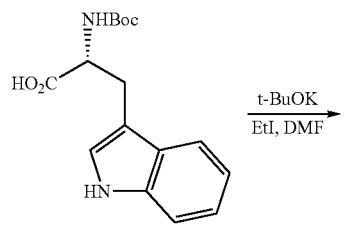

The procedure of Referential Example 1(a) was repeated, except that N-tert-butoxycarbonyl-D-tryptophan (462 mg) and ethyl iodide (184 μL) were used, whereby the title compound (456 mg) was yielded.

MS(FAB)m/z333(M+H)$^+$ $^1$H-NMR(400 MHz, DMSO-d$_6$):
δ(ppm)1.32(3H, t, J=7.0 Hz), 1.33(9H, s), 2.97(1H, dd, J=9.0, 14.5 Hz), 3.12(1H, dd, J=5.0, 14.5 Hz), 4.09-4.20(3H, m), 6.95-7.04(2H, m), 7.08-7.22(2H, m), 7.41(1H, d, J=8.0 Hz), 7.53(1H, d, J=8.0 Hz), 12.50-12.70(1H, br).

Referential Example 1(c)

Synthesis of (R)-2-(tert-butoxycarbonylamino)-3-[1-(2-fluoroethyl)-1H-indol-3-yl]propanoic Acid

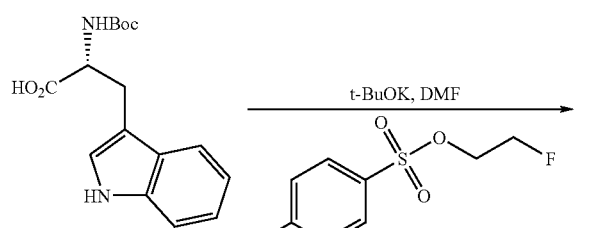

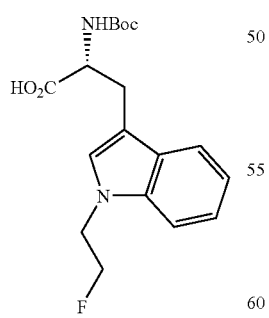

The procedure of Referential Example 1(a) was repeated, except that N-tert-butoxycarbonyl-D-tryptophan (700 mg) and 2-fluoroethyl 4-methylbenzenesulfonate (753 mg) were used, whereby the title compound (538 mg) was yielded.

MS(FAB)m/z351(M+H)$^+$ $^1$H-NMR(400 MHz, DMSO-d$_6$):
δ(ppm)1.33(9H, s), 2.98(1H, dd, J=9.5, 14.5 Hz), 3.13(1H, dd, J=4.5, 14.5 Hz), 4.12-4.20(1H, m), 4.38-4.50(2H, m), 4.62(1H, t, J=4.5 Hz), 4.74(1H, t, J=4.5 Hz), 6.96-7.07(2H, m), 7.10-7.19(2H, m), 7.45(1H, d, J=9.0 Hz), 7.80(1H, d, J=8.0 Hz), 12.57(1H, br s).

Referential Example 1(d)

Synthesis of (R)-2-(tert-butoxycarbonylamino)-3-(1-propyl-1H-indol-3-yl)propanoic Acid

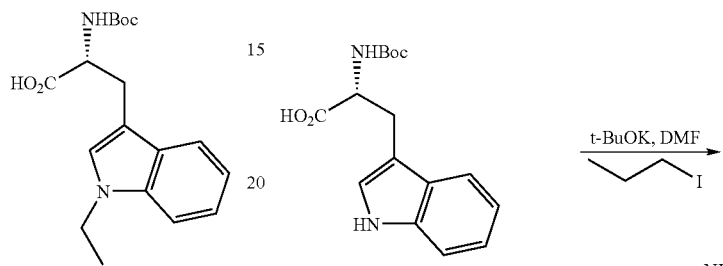

The procedure of Referential Example 1(a) was repeated, except that N-tert-butoxycarbonyl-D-tryptophan (1.0 g) and 1-iodopropane (838 mg) were used, whereby the title compound (1.11 g) was yielded.

MS(FAB)m/z347(M+H)$^+$ $^1$H-NMR(400 MHz, DMSO-d$_6$):
δ(ppm)0.81(3H, t, J=7.5 Hz), 1.32(9H, s), 1.67-1.78(2H, m), 2.97(1H, dd, J=9.5, 14.5 Hz), 3.12(1H, dd, J=5.0, 14.5 Hz), 4.07(2H, t, J=7.0 Hz), 4.11-4.19(1H, m), 6.95-7.04(2H, m), 7.18-7.20(2H, m), 7.41(1H, d, J=8.0 Hz), 7.53(1H, d, J=8.0 Hz), 12.56(1H, br s).

Referential Example 1(e)

Synthesis of (R)-2-(tert-butoxycarbonylamino)-3-(1-isopropyl-1H-indol-3-yl)propanoic Acid

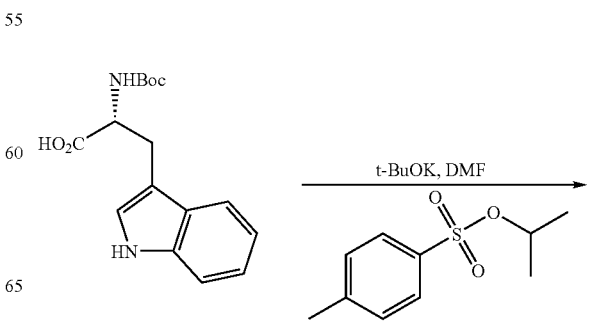

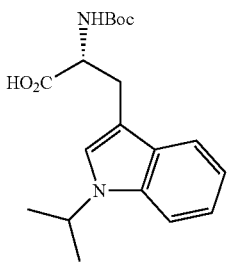

The procedure of Referential Example 1(a) was repeated, except that N-tert-butoxycarbonyl-D-tryptophan (3.0 g) and isopropyl 4-methylbenzenesulfonate (3.17 g) were used, whereby the title compound (1.48 g) was yielded.

MS(FAB)m/z347(M+H)$^+$ $^1$H-NMR(400 MHz, DMSO-d$_6$):

δ(ppm)1.33(9H, s), 1.41(3H, d, J=6.5 Hz), 1.42(3H, d, J=6.5 Hz), 2.97(1H, dd, J=9.5, 14.5 Hz), 3.13(1H, dd, J=4.5, 14.5 Hz), 4.15-4.24(1H, m), 4.63-4.77(1H, m), 6.97-7.05 (2H, m), 7.11(1H, dt, J=1.0, 8.0 Hz), 7.25(1H, s), 7.44(1H, d, J=8.0 Hz), 7.52(1H, d, J=8.0 Hz), 12.57(1H, br s).

Example 14(a)

Synthesis of tert-butyl (2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylcarbamate

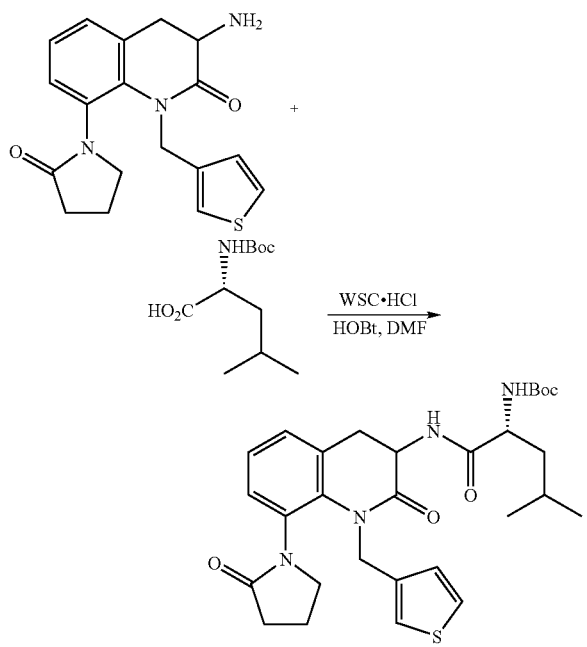

(−)-3-Amino-8-(2-oxopyrrolidin-1-yl)-1-(thiophen-3-ylmethyl)-3,4-dihydroquinolin-2(1H)-one (500 mg) was dissolved in N,N-dimethylformaldehyde (5 mL), and to the solution were sequentially added N-tert-butoxycarbonyl-D-leucine monohydrate (382 mg), 1-hydroxybenzotriazole (207 mg), and 1-ethyl-3-(3-dimethylaminopropyl)carbodiimide hydrochloride (294 mg) under cooling on ice, followed by stirring at room temperature for one hour. The resultant mixture was extracted with ethyl acetate and water, and the organic layer was sequentially washed with saturated aqueous sodium bicarbonate solution and saturated aqueous sodium chloride solution, followed by drying over sodium sulfate. The solvent was evaporated under reduced pressure, and the thus-recovered residue was purified through silica gel column chromatography (chloroform:methanol=50:1), whereby the title compound (832 mg) was yielded.

MS(FAB)m/z555(M+H)$^+$ $^1$H-NMR(400 MHz, DMSO-d$_6$, 80° C.):

δ(ppm)0.87(3H, d, J=5.0 Hz), 0.89(3H, d, J=5.0 Hz), 1.39 (9H, s), 1.49(2H, t, J=7.0 Hz), 1.58-1.70(1H, m), 1.82-2.06 (2H, m), 2.24-2.39(2H, m), 2.74(1H, t, J=14.0 Hz), 2.95-3.05 (1H, m), 3.34-3.43(1H, m), 3.70-3.81(1H, m), 4.00-4.08(1H, m), 4.35-4.44(1H, m), 4.59(1H, d, J=15.5 Hz), 5.17(1H, d, J=15.5 Hz), 6.57(1H, br s), 6.80(1H, dd, J=1.0, 5.0 Hz), 7.02-7.07(1H, m), 7.09-7.14(1H, m), 7.14-7.20(2H, m), 7.32 (1H, dd, J=3.0, 5.0 Hz), 7.76(1H, d, J=6.5 Hz).

Example 14(b)

Synthesis of tert-butyl (2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylcarbamate

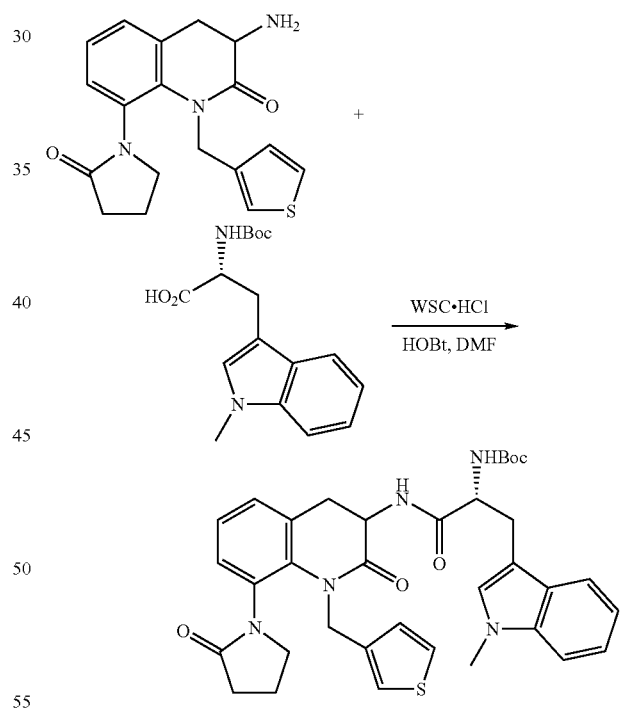

The procedure of Example 14(a) was repeated, except that (−)-3-amino-8-(2-oxopyrrolidin-1-yl)-1-(thiophen-3-ylmethyl)-3,4-dihydroquinolin-2(1H)-one (268 mg) and (R)-2-(tert-butoxycarbonylamino)-3-(1-methyl-1H-indol-3-yl) propanoic acid (284 mg) synthesized in Referential Example 1(a) were used, whereby the title compound (558 mg) was yielded.

MS(FAB)m/z642(M+H)$^+$ $^1$H-NMR(400 MHz, DMSO-d$_6$):

δ(ppm)1.15-1.19(1H, m), 1.32(9H, s), 1.85-2.43(4H, m), 2.60-2.79(2H, m), 2.88-2.99(1H, m), 3.09(1H, dd, J=5.5, 9.0

Hz), 3.30-3.38(1H, m), 3.73(3H, s), 4.19-4.85(3H, m), 4.97-5.24(1H, m), 6.80(1H, d, J=5.0 Hz), 6.94(1H, d, J=8.5 Hz), 7.01(1H, t, J=7.5 Hz), 7.08-7.17(6H, m), 7.34-7.45(2H, m), 7.61(1H, d, J=7.5 Hz), 8.21(1H, d, J=7.5 Hz).

Example 14(c)

Synthesis of tert-butyl (2R)-3-(1-ethyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylcarbamate

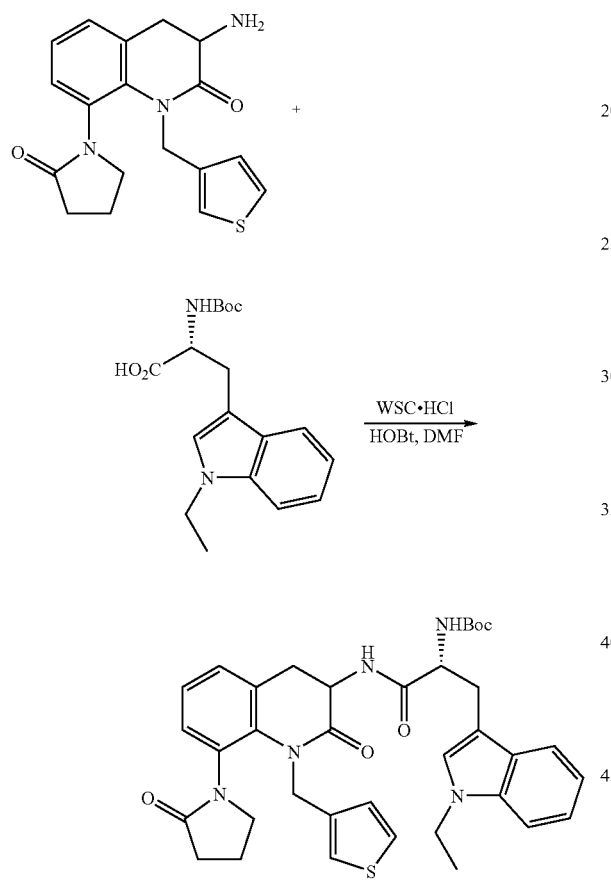

The procedure of Example 14(a) was repeated, except that (−)-3-amino-8-(2-oxopyrrolidin-1-yl)-1-(thiophen-3-ylmethyl)-3,4-dihydroquinolin-2(1H)-one (200 mg) and (R)-2-(tert-butoxycarbonylamino)-3-(1-ethyl-1H-indol-3-yl)propanoic acid (234 mg) synthesized in Referential Example 1(b) were used, whereby the title compound (283 mg) was yielded.

MS(FAB)m/z656(M+H)$^+$ $^1$H-NMR(400 MHz, DMSO-d$_6$):

δ(ppm)1.30-1.38(12H, m), 1.86-2.45(5H, m), 2.58-2.77 (2H, m), 2.93(1H, dd, J=5.5, 9.0 Hz), 3.10(1H, dd, J=5.5, 9.0 Hz), 3.28-3.39(1H, m), 4.14(2H, q, J=7.0 Hz), 4.28-4.79(3H, m), 5.01-5.22(1H, m), 6.79(1H, d, J=5.0 Hz), 6.93(1H, d, J=8.5 Hz), 7.00(1H, t, J=7.5 Hz), 7.05-7.23(6H, m), 7.37-7.43(2H, m), 7.59(1H, d, J=8.0 Hz), 8.17(1H, d, J=7.0 Hz).

Example 14(d)

Synthesis of tert-butyl (2R)-3-[1-(2-fluoroethyl)-1H-indol-3-yl]-1-oxo-1-[2-oxo-8-(2-oxopyrrolidin-1-yl)-1-(thiophen-3-ylmethyl)-1,2,3,4-tetrahydroquinolin-3-ylamino]propan-2-ylcarbamate

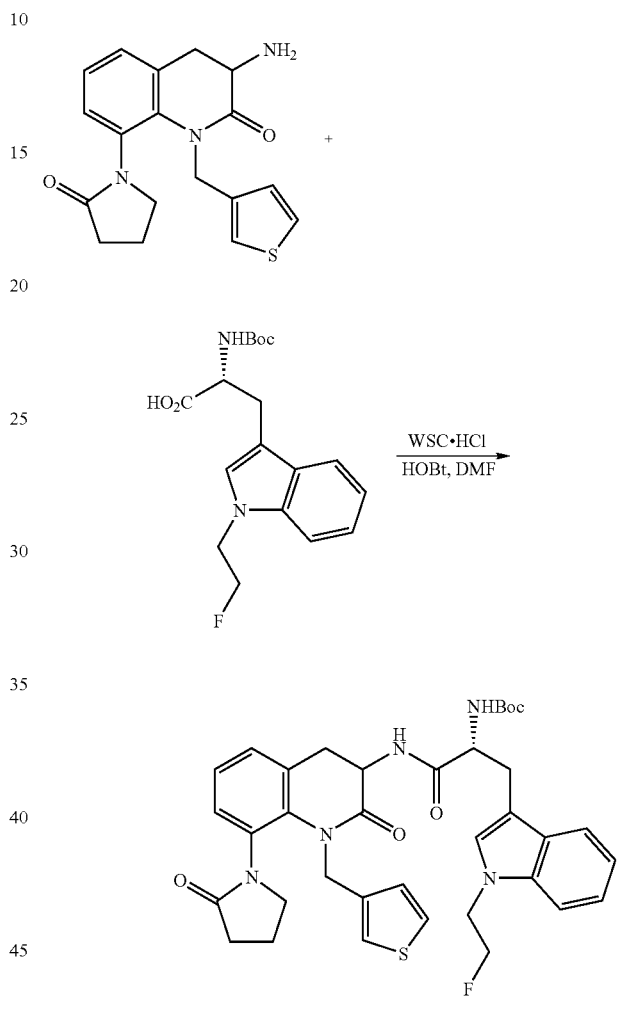

The procedure of Example 14(a) was repeated, except that (−)-3-amino-8-(2-oxopyrrolidin-1-yl)-1-(thiophen-3-ylmethyl)-3,4-dihydroquinolin-2(1H)-one (350 mg) and (R)-2-(tert-butoxycarbonylamino)-3-[1-(2-fluoroethyl)-1H-indol-3-yl]propanoic acid (431 mg) synthesized in Referential Example 1(c) were used, whereby the title compound (744 mg) was yielded.

MS(FAB)m/z674(M+H)$^+$ $^1$H-NMR(400 MHz, DMSO-d$_6$, 80° C.):

δ(ppm)1.32(9H, m), 1.82-2.07(2H, m), 2.24-2.40(2H, m), 2.59(1H, t, J=14.0 Hz), 2.79(1H, dd, J=5.0, 15.0 Hz), 2.94-3.05(1H, m), 3.14(1H, dd, J=5.5, 14.5 Hz), 3.32-3.42(1H, m), 3.70-3.82(1H, m), 4.29-4.46(4H, m), 4.54-4.66(2H, m), 4.75 (1H, t, J=5.0 Hz), 5.17(1H, d, J=15.5 Hz), 6.44(1H, s), 6.78 (1H, dd, J=1.5, 5.0 Hz), 6.98-7.06(2H, m), 7.08-7.22(5H, m), 7.33(1H, dd, J=3.0.5.0 Hz), 7.40(1H, d, J=8.0 Hz), 7.57(1H, d, J=8.0 Hz), 7.80(1H, d, J=7.0 Hz).

Example 14(e)

Synthesis of tert-butyl (2R)-1-oxo-1-[2-oxo-8-(2-oxopyrrolidin-1-yl)-1-(thiophen-3-ylmethyl)-1,2,3,4-tetrahydroquinolin-3-ylamino]-3-(1-propyl-1H-indol-3-yl)-propan-2-ylcarbamate

Example 14(f)

Synthesis of tert-butyl (2R)-3-(1-isopropyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylcarbamate

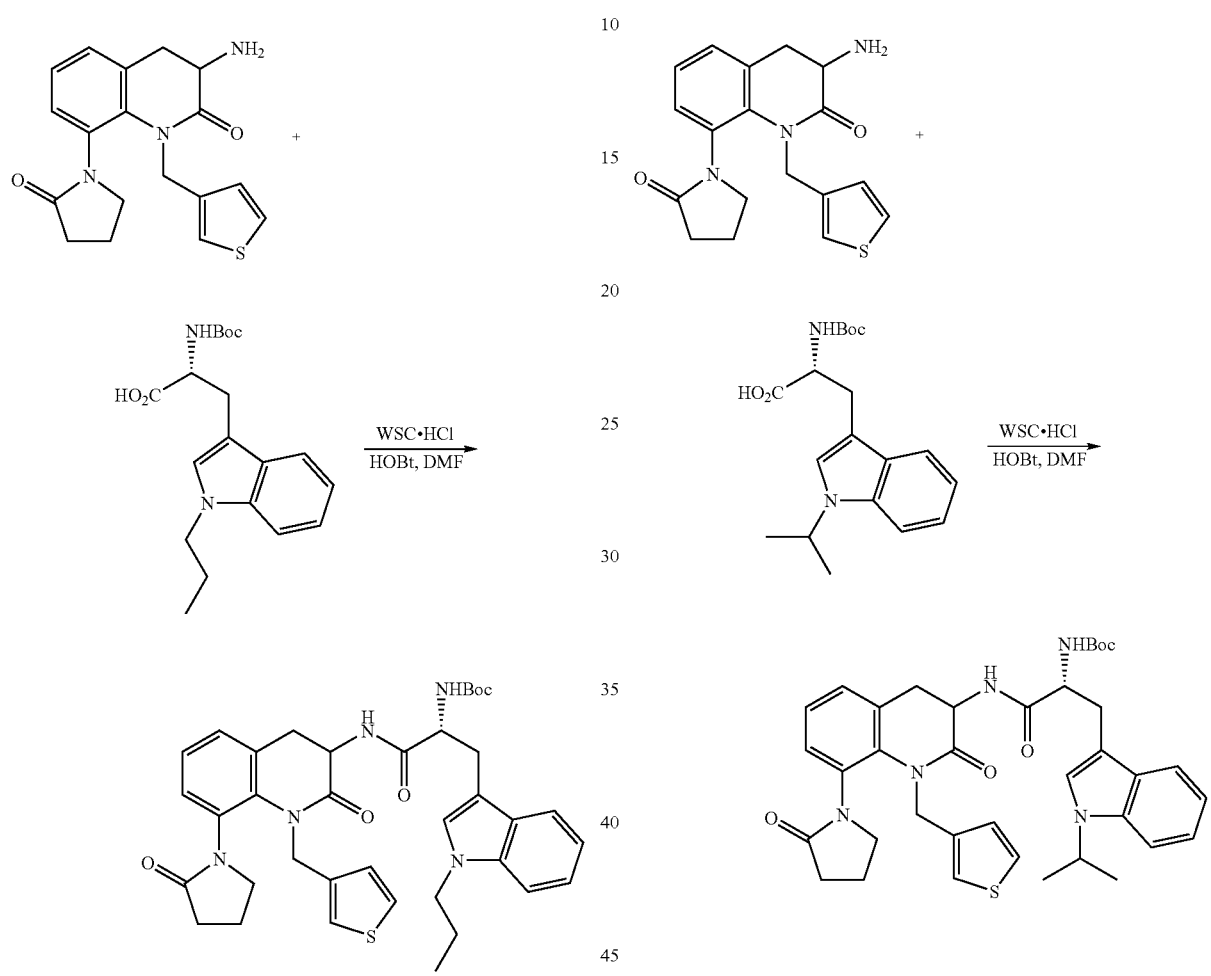

The procedure of Example 14(a) was repeated, except that (−)-3-amino-8-(2-oxopyrrolidin-1-yl)-1-(thiophen-3-ylmethyl)-3,4-dihydroquinolin-2(1H)-one (500 mg) and (R)-2-(tert-butoxycarbonylamino)-3-(1-propyl-1H-indol-3-yl)propanoic acid (641 mg) synthesized in Referential Example 1(d) were used, whereby the title compound (1.05 g) was yielded.

MS(FAB)m/z670(M+H)$^+$ $^1$H-NMR(400MHz, DMSO-d$_6$, 80° C.):

δ(ppm)0.85(3H, t, J=7.5 Hz), 1.31(9H, s), 1.72-1.81(2H, m), 1.84-2.06(2H, m), 2.25-2.39(2H, m), 2.59(1H, t, J=14.5 Hz), 2.80(1H, dd, J=5.0, 15.0 Hz), 2.92-3.03(1H, m), 3.09-3.19(1H, m), 3.33-3.42(1H, m), 3.70-3.81(1H, m), 4.04(2H, t, J=7.0 Hz), 4.27-4.42(2H, m), 4.58(1H, d, J=15.5 Hz), 5.17(1H, d, J=15.5 Hz), 6.41(1H, s), 6.78(1H, dd, J=1.5, 5.0 Hz), 6.95-7.04(2H, m), 7.06-7.20(5H, m), 7.31-7.40(2H, m), 7.53-7.58(1H, m), 7.80(1H, d, J=7.0 Hz).

The procedure of Example 14(a) was repeated, except that (−)-3-amino-8-(2-oxopyrrolidin-1-yl)-1-(thiophen-3-ylmethyl)-3,4-dihydroquinolin-2(1H)-one (500 mg) and (R)-2-(tert-butoxycarbonylamino)-3-(1-isopropyl-1H-indol-3-yl)propanoic acid (609 mg) synthesized in Referential Example 1(e) were used, whereby the title compound (1.12 g) was yielded.

MS(FAB)m/z670(M+H)$^+$ $^1$H-NMR(400 MHz, DMSO-d$_6$, 80° C.)

δ(ppm)1.32(9H, s), 1.43(3H, d, J=6.5 Hz), 1.43(3H, d, J=6.5 Hz), 1.82-2.08(2H, m), 2.24-2.40(2H, m), 2.56(1H, t, J=14.5 Hz), 2.68-2.80(1H, m), 2.90-3.15(1H, m), 3.14(1H, dd, J=6.0, 14.5 Hz), 3.30-3.42(1H, m), 3.68-3.80(1H, m), 4.27-4.42(2H, m), 4.57(1H, d, J=15.5 Hz), 4.61-4.72(1H, m), 5.17(1H, d, J=15.5 Hz), 6.36-6.50(1H, m), 6.77(1H, d, J=5.0 Hz), 6.93-7.21(6H, m), 7.26(1H, s), 7.28-7.35(1H, m), 7.40(1H, d, J=8.0 Hz), 7.55(1H, d, J=8.0 Hz), 7.79(1H, d, J=7.0 Hz).

Example 15(a)

Synthesis of (2R)-2-amino-4-methyl-N-[2-oxo-8-(2-oxopyrrolidin-1-yl)-1-(thiophen-3-ylmethyl)-1,2,3,4-tetrahydroquinolin-3-yl]pentanamide

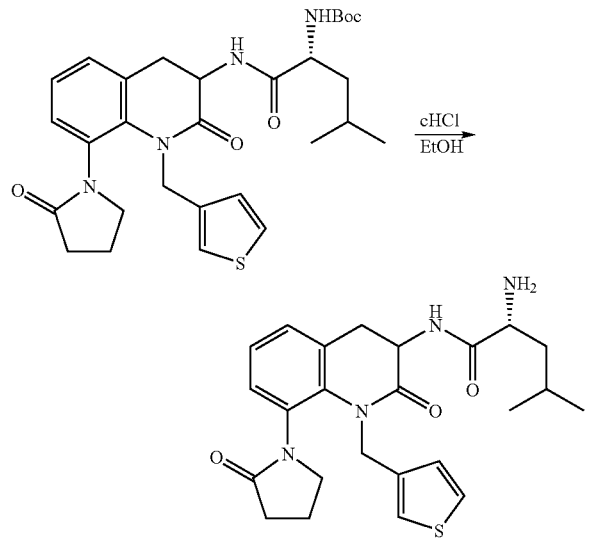

tert-Butyl (2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylcarbamate (588 mg) was dissolved in ethanol (2.9 mL), and concentrated hydrochloric acid (1.2 mL) was added thereto. The mixture was heated at 50° C. while being stirred for 30 minutes. The resultant mixture was neutralized with saturated sodium bicarbonate solution under cooling on ice. Subsequently, the mixture was extracted with ethyl acetate, and the aqueous layer was further extracted with ethyl acetate. The organic layers were combined, and the combined organic layer was washed with saturated sodium chloride solution, followed by drying over sodium sulfate. The solvent was evaporated under reduced pressure, whereby the title compound (416 mg) was yielded.

MS(FAB)m/z455(M+H)$^+$ $^1$H-NMR(400 MHz, DMSO-d$_6$, 80° C.)

δ(ppm)0.87(3H, d, J=6.5 Hz), 0.89(3H, d, J=6.5 Hz), 1.23-1.33(1H, m), 1.45-1.56(1H, m), 1.68-2.06(5H, m), 2.25-2.39 (2H, m), 2.76(1H, t, J=14.0 Hz), 2.95-3.04(1H, m), 3.28(1H, dd, J=5.0, 8.5 Hz), 3.31-3.42(1H, m), 3.68-3.80(1H, m), 4.39 (1H, dd, J=5.0, 13.5 Hz), 4.59(1H, d, J=15.5 Hz), 5.17(1H, d, J=15.5 Hz), 6.76-6.82(1H, m), 7.00-7.19(4H, m), 7.32(1H, dd, J=3.0, 5.0 Hz), 8.11(1H, br s).

Example 15(b)

Synthesis of (2R)-2-amino-3-(1-methyl-1H-indol-3-yl)-N-[2-oxo-8-(2-oxopyrrolidin-1-yl)-1-(thiophen-3-ylmethyl)-1,2,3,4-tetrahydroquinolin-3-yl]propanamide

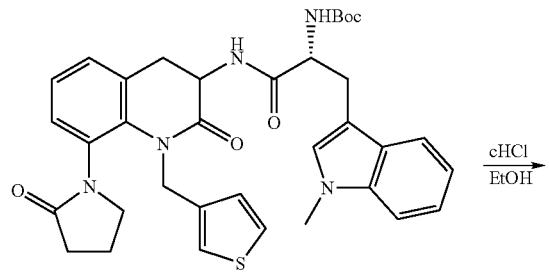

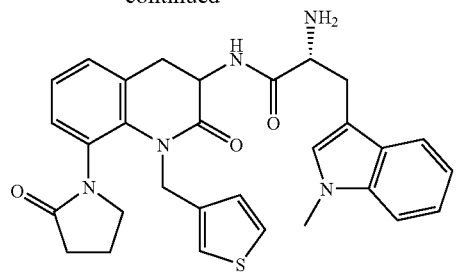

The procedure of Example 15(a) was repeated, except that tert-butyl (2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylcarbamate (549 mg) was used, whereby the title compound (357 mg) was yielded.

MS(FAB)m/z542(M+H)$^+$ $^1$H-NMR(400 MHz, DMSO-d$_6$, 80° C.):

δ(ppm)1.65-2.03(4H, m), 2.24-2.39(2H, m), 2.67(1H, t, J=14.5 Hz), 2.82(1H, dd, J=5.0, 8.0 Hz), 2.96(1H, dd, J=5.0, 10.5 Hz), 3.14(1H, dd, J=5.0, 9.5 Hz), 3.36-3.40(1H, m), 3.57(1H, dd, J=3.0, 5.0 Hz), 3.72-3.75(4H, m), 4.38(1H, dd, J=5.0, 9.0 Hz), 4.59(1H, d, J=16.0 Hz), 5.15(1H, d, J=16.0 Hz), 6.79(1H, d, J=4.0 Hz), 6.97-7.03(2H, m), 7.09-7.19(5H, m), 7.30-7.36(2H, m), 7.55(1H, d, J=8.0 Hz), 8.02(1H, br).

Example 15(c)

Synthesis of (2R)-2-amino-3-(1-ethyl-1H-indol-3-yl)-N-[2-oxo-8-(2-oxopyrrolidin-1-yl)-1-(thiophen-3-ylmethyl)-1,2,3,4-tetrahydroquinolin-3-yl]propanamide

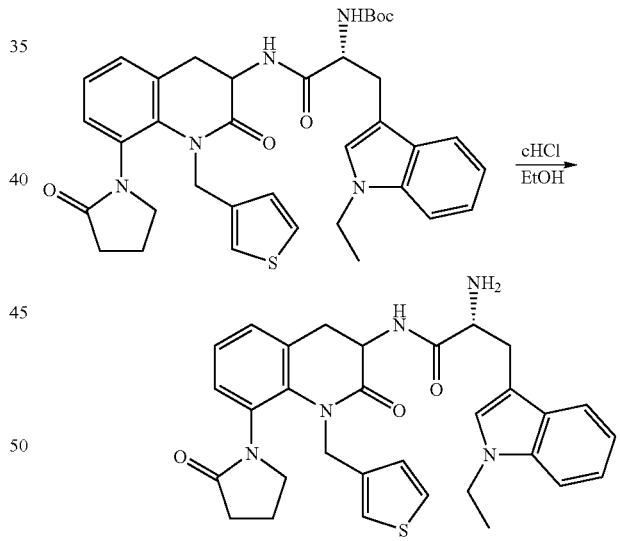

The procedure of Example 15(a) was repeated, except that tert-butyl (2R)-3-(1-ethyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylcarbamate (283 mg) was used, whereby the title compound (206 mg) was yielded.

MS(FAB)m/z556(M+H)$^+$ $^1$H-NMR(400 MHz, DMSO-d$_6$, 80° C.):

δ(ppm)1.33(3H, t, J=7.0 Hz), 1.74-2.43(7H, m), 2.69-2.81 (2H, m), 2.89(1H, dd, J=5.0, 10.0 Hz), 3.12(1H, dd, J=5.0, 10.0 Hz), 3.55(1H, dd, J=3.5, 5.5 Hz), 4.15(2H, q, J=7.0 Hz), 4.25-5.23(4H, m), 6.80(1H, d, J=5.0 Hz), 7.00(1H, t, J=7.5 Hz), 7.06-7.21(5H, m), 7.27(1H, s), 7.38-7.47(2H, m), 7.56 (1H, d, J=8.0 Hz), 8.38(1H, d, J=7.0 Hz).

Example 15(d)

Synthesis of (2R)-2-amino-3-[1-(2-fluoroethyl)-1H-indol-3-yl]-N-[2-oxo-8-(2-oxopyrrolidin-1-yl)-1-(thiophen-3-ylmethyl)-1,2,3,4-tetrahydroquinolin-3-yl]propanamide

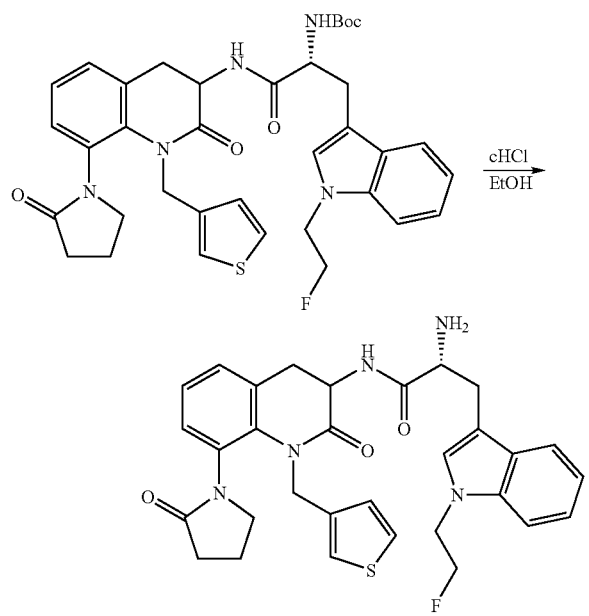

The procedure of Example 15(a) was repeated, except that tert-butyl (2R)-3-[1-(2-fluoroethyl)-1H-indol-3-yl]-1-oxo-1-[2-oxo-8-(2-oxopyrrolidin-1-yl)-1-(thiophen-3-ylmethyl)-1,2,3,4-tetrahydroquinolin-3-ylamino]propan-2-ylcarbamate (590 mg) was used, whereby the title compound (466 mg) was yielded.

MS(FAB)m/z574(M+H)+
1H-NMR(400 MHz, DMSO-d6, 80° C.):
δ(ppm)1.70-2.09(4H, m), 2.21-2.39(2H, m), 2.67(1H, t, J=14.5 Hz), 2.83(1H, dd, J=8.0, 14.0 Hz), 2.88-2.97(1H, m), 3.06-3.17(1H, m), 3.30-3.41(1H, m), 3.52-3.62(1H, m), 3.68-3.80(1H, m), 4.30-4.48(3H, m), 4.52-4.68(2H, m), 4.70-4.80 (1H, m), 5.15(1H, d, J=15.5 Hz), 6.79(1H, d, J=5.0 Hz), 6.95-7.04(2H, m), 7.05-7.23(5H, m), 7.27-7.34(1H, m), 7.41 (1H, d, J=8.0 Hz), 7.57(1H, d, J=8.0 Hz), 8.03-8.14(1H, m).

Example 15(e)

Synthesis of (2R)-2-amino-N-[2-oxo-8-(2-oxopyrrolidin-1-yl)-1-(thiophen-3-ylmethyl)-1,2,3,4-tetrahydroquinolin-3-yl]-3-(1-propyl-1H-indol-3-yl)-propanamide

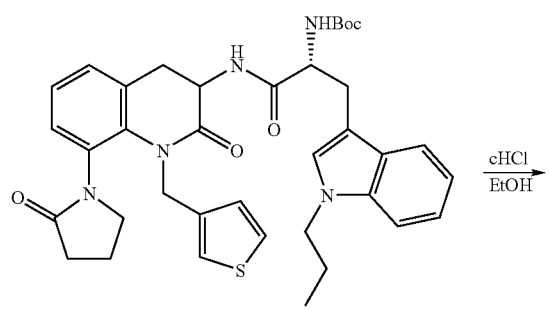

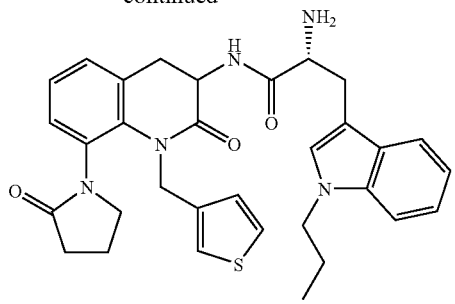

The procedure of Example 15(a) was repeated, except that tert-butyl (2R)-1-oxo-1-[2-oxo-8-(2-oxopyrrolidin-1-yl)-1-(thiophen-3-ylmethyl)-1,2,3,4-tetrahydroquinolin-3-ylamino]-3-(1-propyl-1H-indol-3-yl)-propan-2-ylcarbamate (779 mg) was used, whereby the title compound (560 mg) was yielded.

MS(FAB)m/z570(M+H)+
1H-NMR(400 MHz, DMSO-d6, 80° C.):
δ(ppm)0.85(3H, t, J=7.0 Hz), 1.57-2.07(6H, m), 2.22-2.38 (2H, m), 2.60-2.71(1H, m), 2.80-2.98(2H, m), 3.12(1H, dd, J=5.0, 14.5 Hz), 3.33-3.41(1H, m), 3.53-3.62(1H, m), 3.69-3.79(1H, m), 3.98-4.08(2H, m), 4.31-4.41(1H, m), 4.59(1H, d, J=15.5 Hz), 5.15(1H, d, J=15.5 Hz), 6.80(1H, d, J=7.1 Hz), 6.99(1H, t, J=7.2 Hz), 7.07-7.19(5H, m), 7.24(1H, s), 7.38-7.43(2H, m), 7.56(1H, d, J=7.7 Hz), 8.38(1H, J=7.1 Hz).

Example 15(f)

Synthesis of (2R)-2-amino-3-(1-isopropyl-1H-indol-3-yl)-N-[2-oxo-8-(2-oxopyrrolidin-1-yl)-1-(thiophen-3-ylmethyl)-1,2,3,4-tetrahydroquinolin-3-yl]propanamide

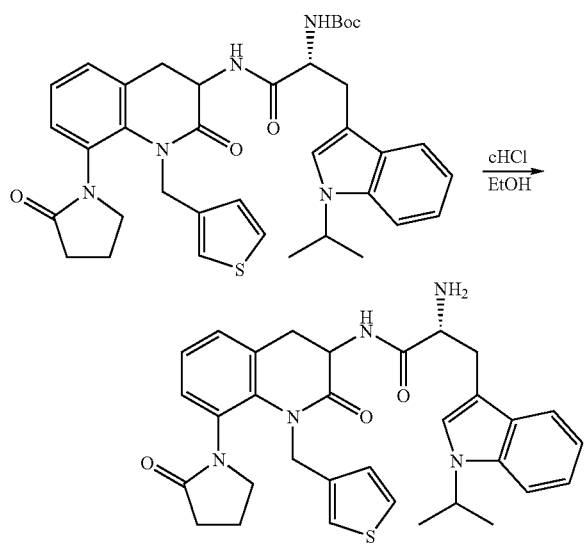

The procedure of Example 15(a) was repeated, except that tert-butyl (2R)-3-(1-isopropyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylcarbamate (800 mg) was used, whereby the title compound (651 mg) was yielded.

MS(FAB)m/z570(M+H)⁺

¹H-NMR(400 MHz, DMSO-d₆, 80° C.):

δ(ppm)1.44(3H, d, J=6.5 Hz), 1.44(3H, d, J=6.5 Hz), 1.80-2.17(4H, m), 2.22-2.38(2H, m), 2.64(1H, t, J=14.5 Hz), 2.76-2.95(2H, m), 3.13(1H, dd, J=5.0, 14.5 Hz), 3.30-3.42(1H, m), 3.54-3.64(1H, m), 3.68-3.80(1H, m), 4.30-4.42(1H, m), 4.58(1H, d, J=15.5 Hz), 4.62-4.72(1H, m), 5.15(1H, d, J=15.5 Hz), 6.78(1H, d, J=5.0 Hz), 6.93-7.20(6H, m), 7.24-7.34(2H, m), 7.41(1H, d, J=8.0 Hz), 7.55(1H, d, J=8.0 Hz), 7.98-8.15 (1H, m).

Example 15(g)

Synthesis of (2R)-2-amino-3-(1H-indol-3-yl)-N-[2-oxo-8-(2-oxopyrrolidin-1-yl)-1-(thiophen-3-ylmethyl)-1,2,3,4-tetrahydroquinolin-3-yl]propanamide

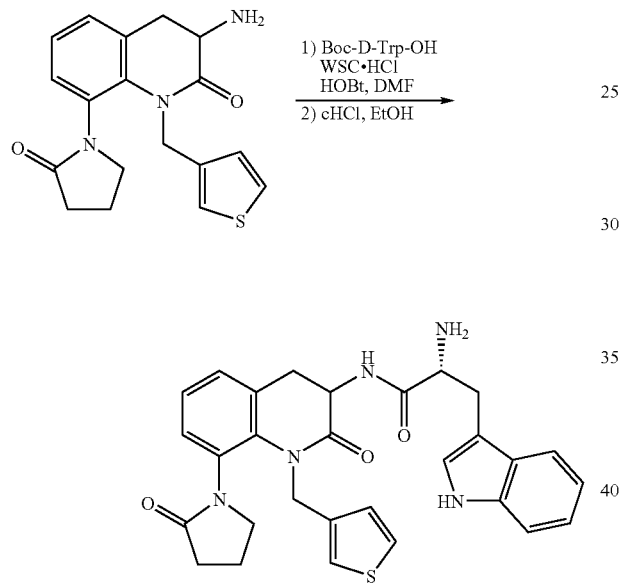

The procedure of Example 14(a) was repeated, except that (−)-3-amino-8-(2-oxopyrrolidin-1-yl)-1-(thiophen-3-ylmethyl)-3,4-dihydroquinolin-2(1H)-one (300 mg) and N-tert-butoxycarbonyl-D-tryptophan (294 mg) were used, whereby tert-butyl (2R)-3-(1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylcarbamate was yielded. Subsequently, the procedure of Example 15(a) was repeated, except that the compound prepared as described above was used, whereby the title compound (438 mg) was yielded.

MS(FAB)m/z528(M+H)⁺

¹H-NMR(400 MHz, DMSO-d₆, 80° C.):

δ(ppm)1.65-2.07(4H, m), 2.23-2.39(2H, m), 2.67(1H, t, J=14.5 Hz), 2.82(1H, dd, J=8.0, 14.0 Hz), 2.94(1H, dd, J=5.0, 14.5 Hz), 3.14(1H, dd, J=5.0, 14.5 Hz), 3.33-3.42(1H, m), 3.59(1H, dd, J=2.0, 8.0 Hz), 3.70-3.79(1H, m), 4.38(1H, dd, J=5.0, 13.5 Hz), 4.58(1H, d, J=15.5 Hz), 5.16(1H, d, J=15.5 Hz), 6.79(1H, dd, J=1.0, 5.0 Hz), 6.93-7.19(7H, m), 7.28-7.36(2H, m), 7.54(1H, d, J=8.0 Hz), 8.10(1H, br s), 10.58(1H, br s).

Example 16

Synthesis of N-(8-amino-2-oxo-1,2,3,4-tetrahydroquinolin-3-yl)acetamide

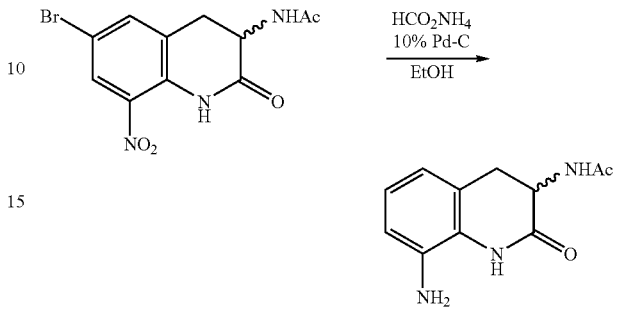

N-(6-Bromo-8-nitro-2-oxo-1,2,3,4-tetrahydroquinolin-3-yl)acetamide (15 g) was suspended in ethanol (150 mL), and ammonium formate (28.8 g) and 10% Pd—C (water content: 53%) (1.5 g) were added thereto. The mixture was heated at 80° C. while being stirred for 30 minutes, and water (150 mL) and ethanol (150 mL) were added thereto, followed by filtration while being heated. The filtrate was concentrated under reduced pressure, and the formed precipitates were recovered through filtration. The thus-obtained solid was washed with ethanol and diisopropyl ether, followed by drying, whereby the title compound (8.5 g) was yielded.

MS(FAB)m/z220(M+H)⁺

¹H-NMR(400 MHz, DMSO-d₆):

δ(ppm)1.90(3H, s), 2.73-2.93(2H, m), 4.33-4.43(1H, m), 5.06(2H, s), 6.42(1H, d, J=7.5 Hz), 6.55(1H, d, J=7.5 Hz), 6.70(1H, d, J=7.5 Hz), 8.16(1H, d, J=8.0 Hz), 9.54(1H, s).

Example 17

Synthesis of 3,8-diamino-3,4-dihydroquinolin-2(1H)-one dihydrochloride

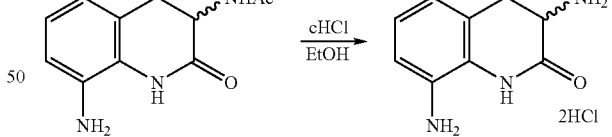

N-(8-Amino-2-oxo-1,2,3,4-tetrahydroquinolin-3-yl)acetamide (8.4 g) was added to concentrated hydrochloric acid (84 mL), and the mixture was heated at 110° C. for three hours while being stirred, followed by stirring under cooling on ice. The formed precipitates were recovered through filtration, and the thus-obtained solid was washed with ethanol, followed by drying, whereby the title compound (9.17 g) was yielded.

MS(FAB)m/z178(M+H)⁺

¹H-NMR(400 MHz, DMSO-d₆):

δ(ppm)3.06-3.25(2H, m), 4.15-4.27(1H, m), 6.93-7.01 (2H, m), 7.03-7.11(1H, m), 7.45-8.20(3H, br), 8.62-8.78(3H, m), 10.43(1H, s).

Example 18

Synthesis of (2R)-2-amino-N-(8-amino-2-oxo-1,2,3,4-tetrahydroquinolin-3-yl)-4-methylpentanamide

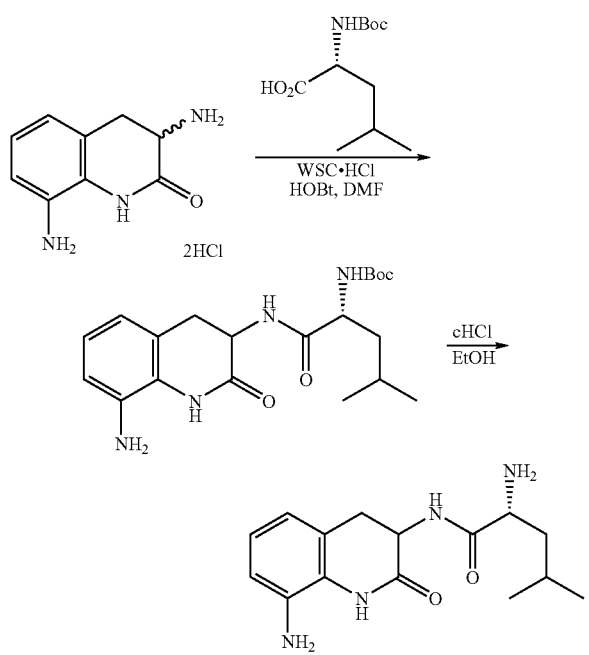

3,8-Diamino-3,4-dihydroquinolin-2(1H)-one dihydrochloride (9.0 g) was suspended in N,N-dimethylformaldehyde (90 mL), and triethylamine (15 mL) was added to the suspension under cooling on ice. Subsequently, N-tert-butoxycarbonyl-D-leucine monohydrate (9.87 g), 1-hydroxybenzotriazole (4.86 g), and 1-ethyl-3-(3-dimethylaminopropyl)carbodiimide hydrochloride (7.67 g) were sequentially added to the mixture, followed by stirring at room temperature for one hour. To the resultant mixture were added saturated aqueous sodium bicarbonate solution, ethyl acetate, and water, and the mixture was subjected to extraction. The organic layer was sequentially washed with water and saturated aqueous sodium chloride solution, and was dried over sodium sulfate. The solvent was evaporated under reduced pressure, and the precipitates were filtered by use of ethyl acetate, whereby tert-butyl (2R)-1-(8-amino-2-oxo-1,2,3,4-tetrahydroquinolin-3-ylamino)-4-methyl-1-oxopentan-2-ylcarbamate (12.4 g) was yielded as a diastereomeric mixture. Subsequently, the thus-obtained tert-butyl (2R)-1-(8-amino-2-oxo-1,2,3,4-tetrahydroquinolin-3-ylamino)-4-methyl-1-oxopentan-2-ylcarbamate (7.68 g) was dissolved in ethanol (77 mL), and concentrated hydrochloric acid (34 mL) was added thereto, followed by heating to 60° C. while being stirred for 30 minutes. The resultant mixture was neutralized with saturated aqueous sodium bicarbonate solution under cooling on ice and was then subjected to extraction with chloroform. The organic layer was washed with saturated aqueous sodium chloride solution and dried over sodium sulfate. The solvent was evaporated under reduced pressure, and the thus-recovered residue was purified through silica gel column chromatography (chloroform:methanol=15:1), whereby the title compound (diastereomer of lower polarity: 2.85 g, diastereomer of higher polarity: 2.73 g) was yielded.

Diastereomer of Lower Polarity:
MS(FAB)m/z291(M+H)$^+$
$^1$H-NMR(400 MHz, DMSO-d$_6$):
δ(ppm)0.87(3H, d, J=6.5 Hz), 0.91(3H, d, J=6.5 Hz), 1.22-1.31(1H, m), 1.43-1.52(1H, m), 1.72-1.90(3H, m), 2.76(1H, t, J=14.5 Hz), 3.00(1H, dd, J=6.0, 15.0 Hz), 3.21(1H, dd, J=4.5, 9.5 Hz), 4.29(1H, dt, J=6.0, 15.0 Hz), 5.07(2H, s), 6.43(1H, d, J=7.5 Hz), 6.55(1H, d, J=7.5 Hz), 6.71(1H, t, J=7.5 Hz), 8.34(1H, d, J=7.0 Hz), 9.60(1H, s).

Diastereomer of Higher Polarity:
MS(FAB)m/z291(M+H)$^+$
$^1$H-NMR(400 MHz, DMSO-d$_6$):
δ(ppm)0.87(3H, d, J=6.5 Hz), 0.89(3H, d, J=6.5 Hz), 1.21-1.30(1H, m), 1.43-1.51(1H, m), 1.70-1.88(3H, m), 2.78(1H, t, J=14.5 Hz), 2.99(1H, dd, J=6.0, 15.0 Hz), 3.24(1H, dd, J=4.5, 9.5 Hz), 4.26-4.35(1H, m), 5.07(2H, s), 6.43(1H, d, J=7.5 Hz), 6.55(1H, d, J=7.5 Hz), 6.70(1H, t, J=7.5 Hz), 8.32(1H, d, J=7.0 Hz), 9.60(1H, s).

Example 19

Synthesis of tert-butyl (2R)-1-(8-amino-2-oxo-1,2,3,4-tetrahydroquinolin-3-ylamino)-4-methyl-1-oxopentan-2-ylcarbamate

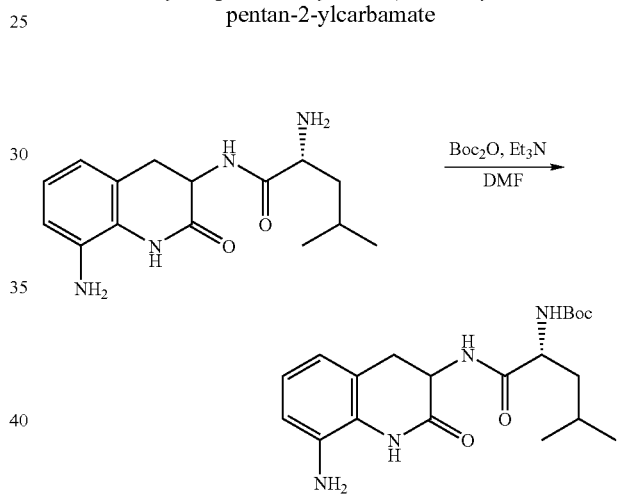

(2R)-2-Amino-N-(8-amino-2-oxo-1,2,3,4-tetrahydroquinolin-3-yl)-4-methylpentanamide (2.38 g), the diastereomer of higher polarity obtained in Example 18, was suspended in N,N-dimethylformaldehyde (12 mL), and the suspension was stirred under cooling on ice. Di-tert-butoxycarbonate (1.96 g) and triethylamine (1.25 mL) were added to the resultant mixture, and stirring was performed at room temperature for 30 minutes. The resultant mixture was extracted with water and ethyl acetate, and the organic layer was sequentially washed with water and saturated aqueous sodium chloride solution. The organic layer was dried over sodium sulfate, and the solvent was evaporated under reduced pressure. The formed precipitates were recovered through filtration, and was dried, whereby the title compound (2.59 g) was yielded.

MS(FAB)m/z391(M+H)$^+$
$^1$H-NMR(400 MHz, DMSO-d$_6$):
δ(ppm)0.87(3H, d, J=6.5 Hz), 0.88(3H, d, J=6.5 Hz), 1.39(9H, s), 1.41-1.50(2H, m), 1.56-1.68(1H, m), 2.72-2.82(1H, m), 2.91(1H, dd, J=6.0, 15.0 Hz), 4.03-4.12(1H, m), 4.29-4.38(1H, m), 5.07(2H, s), 6.42(1H, d, J=7.5 Hz), 6.55(1H, d, J=7.5 Hz), 6.70(1H, t, J=7.5 Hz), 6.96(1H, d, J=8.5 Hz), 8.05(1H, d, J=7.5 Hz), 9.59(1H, s).

Example 20

Synthesis of tert-butyl (2R)-1-[8-(4-chlorobutanamido)-2-oxo-1,2,3,4-tetrahydroquinolin-3-ylamino]-4-methyl-1-oxopentan-2-ylcarbamate

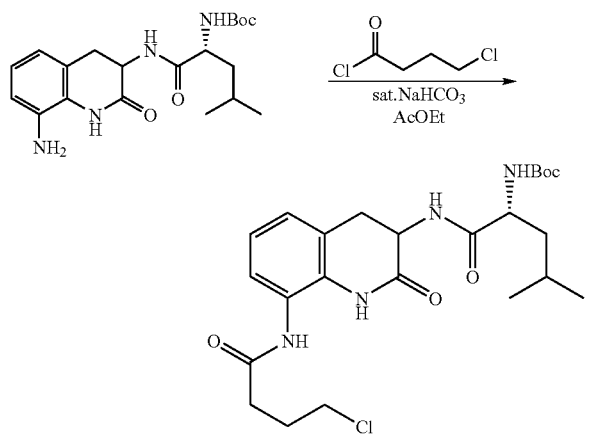

tert-Butyl (2R)-1-(8-amino-2-oxo-1,2,3,4-tetrahydroquinolin-3-ylamino)-4-methyl-1-oxopentan-2-ylcarbamate (300 mg) was dissolved in ethyl acetate (5 mL), and 4-chlorobutyryl chloride (0.1 mL) and saturated aqueous sodium bicarbonate solution (5 mL) were added thereto. The mixture was stirred under cooling on ice for 45 minutes and then subjected to extraction with water and ethyl acetate. The organic layer was washed with saturated aqueous sodium chloride solution, and was dried over sodium sulfate. The solvent was evaporated under reduced pressure, whereby the title compound (377 mg) was yielded.

MS(FAB)m/z496(M+H)+

¹H-NMR(400 MHz, DMSO-d₆):
δ(ppm)0.87(3H, d, J=6.5 Hz), 0.88(3H, d, J=6.5 Hz), 1.39 (9H, s), 1.42-1.52(2H, m), 1.56-1.69(1H, m), 1.98-2.08(2H, m), 2.48-2.56(2H, m), 2.83-2.94(1H, m), 3.04(1H, dd, J=6.0, 15.0 Hz), 3.71(2H, t, J=6.5 Hz), 4.04-4.14(1H, m), 4.35-4.45 (1H, m), 6.93(1H, d, J=8.0 Hz), 6.95(1H, d, J=8.0 Hz), 7.06 (1H, d, J=7.5 Hz), 7.33(1H, d, J=8.0 Hz), 8.13(1H, d, J=7.5 Hz), 9.37(1H, s), 9.73(1H, s).

Example 21

Synthesis of tert-butyl (2R)-4-methyl-1-oxo-1-[2-oxo-8-(2-oxopyrrolidin-1-yl)-1,2,3,4-tetrahydroquinolin-3-ylamino]pentan-2-ylcarbamate

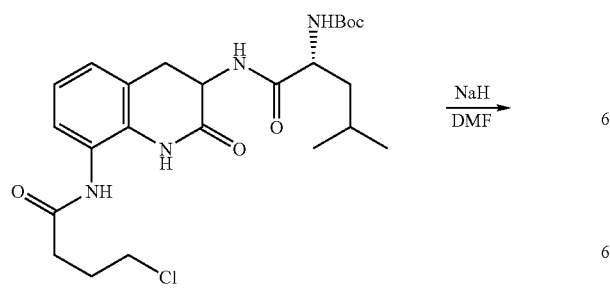

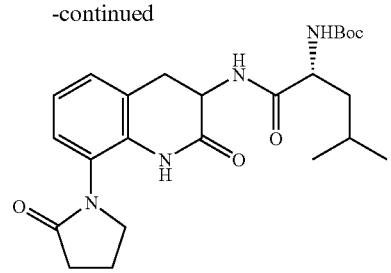

tert-Butyl (2R)-1-[8-(4-chlorobutanamido)-2-oxo-1,2,3,4-tetrahydroquinolin-3-ylamino]-4-methyl-1-oxopentan-2-ylcarbamate (350 mg) was dissolved in N,N-dimethylformaldehyde (4.0 mL), and sodium hydride (34 mg) was added thereto under cooling on ice, followed by stirring for 1.5 hours. The resultant mixture was extracted with water and ethyl acetate. The organic layer was washed with saturated aqueous sodium chloride solution, and then dried over sodium sulfate. The solvent was evaporated under reduced pressure, whereby the title compound (325 mg) was yielded.

MS(FAB)m/z459(M+H)+

¹H-NMR(400 MHz, DMSO-d₆):
δ(ppm)0.87(3H, d, J=6.5 Hz), 0.88(3H, d, J=6.5 Hz), 1.39 (9H, s), 1.42-1.50(2H, m), 1.56-1.70(1H, m), 2.08-2.18(2H, m), 2.40(2H, t, J=8.0 Hz), 2.90(1H, t, J=15.0 Hz), 3.06(1H, dd, J=6.0, 15.0 Hz), 3.56-3.74(2H, m), 4.04-4.13(1H, m), 4.36-4.46(1H, m), 6.92-7.03(2H, m), 7.12(1H, d, J=7.5 Hz), 7.18(1H, d, J=7.5 Hz), 8.13(1H, d, J=7.5 Hz), 9.81(1H, s).

Example 22

Synthesis of tert-butyl (2R)-4-methyl-1-oxo-1-[2-oxo-8-(2-oxopyrrolidin-1-yl)-1-(pyridin-2-ylmethyl)-1,2,3,4-tetrahydroquinolin-3-ylamino]pentan-2-ylcarbamate

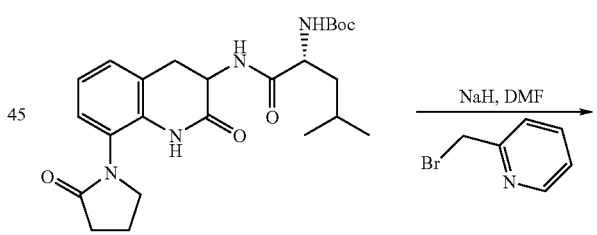

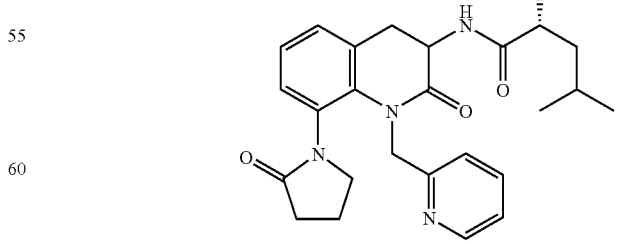

tert-Butyl (2R)-4-methyl-1-oxo-1-[2-oxo-8-(2-oxopyrrolidin-1-yl)-1,2,3,4-tetrahydroquinolin-3-ylamino]pentan-2-ylcarbamate (320 mg) was dissolved in N,N-dimethylformaldehyde (4.0 mL), and 2-bromomethylpyridine hydrobromide (216 mg) and sodium hydride (67 mg) were added thereto under cooling on ice, followed by stirring for one hour. The resultant mixture was subjected to extraction with saturated aqueous ammonium chloride solution and ethyl acetate. The organic layer was washed with water and saturated aqueous sodium chloride solution, and then dried over sodium sulfate. The solvent was evaporated under reduced pressure, and the thus-recovered residue was purified through silica gel column chromatography (ethyl acetate: methanol=20:1), whereby the title compound (315 mg) was yielded.

MS(FAB)m/z550(M+H)$^+$ $^1$H-NMR(400 MHz, DMSO-d$_6$):

δ(ppm)0.86(3H, d, J=6.5 Hz), 0.87(3H, d, J=6.5 Hz), 1.37 (9H, s), 1.40-1.50(2H, m), 1.55-1.67(1H, m), 1.72-1.86(1H, m), 1.90-2.14(2H, m), 2.20-2.36(1H, m), 2.93-3.10(2H, m), 3.20-3.52(2H, m), 3.88-4.14(1H, m), 4.32-5.20(3H, m), 7.00 (1H, d, J=8.5 Hz), 7.06-7.33(5H, m), 7.63-7.75(1H, m), 8.14 (1H, d, J=7.0 Hz), 8.39-8.48(1H, m).

Example 23

Synthesis of (2R)-2-amino-4-methyl-N-[2-oxo-8-(2-oxopyrrolidin-1-yl)-1-(pyridin-2-ylmethyl)-1,2,3,4-tetrahydroquinolin-3-yl]pentanamide

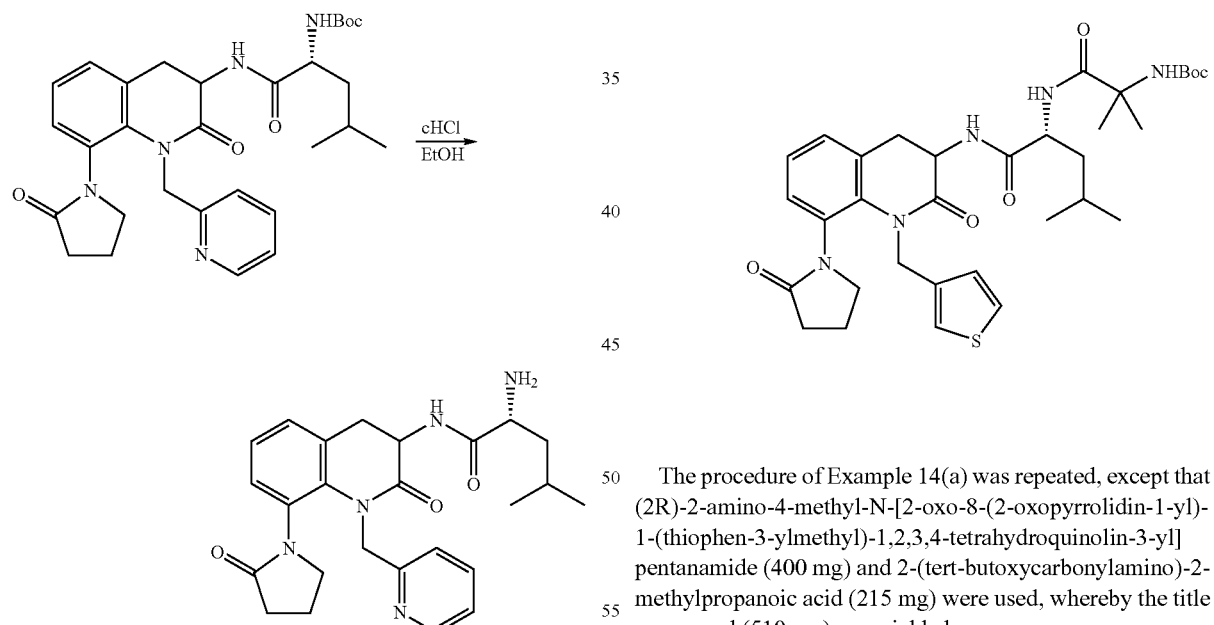

The procedure of Example 15(a) was repeated, except that tert-butyl (2R)-4-methyl-1-oxo-1-[2-oxo-8-(2-oxopyrrolidin-1-yl)-1-(pyridin-2-ylmethyl)-1,2,3,4-tetrahydroquinolin-3-ylamino]pentan-2-ylcarbamate (300 mg) was used, whereby the title compound (234 mg) was yielded.

MS(FAB)m/z450(M+H)$^+$ $^1$H-NMR(400 MHz, DMSO-d$_6$, 80° C.):

δ(ppm)0.87(3H, d, J=6.5 Hz), 0.89(3H, d, J=6.5 Hz), 1.24-1.33(1H, m), 1.46-1.56(1H, m), 1.60-1.98(5H, m), 2.12-2.29 (2H, m), 2.95-3.13(2H, m), 3.22-3.44(2H, m), 3.67-3.78(1H, m), 4.45(1H, dd, J=6.0, 13.0 Hz), 4.75(1H, d, J=16.5 Hz), 5.14(1H, d, J=16.5 Hz), 7.07-7.23(5H, m), 7.64(1H, dt, J=2.0, 7.5 Hz), 8.00-8.22(1H, br), 8.40(1H, d, J=4.5 Hz).

Example 24(a)

Synthesis of tert-butyl 2-methyl-1-[(2R)-4-methyl-1-oxo-1-[2-oxo-8-(2-oxopyrrolidin-1-yl)-1-(thiophen-3-ylmethyl)-1,2,3,4-tetrahydroquinolin-3-ylamino] pentan-2-ylamino]-1-oxopropan-2-ylcarbamate

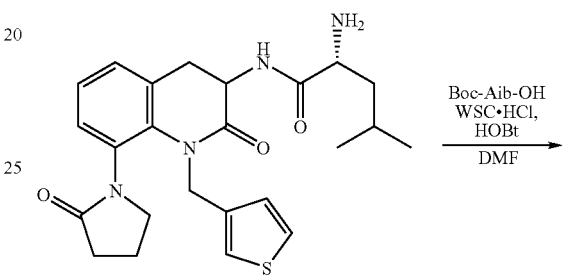

The procedure of Example 14(a) was repeated, except that (2R)-2-amino-4-methyl-N-[2-oxo-8-(2-oxopyrrolidin-1-yl)-1-(thiophen-3-ylmethyl)-1,2,3,4-tetrahydroquinolin-3-yl] pentanamide (400 mg) and 2-(tert-butoxycarbonylamino)-2-methylpropanoic acid (215 mg) were used, whereby the title compound (510 mg) was yielded.

MS(FAB)m/z640(M+H)$^+$ $^1$H-NMR(400 MHz, DMSO-d$_6$):

δ(ppm)0.85(3H, d, J=6.5 Hz), 0.87(3H, d, J=6.5 Hz), 1.33 (3H, s), 1.35(3H, s), 1.37(9H, s), 1.49-1.72(3H, m), 1.81-2.06 (2H, m), 2.23-2.39(2H, m), 2.77(1H, t, J=14.5 Hz), 2.92(1H, dd, J=5.0, 14.5 Hz), 3.31-3.40(1H, m), 3.68-3.79(1H, m), 4.30-4.45(2H, m), 4.58(1H, d, J=15.5 Hz), 5.16(1H, d, J=15.5 Hz), 6.56(1H, br s), 6.73-6.80(1H, m), 6.98-7.19(4H, m), 7.27-7.36(2H, m), 7.83(1H, d, J=7.0 Hz).

Example 24(b)

Synthesis of tert-butyl 2-methyl-1-[(2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-1-oxopropan-2-ylcarbamate

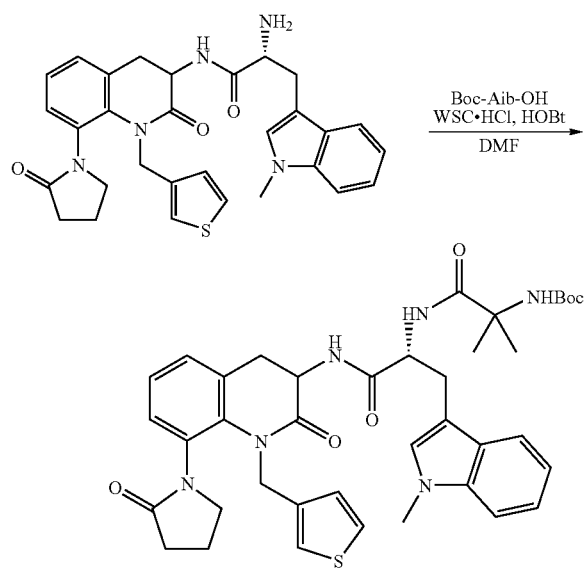

The procedure of Example 14(a) was repeated, except that (2R)-2-amino-3-(1-methyl-1H-indol-3-yl)-N-[2-oxo-8-(2-oxopyrrolidin-1-yl)-1-(thiophen-3-ylmethyl)-1,2,3,4-tetrahydroquinolin-3-yl]propanamide (344 mg) was used, whereby the title compound (502 mg) was yielded.

MS(FAB)m/z727(M+H)$^+$ $^1$H-NMR(400 MHz, DMSO-d$_6$):

δ(ppm)1.25(6H, d, J=5.0 Hz), 1.31(9H, s), 1.81-2.42(4H, m), 2.61-2.79(2H, m), 3.05-3.18(2H, m), 3.22-3.55(3H, m), 3.72(3H, s), 4.29-5.36(4H, m), 6.73-6.81(1H, m), 6.98-7.21 (8H, m), 7.35-7.42(2H, m), 7.56(1H, d, J=7.0 Hz), 8.18(1H, br).

Example 24(c)

Synthesis of tert-butyl 1-[(2R)-3-(1-ethyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-2-methyl-1-oxopropan-2-ylcarbamate

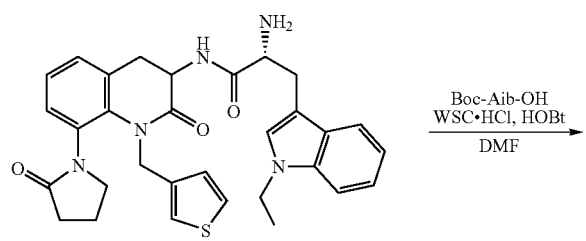

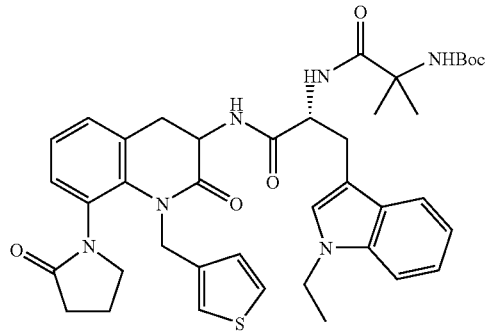

The procedure of Example 14(a) was repeated, except that (2R)-2-amino-3-(1-ethyl-1H-indol-3-yl)-N-[2-oxo-8-(2-oxopyrrolidin-1-yl)-1-(thiophen-3-ylmethyl)-1,2,3,4-tetrahydroquinolin-3-yl]propanamide (206 mg) was used, whereby the title compound (292 mg) was yielded.

MS(FAB)m/z741(M+H)$^+$ $^1$H-NMR(400 MHz, DMSO-d$_6$):

δ(ppm)1.23(3H, s), 1.25(3H, s), 1.27-1.35(12H, m), 1.80-2.42(4H, m), 2.57-2.78(2H, m), 3.05-3.16(2H, m), 3.25-3.61 (2H, m), 4.13(2H, q, J=7.0 Hz), 4.32-5.29(4H, m), 6.76(1H, d, J=4.0 Hz), 6.98-7.23(8H, m), 7.37-7.43(2H, m), 7.55(2H, d, J=8.0 Hz), 8.16(1H, br).

Example 24(d)

Synthesis of tert-butyl 1-[(2R)-3-[1-(2-fluoroethyl)-1H-indol-3-yl]-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-2-methyl-1-oxopropan-2-ylcarbamate

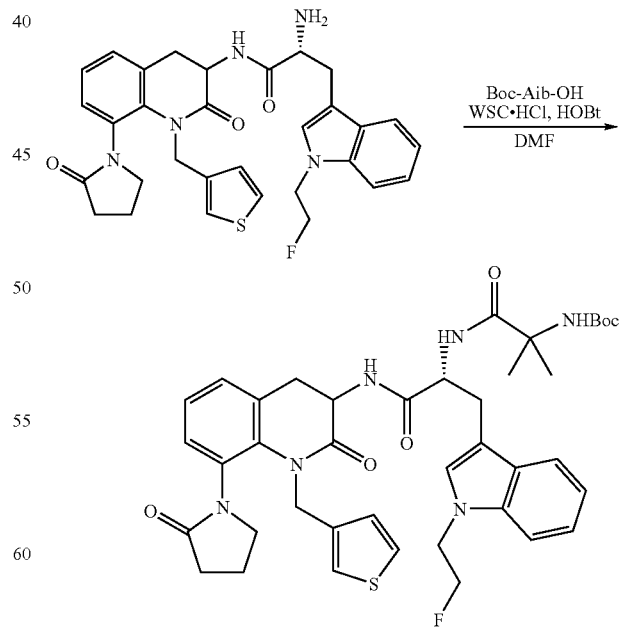

The procedure of Example 14(a) was repeated, except that (2R)-2-amino-3-[1-(2-fluoroethyl)-1H-indol-3-yl]-N-[2-oxo-8-(2-oxopyrrolidin-1-yl)-1-(thiophen-3-ylmethyl)-1,2, 3,4-tetrahydroquinolin-3-yl]propanamide (440 mg) was used, whereby the title compound (490 mg) was yielded.

MS(FAB)m/z759(M+H)⁺

¹H-NMR(400 MHz, DMSO-d₆, 80° C.):
δ(ppm)1.28(3H, s), 1.29(3H, s), 1.32(9H, s), 1.81-2.06 (2H, m), 2.22-2.39(2H, m), 2.55-2.70(1H, m), 3.06-3.20(2H, m), 3.31-3.39(1H, m), 3.67-3.80(1H, m), 4.32-4.46(3H, m), 4.51-4.67(3H, m), 4.75(1H, t, J=5.0 Hz), 5.16(1H, d, J=15.5 Hz), 6.58(1H, s), 6.76(1H, dd, J=1.0, 5.0 Hz), 6.97-7.22(7H, m), 7.27-7.35(2H, m), 7.40(1H, d, J=8.0 Hz), 7.57(1H, d, J=8.0 Hz), 7.79(1H, d, J=7.5 Hz).

Example 24(e)

Synthesis of tert-butyl 2-methyl-1-oxo-1-[(2R)-1-oxo-1-[2-oxo-8-(2-oxopyrrolidin-1-yl)-1-(thiophen-3-ylmethyl)-1,2,3,4-tetrahydroquinolin-3-ylamino]-3-(1-propyl-1H-indol-3-yl)propan-2-ylamino]propan-2-ylcarbamate The procedure of Example 14(a) was repeated, except that (2R)-2-amino-N-[2-oxo-8-(2-oxopyrrolidin-1-yl)-1-(thiophen-3-ylmethyl)-1,2,3,4-tetrahydroquinolin-3-yl]-3-(1-propyl-1H-indol-3-yl)-propanamide (470 mg) was used, whereby the title compound (605 mg) was yielded.
MS(FAB)m/z755(M+H)⁺
¹H-NMR(400 MHz, DMSO-d₆, 80° C.):
δ(ppm)0.85(3H, t, J=7.0 Hz), 1.27(3H, s), 1.29(3H, s), 1.33(9H, s), 1.71-1.81(2H, m), 1.83-2.06(2H, m), 2.23-2.39 (2H, m), 2.55-2.70(2H, m), 3.05-3.19(2H, m), 3.31-3.40(1H, m), 3.69-3.79(1H, m), 4.04(2H, t, J=5.0 Hz), 4.31-4.41(1H, m), 4.51-4.65(2H, m), 5.16(1H, d, J=15.5 Hz), 6.76(1H, dd, J=1.5, 5.0 Hz), 6.69(2H, m), 7.05-7.21(5H, m), 7.26-7.41 (3H, m), 7.55(1H, d, J=8.0 Hz), 7.79(1H, d, J=7.5 Hz).

Example 24(f)

Synthesis of tert-butyl 1-[(2R)-3-(1-isopropyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-2-methyl-1-oxopropan-2-ylcarbamate

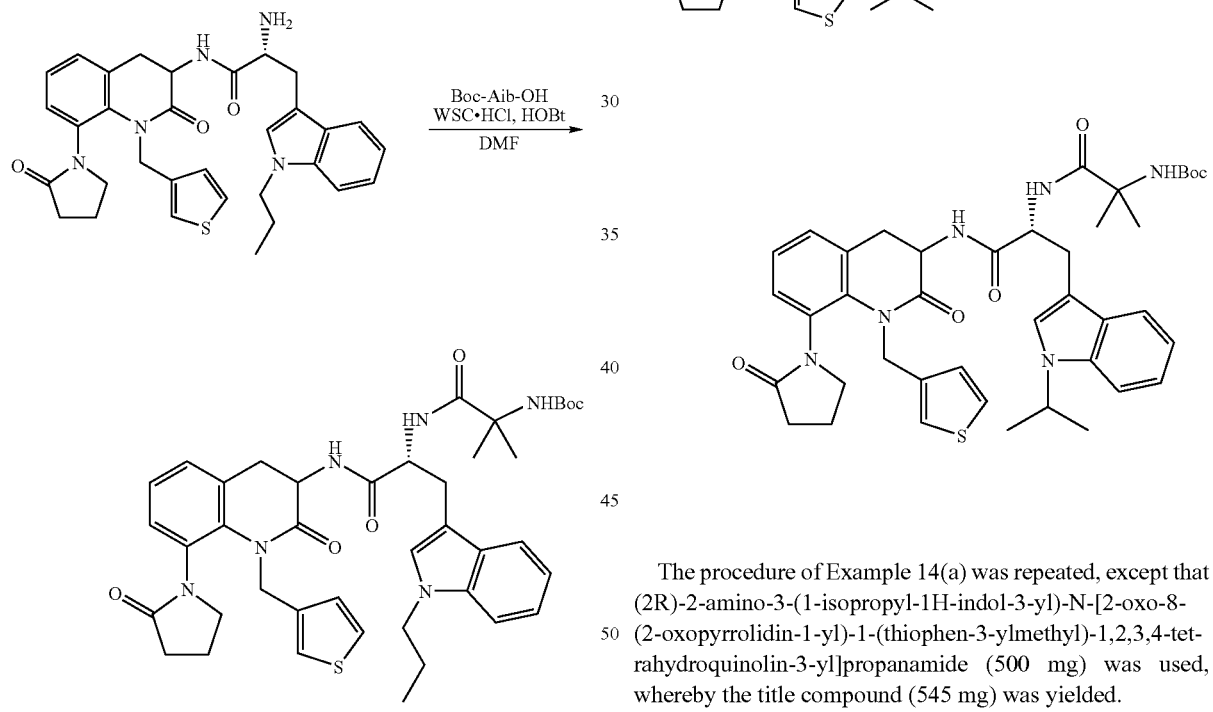

The procedure of Example 14(a) was repeated, except that (2R)-2-amino-3-(1-isopropyl-1H-indol-3-yl)-N-[2-oxo-8-(2-oxopyrrolidin-1-yl)-1-(thiophen-3-ylmethyl)-1,2,3,4-tetrahydroquinolin-3-yl]propanamide (500 mg) was used, whereby the title compound (545 mg) was yielded.

MS(FAB)m/z755(M+H)⁺

¹H-NMR(400 MHz, DMSO-d₆, 80° C.):
δ(ppm)1.27(3H, s), 1.29(3H, s), 1.33(9H, s), 1.43(3H, d, J=6.5 Hz), 1.43(3H, d, J=6.5 Hz), 1.80-2.06(2H, m), 2.23-2.39(2H, m), 2.50-2.70(2H, m), 3.05-3.20(2H, m), 3.31-3.40 (1H, m), 3.68-3.80(1H, m), 4.32-4.42(1H, m), 4.55(1H, d, J=15.5 Hz), 4.58-4.72(2H, m), 5.16(1H, d, J=15.5 Hz), 6.59 (1H, br s), 6.76(1H, dd, J=1.0, 5.0 Hz), 6.95-7.02(2H, m), 7.04-7.19(4H, m), 7.25-7.34(3H, m), 7.40(1H, d, J=8.5 Hz), 7.54(1H, d, J=8.0 Hz), 7.79(1H, d, J=7.5 Hz).

Example 24(g)

Synthesis of tert-butyl (2R)-2-methyl-1-[(2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-1-oxobutan-2-ylcarbamate

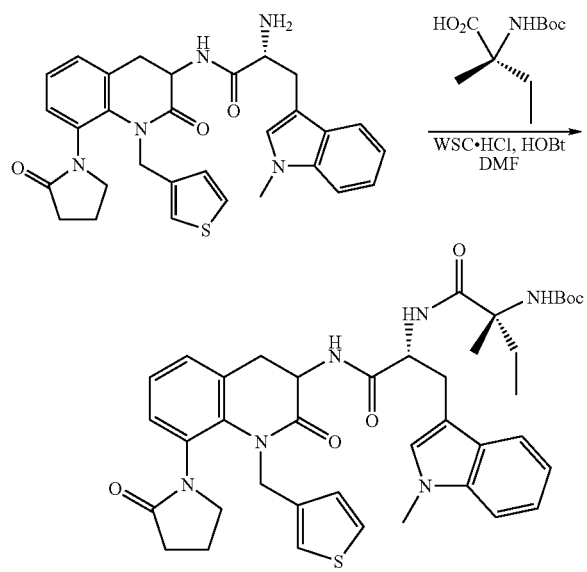

The procedure of Example 14(a) was repeated, except that (2R)-2-amino-3-(1-methyl-1H-indol-3-yl)-N-[2-oxo-8-(2-oxopyrrolidin-1-yl)-1-(thiophen-3-ylmethyl)-1,2,3,4-tetrahydroquinolin-3-yl]propanamide obtained in Example 8(b) (5.4 g) and (R)-2-(tert-butoxycarbonylamino)-2-methylbutanoic acid (2.4 g) were used, whereby the title compound (6.6 g) was yielded.

MS(FAB)m/z741(M+H)$^+$ $^1$H-NMR(400 MHz, DMSO-d$_6$):

δ(ppm)0.48(3H, t, J=7.5 Hz), 1.20(3H, s), 1.31(9H, s), 1.55-1.73(2H, m), 1.80-2.43(4H, m), 2.57-2.85(3H, m), 3.03-3.38(3H, m), 3.72(3H, s), 4.32-4.76(3H, m), 4.93-5.28(1H, m), 6.72-6.88(2H, m), 6.98-7.23(7H, m), 7.37(1H, d, J=8.0 Hz), 7.39-7.44(1H, m), 7.58(1H, d, J=8.0 Hz), 7.61-7.69(1H, m), 8.12-8.24(1H, m).

Example 24(h)

Synthesis of tert-butyl 2-methyl-1-[(2R)-4-methyl-1-oxo-1-[2-oxo-8-(2-oxopyrrolidin-1-yl)-1-(pyridin-2-ylmethyl)-1,2,3,4-tetrahydroquinolin-3-ylamino]pentan-2-ylamino]-1-oxopropan-2-ylcarbamate

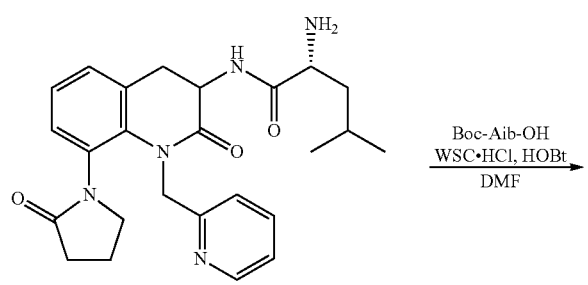

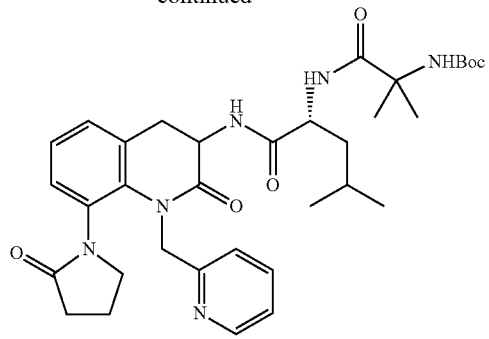

The procedure of Example 14(a) was repeated, except that (2R)-2-amino-4-methyl-N-[2-oxo-8-(2-oxopyrrolidin-1-yl)-1-(pyridin-2-ylmethyl)-1,2,3,4-tetrahydroquinolin-3-yl]pentanamide (130 mg) was used, whereby the title compound (110 mg) was yielded.

MS(FAB)m/z635(M+H)$^+$ $^1$H-NMR(400 MHz, DMSO-d$_6$):

δ(ppm)0.82(3H, d, J=6.0 Hz), 0.85(3H, d, J=6.0 Hz), 1.27(3H, s), 1.30(3H, s), 1.35(9H, s), 1.54-2.36(7H, m), 2.95(1H, dd, J=5.0, 14.5 Hz), 3.06(1H, t, J=14.5 Hz), 3.19-3.48(2H, m), 4.24-5.16(4H, m), 6.93-7.35(6H, m), 7.38-7.78(2H, m), 8.07-8.18(1H, m), 8.40-8.48(1H, m).

Example 25(a)

Synthesis of (2R)-2-(2-amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide

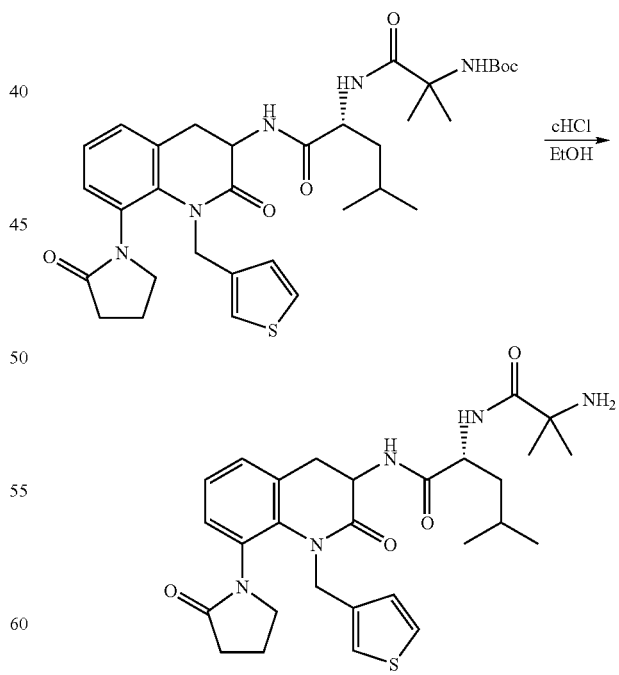

tert-Butyl 2-methyl-1-[(2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylamino]-1-oxopropan-2-ylcarbamate (2.8 g) was dissolved in ethanol (28 mL), and concentrated hydrochloric acid (7.5 mL) was added thereto. The mixture was heated at 70° C. while being stirred for 30 minutes, and then neutralized with saturated aqueous sodium bicarbonate solution under cooling on ice. Subsequently, the resultant mixture was extracted with chloroform and water, and the aqueous layer was further extracted with chloroform. The organic layers were combined. The combined organic layer was washed with saturated aqueous sodium chloride solution, and then dried over sodium sulfate. The solvent was evaporated under reduced pressure, whereby the title compound (2.30 g) was yielded.

MS(FAB)m/z540(M+H)+

¹H-NMR(400 MHz, DMSO-d₆, 80° C.):

δ(ppm)0.87(3H, d, J=6.5 Hz), 0.89(3H, d, J=6.5 Hz), 1.21 (6H, s), 1.49-2.09(7H, m), 2.24-2.39(2H, m), 2.77(1H, t, J=14.5 Hz), 2.94(1H, dd, J=5.0, 14.5 Hz), 3.35-3.44(1H, m), 3.70-3.80(1H, m), 4.32-4.46(2H, m), 4.59(1H, d, J=15.5 Hz), 5.16(1H, d, J=15.5 Hz), 6.79(1H, dd, J=1.0, 5.0 Hz), 7.01-7.05(1H, m), 7.10(1H, dd, J=6.5, 8.5 Hz), 7.13-7.20(3H, m), 7.32(1H, dd, J=3.0, 5.0 Hz), 7.93(1H, d, J=7.0 Hz).

Example 25(b)

Synthesis of 2-amino-2-methyl-N-[(2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]propanamide

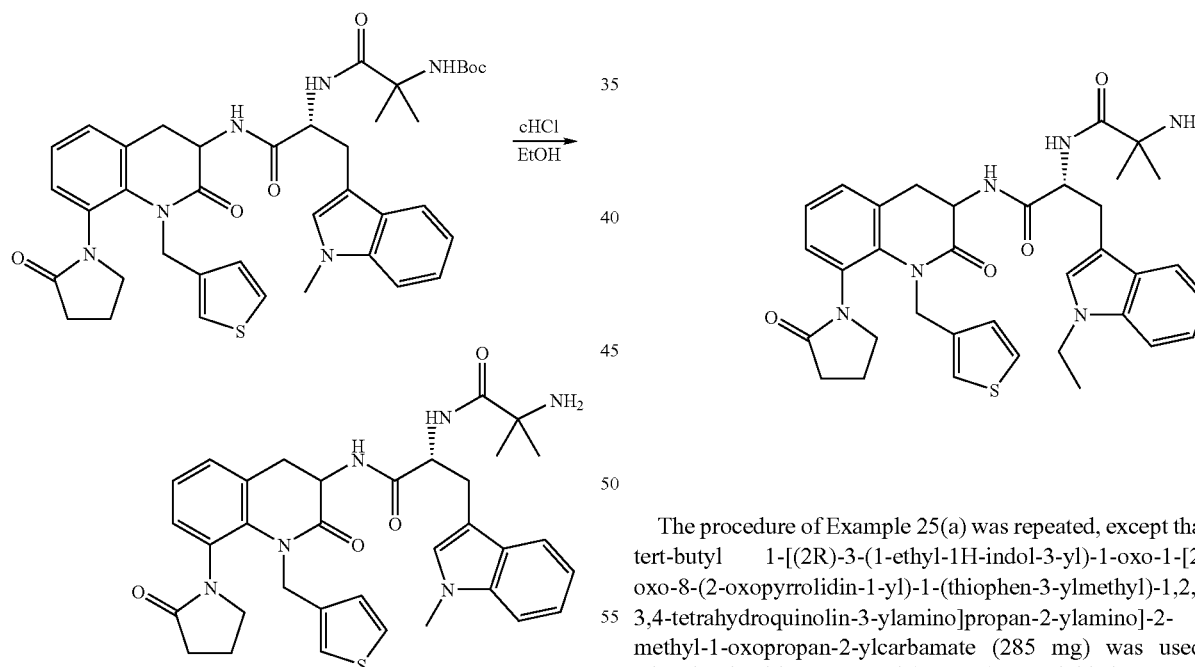

The procedure of Example 25(a) was repeated, except that tert-butyl 2-methyl-1-[(2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-1-oxopropan-2-ylcarbamate (480 mg) was used, whereby the title compound (343 mg) was yielded.

MS(FAB)m/z627(M+H)+

¹H-NMR(400 MHz, DMSO-d₆):

δ(ppm)1.11(3H, s), 1.15(3H, s), 1.82-2.45(6H, m), 2.54 (1H, dd, J=5.5, 10.0 Hz), 2.58-2.78(1H, m), 3.03-3.18(1H, m), 3.20-3.49(3H, m), 3.73(3H, s), 4.32-4.81(3H, m), 4.96-5.29(1H, m), 6.78(1H, d, J=5.0 Hz), 6.99-7.23(7H, m), 7.34-7.41(2H, m), 7.58(1H, d, J=8.0 Hz), 8.20(1H, d, J=7.0 Hz), 8.38(1H, d, J=8.0 Hz).

Example 25(c)

Synthesis of 2-amino-N-[(2R)-3-(1-ethyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-methylpropanamide

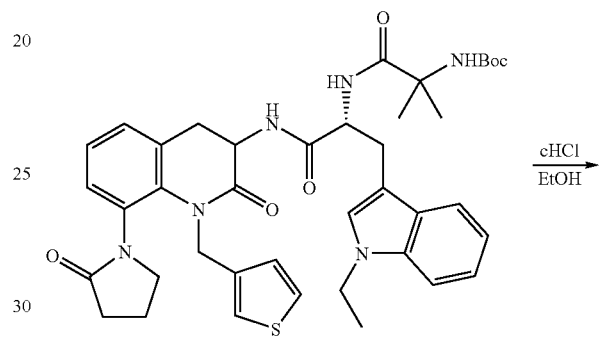

The procedure of Example 25(a) was repeated, except that tert-butyl 1-[(2R)-3-(1-ethyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-2-methyl-1-oxopropan-2-ylcarbamate (285 mg) was used, whereby the title compound (233 mg) was yielded.

MS(FAB)m/z641(M+H)+

¹H-NMR(400 MHz, DMSO-d₆):

δ(ppm)1.10(3H, s), 1.14(3H, s), 1.32(3H, t, J=7.0 Hz), 1.85-2.42(6H, m), 2.55-2.69(2H, m), 3.00-3.13(2H, m), 3.25-3.60(2H, m), 4.15(2H, q, J=7.0 Hz), 4.28-4.81(3H, m), 4.95-5.27(1H, m), 6.77(1H, d, J=5.0 Hz), 7.00(1H, t, J=7.0 Hz), 7.03-7.22(6H, m), 7.38-7.43(2H, m), 7.58(1H, d, J=8.0 Hz), 8.19(1H, br), 8.35(1H, d, J=8.0 Hz).

Example 25(d)

Synthesis of 2-amino-N-[(2R)-3-[1-(2-fluoroethyl)-1H-indol-3-yl]-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-methylpropanamide

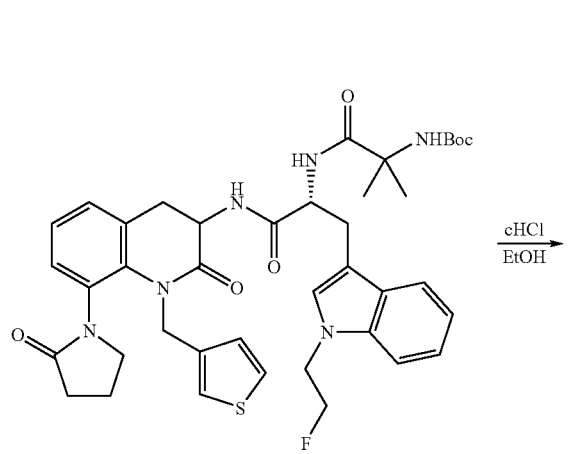

The procedure of Example 25(a) was repeated, except that tert-butyl 1-[(2R)-3-[1-(2-fluoroethyl)-1H-indol-3-yl]-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-2-methyl-1-oxopropan-2-ylcarbamate (316 mg) was used, whereby the title compound (239 mg) was yielded.

MS(FAB)m/z659(M+H)$^+$ $^1$H-NMR(400 MHz, DMSO-d$_6$, 80° C.):

δ(ppm)1.11(3H, s), 1.16(3H, s), 1.79-2.08(4H, m), 2.23-2.39(2H, m), 2.59(1H, t, J=14.0 Hz), 2.71(1H, dd, J=5.0, 15.0 Hz), 3.03-3.20(2H, m), 3.31-3.42(1H, m), 3.67-3.79(1H, m), 4.30-4.48(3H, m), 4.50-4.67(3H, m), 4.69-4.78(1H, m), 5.14(1H, d, J=15.5 Hz), 6.72-6.80(1H, m), 6.93-7.21(8H, m), 7.27-7.34(1H, m), 7.40(1H, d, J=8.0 Hz), 7.58(1H, d, J=8.0 Hz), 7.84(1H, d, J=7.0 Hz).

Example 25(e)

Synthesis of 2-amino-2-methyl-N-[(2R)-1-oxo-1-[2-oxo-8-(2-oxopyrrolidin-1-yl)-1-(thiophen-3-ylmethyl)-1,2,3,4-tetrahydroquinolin-3-ylamino]-3-(1-propyl-1H-indol-3-yl)propan-2-yl]propanamide

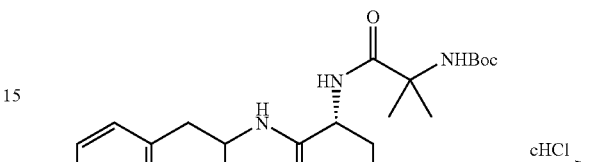

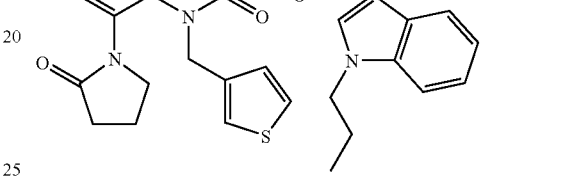

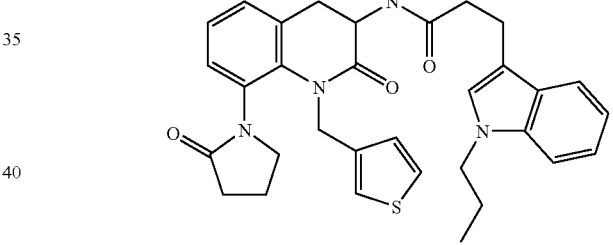

The procedure of Example 25(a) was repeated, except that tert-butyl 2-methyl-1-oxo-1-[(2R)-1-oxo-1-[2-oxo-8-(2-oxopyrrolidin-1-yl)-1-(thiophen-3-ylmethyl)-1,2,3,4-tetrahydroquinolin-3-ylamino]-3-(1-propyl-1H-indol-3-yl)propan-2-ylamino]propan-2-ylcarbamate (499 mg) was used, whereby the title compound (406 mg) was yielded.

MS(FAB)m/z655(M+H)$^+$ $^1$H-NMR(400 MHz, DMSO-d$_6$, 80° C.):

δ(ppm)0.84(3H, t, J=7.5 Hz), 1.11(3H, s), 1.16(3H, s), 1.71-1.81(2H, m), 1.82-2.06(4H, m), 2.23-2.39(2H, m), 2.58(1H, t, J=14.5 Hz), 2.71(1H, dd, J=5.0, 14.5 Hz), 3.05-3.18(2H, m), 3.32-3.41(1H, m), 3.68-3.79(1H, m), 4.05(2H, t, J=7.0 Hz), 4.34-4.41(1H, m), 4.52-4.64(2H, m), 5.14(1H, d, J=16.0 Hz), 6.77(1H, dd, J=1.0, 5.0 Hz), 6.94-7.03(6H, m), 7.30-7.39(2H, m), 7.56(1H, d, J=8.0 Hz), 7.85(1H, d, J=7.0 Hz).

Example 25(f)

Synthesis of 2-amino-N-[(2R)-3-(1-isopropyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-methylpropanamide

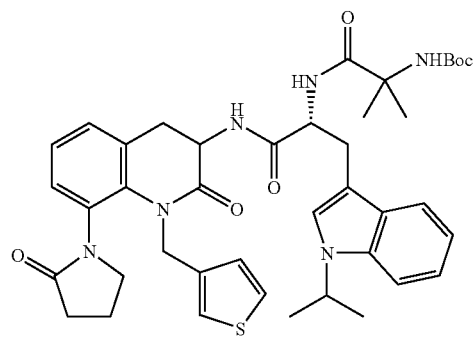
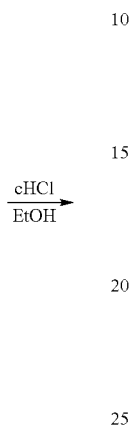
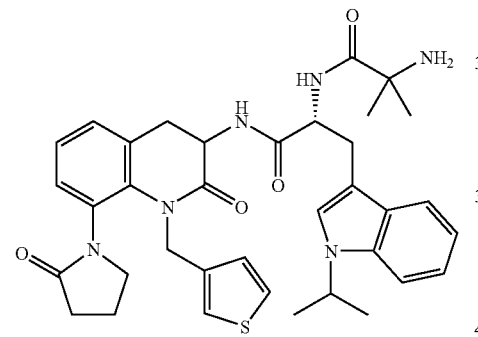

The procedure of Example 25(a) was repeated, except that tert-butyl 1-[(2R)-3-(1-isopropyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-2-methyl-1-oxopropan-2-ylcarbamate (500 mg) was used, whereby the title compound (368 mg) was yielded.

MS(FAB)m/z655(M+H)+

1H-NMR(400 MHz, DMSO-$d_6$, 80° C.):
δ(ppm)1.12(3H, s), 1.17(3H, s), 1.43(3H, d, J=6.5 Hz), 1.43(3H, d, J=6.5 Hz), 1.81-2.06(4H, m), 2.23-2.38(3H, m), 2.52-2.75(2H, m), 3.11(2H, dq, J=14.5, 7.5 Hz), 3.33-3.42 (1H, m), 3.69-3.80(1H, m), 4.32-4.42(1H, m), 4.56(1H, d, J=15.5 Hz), 4.60-4.72(2H, m), 5.15(1H, d, J=15.5 Hz), 6.76 (1H, dd, J=1.0, 5.0 Hz), 6.95-7.02(2H, m), 7.05-7.18(4H, m), 7.25(1H, s), 7.32(1H, dd, J=3.0, 5.0 Hz), 7.40(1H, d, J=8.5 Hz), 7.56(1H, d, J=8.0 Hz), 7.86(1H, d, J=7.0 Hz).

Example 25(g)

Synthesis of (2R)-2-amino-2-methyl-N-[(2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]butanamide

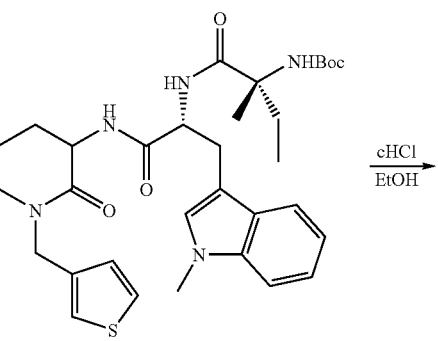

The procedure of Example 25(a) was repeated, except that tert-butyl (2R)-2-methyl-1-[(2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-1-oxobutan-2-ylcarbamate (8.8 g) was used, whereby the title compound (8.6 g) was yielded.

MS(FAB)m/z641(M+H)+

1H-NMR(400 MHz, DMSO-$d_6$):
δ(ppm)0.56(3H, t, J=7.5 Hz), 1.09(3H, s), 1.22-1.35(2H, m), 1.51-1.63(1H, m), 1.80-2.75(9H, m), 2.98-3.12(2H, m), 3.72(3H, s), 4.28-4.77(3H, m), 4.93-5.23(1H, m), 6.78(1H, d, J=5.0 Hz), 6.97-7.22(7H, m), 7.37(1H, d, J=8.0 Hz), 7.39-7.44(1H, m), 7.60(1H, d, J=8.0 Hz), 8.12-8.24(1H, m), 8.37 (1H, d, J=8.0 Hz).

Example 25(h)

Synthesis of (2R)-2-((S)-2-aminopropanamido)-4-methyl-N-[2-oxo-8-(2-oxopyrrolidin-1-yl)-1-(thiophen-3-ylmethyl)-1,2,3,4-tetrahydroquinolin-3-yl]pentanamide

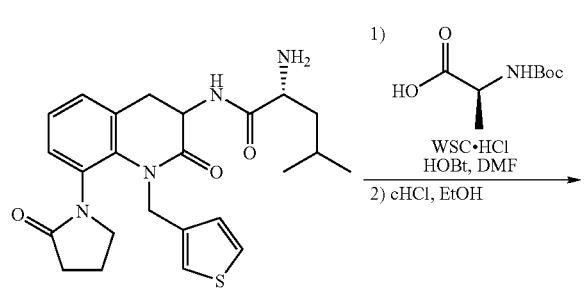

Example 25(i)

Synthesis of (2R)-2-((R)-2-aminopropanamido)-4-methyl-N-[2-oxo-8-(2-oxopyrrolidin-1-yl)-1-(thiophen-3-ylmethyl)-1,2,3,4-tetrahydroquinolin-3-yl]pentanamide

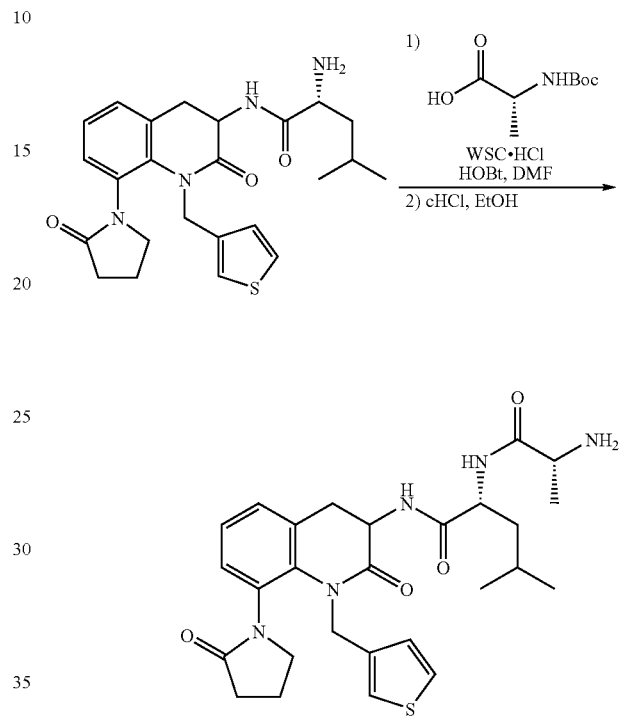

The procedure of Example 14(a) was repeated, except that (2R)-2-amino-4-methyl-N-[2-oxo-8-(2-oxopyrrolidin-1-yl)-1-(thiophen-3-ylmethyl)-1,2,3,4-tetrahydroquinolin-3-yl]pentanamide (600 mg) and (S)-2-(tert-butoxycarbonylamino)propanoic acid (279 mg) were used, whereby tert-butyl (2S)-1-[(2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylamino]-1-oxopropan-2-ylcarbamate (688 mg) was yielded. Subsequently, the procedure of Example 25(a) was repeated, except that the compound prepared as described above was used, whereby the title compound (455 mg) was yielded.

MS(FAB)m/z526(M+H)$^+$ $^1$H-NMR(400 MHz, DMSO-d$_6$, 80° C.):

δ(ppm)0.88(6H, dd, J=6.59 Hz), 1.14(3H, d, J=7 Hz), 1.54 (2H, m), 1.61(2H, m), 1.9-2.0(2H, m), 2.30(2H, m), 2.78(1H, t, J=14 Hz), 2.91(1H, dd, J=5.15 Hz), 3.31 (1H, m), 3.39(1H, m), 3.75(1H, br s), 4.39(2H, m), 4.59(1H, d, J=15.5 Hz), 5.16(1H, d, J=15.5 Hz), 6.80(1H, d, J=5 Hz), 7.03(1H, br s), 7.12(1H, dd, J=7, 8.5 Hz), 7.17(2H, m), 7.33(1H, m), 7.91 (1H, d, J=7H z).

The procedure of Example 14(a) was repeated, except that (2R)-2-amino-4-methyl-N-[2-oxo-8-(2-oxopyrrolidin-1-yl)-1-(thiophen-3-ylmethyl)-1,2,3,4-tetrahydroquinolin-3-yl]pentanamide (600 mg) and (R)-2-(tert-butoxycarbonylamino)propanoic acid (279 mg) were used, whereby tert-butyl (2R)-1-[(2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylamino]-1-oxopropan-2-ylcarbamate (832 mg) was yielded. Subsequently, the procedure of Example 25(a) was repeated, except that the compound prepared as described above was used, whereby the title compound (460 mg) was yielded.

MS(FAB)m/z526(M+H)$^+$ $^1$H-NMR(400 MHz, DMSO-d$_6$, 80° C.):

δ(ppm)0.88(6H, t, J=7 Hz), 1.15(3H, d, J=14 Hz), 1.53(2H, m), 1.61(1H, m), 1.85-2.05(2H, m), 2.30(2H, m), 2.78(1H, t, J=14 Hz), 2.94(1H, dd, J=5.15 Hz), 3.30(1H, m), 3.39(1H, m), 4.40(2H, m), 4.59(1H, d, J=15.5 Hz), 5.15(1H, d, J=15.5 Hz), 6.99(1H, d, J=5 Hz), 7.13(1H, br s), 7.10(1H, m), 7.16 (1H, d, J=7 Hz), 7.33(1H, m), 7.92(1H, d, J=7 Hz).

Example 25(j)

Synthesis of (2R)-2-((S)-2-amino-2-methylbutanamido)-4-methyl-N-[2-oxo-8-(2-oxopyrrolidin-1-yl)-1-(thiophen-3-ylmethyl)-1,2,3,4-tetrahydroquinolin-3-yl]pentanamide

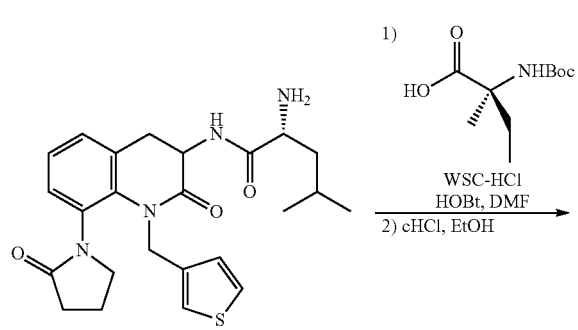

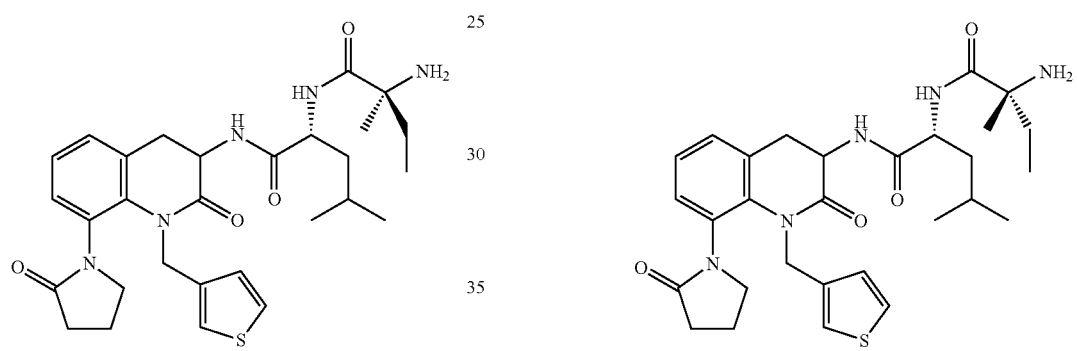

Example 25(k)

Synthesis of (2R)-2-((R)-2-amino-2-methylbutanamido)-4-methyl-N-[2-oxo-8-(2-oxopyrrolidin-1-yl)-1-(thiophen-3-ylmethyl)-1,2,3,4-tetrahydroquinolin-3-yl]pentanamide

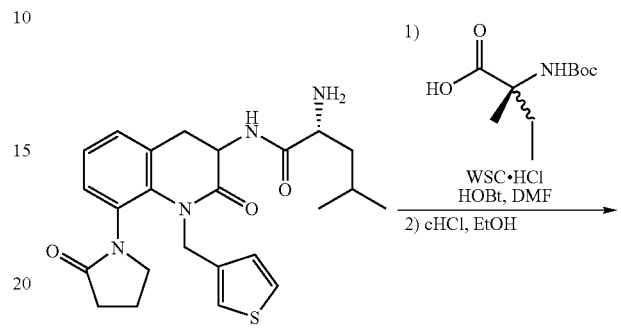

The procedure of Example 14(a) was repeated, except that (2R)-2-amino-4-methyl-N-[2-oxo-8-(2-oxopyrrolidin-1-yl)-1-(thiophen-3-ylmethyl)-1,2,3,4-tetrahydroquinolin-3-yl]pentanamide (600 mg) and (S)-2-(tert-butoxycarbonylamino)-2-methylbutanoic acid (320 mg) were used, whereby tert-butyl (2S)-2-methyl-1-[(2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylamino]-1-oxobutan-2-ylcarbamate (881 mg) was yielded. Subsequently, the procedure of Example 25(a) was repeated, except that the compound prepared as described above was used, whereby the title compound (241 mg) was yielded.

MS(FAB)m/z554(M+H)$^+$ $^1$H-NMR(400 MHz, DMSO-d$_6$, 80° C.):

δ(ppm)0.78(3H, t, J=7 Hz), 0.87(6H, d, J=6.5 Hz), 1.15 (3H, s), 1.44(1H, m), 1.54(2H, m), 1.63(3H, m), 1.85-2.05 (3H, m), 2.30(2H, m), 2.74(1H, t, J=14 Hz), 2.94(1H, dd, J=5.15 Hz), 3.38(1H, m), 3.76(1H, m), 4.38(2H, m), 4.58(1H, d, J=15.5 Hz), 5.16(1H, d, J=15.5 Hz), 6.78(1H, d, J=5 Hz), 7.03(1H, br, s), 7.11(1H, m), 7.18(2H, m), 7.33(1H, m), 7.91 (1H, d, J=7 Hz).

The procedure of Example 14(a) was repeated, except that (2R)-2-amino-4-methyl-N-[2-oxo-8-(2-oxopyrrolidin-1-yl)-1-(thiophen-3-ylmethyl)-1,2,3,4-tetrahydroquinolin-3-yl] pentanamide (600 mg) and (R)-2-(tert-butoxycarbonylamino)-2-methylbutanoic acid (320 mg) were used, whereby tert-butyl (2R)-2-methyl-1-[(2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylamino]-1-oxobutan-2-ylcarbamate (844 mg) was yielded. Subsequently, the procedure of Example 25(a) was repeated, except that the compound prepared as described above was used, whereby the title compound (528 mg) was yielded.

MS(FAB)m/z554(M+H)$^+$ $^1$H-NMR(400 MHz, DMSO-d$_6$, 80° C.):

δ(ppm)0.79(3H, t, J=15 Hz), 0.88(6H, t, J=15 Hz), 1.16 (3H, s), 1.19(1H, d, J=14 Hz), 1.43(1H, m), 1.54(2H, m), 1.64(3H, m), 1.85-2.05(3H, m), 2.30(2H, m), 2.77(1H, t, J=14 Hz), 2.94(1H, m), 3.39(1H, m), 3.75(1H, m), 4.39(2H, m), 4.58(1H, d, J=16 Hz), 5.16(1H, d, J=16 Hz), 6.79(1H, d, J=5 Hz), 7.13(1H, br s), 7.10(1H, dd, J=6.9 Hz), 7.17(1H, d, J=7 Hz), 7.33(1H, dd, J=3.5 Hz), 7.95(1H, d, J=7 Hz).

Example 25(l)

Synthesis of N-[(2R)-3-(1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-amino-2-methylpropanamide

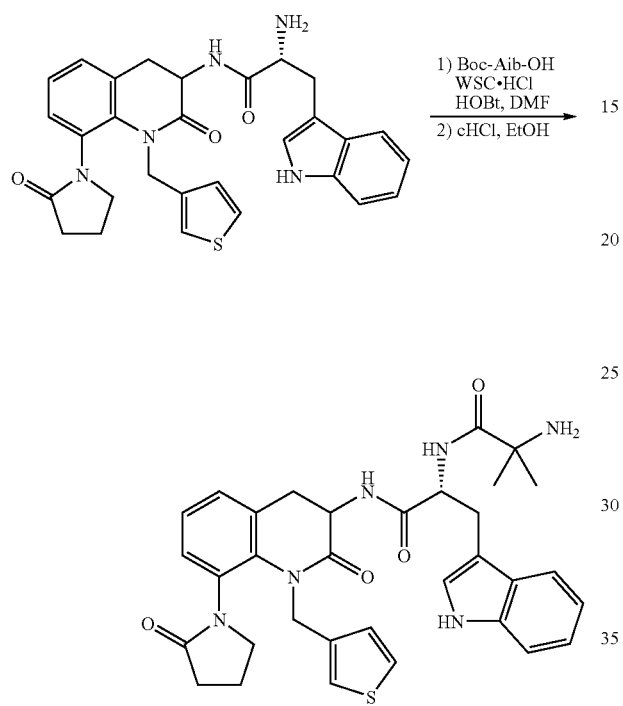

The procedure of Example 14(a) was repeated, except that (2R)-2-amino-3-(1H-indol-3-yl)-N-[2-oxo-8-(2-oxopyrrolidin-1-yl)-1-(thiophen-3-ylmethyl)-1,2,3,4-tetrahydroquinolin-3-yl]propanamide (402 mg) was used, whereby tert-butyl 1-[(2R)-3-(1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-ylamino]-2-methyl-1-oxopropan-2-ylcarbamate was yielded. Subsequently, the procedure of Example 25(a) was repeated, except that the compound prepared as described above was used, whereby the title compound (300 mg) was yielded.

MS(FAB)m/z613(M+H)$^+$ $^1$H-NMR(400 MHz, DMSO-d$_6$, 80° C.):

δ(ppm)1.10(3H, s), 1.16(3H, s), 1.31-2.02(4H, m), 2.26-2.34(2H, m), 2.59(1H, dd, J=13.0 Hz), 2.72(1H, dd, J=5.0, 10.0 Hz), 3.08-3.18(2H, m), 3.34-3.40(1H, m), 3.73-3.74 (1H, m), 4.34-4.40(1H, m), 4.54-4.62(2H, m), 5.14(1H, d, J=15.5 Hz), 6.76(1H, d, J=5.0 Hz), 6.93-7.17(7H, m), 7.31-7.33(2H, m), 7.54(1H, d, J=8.0 Hz), 7.84(1H, d, J=7.0 Hz), 8.20(1H, s), 10.16 (1H, s).

Example 25(m)

Synthesis of (2R)-2-(2-amino-2-methylpropanamido)-4-methyl-N-[2-oxo-8-(2-oxopyrrolidin-1-yl)-1-(pyridin-2-ylmethyl)-1,2,3,4-tetrahydroquinolin-3-yl]pentanamide

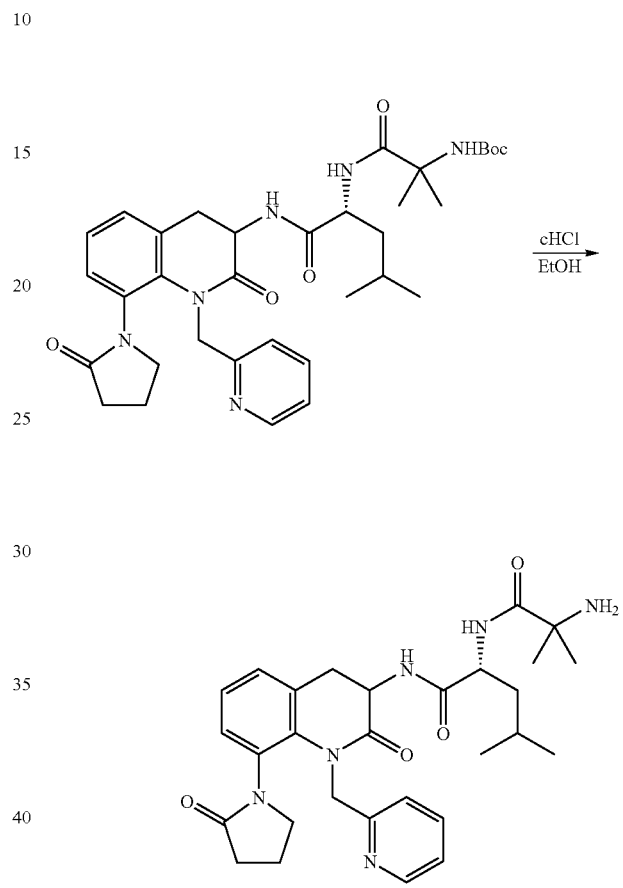

The procedure of Example 25(a) was repeated, except that tert-butyl 2-methyl-1-[(2R)-4-methyl-1-oxo-1-[2-oxo-8-(2-oxopyrrolidin-1-yl)-1-(pyridin-2-ylmethyl)-1,2,3,4-tetrahydroquinolin-3-ylamino]pentan-2-ylamino]-1-oxopropan-2-ylcarbamate (100 mg) was used, whereby the title compound (74 mg) was yielded.

MS(FAB)m/z535(M+H)$^+$ $^1$H-NMR(400 MHz, DMSO-d$_6$):

δ(ppm)0.87(3H, d, J=6.5 Hz), 0.89(3H, d, J=6.5 Hz), 1.17 (3H, s), 1.17(3H, s), 1.43-1.63(3H, m), 1.70-2.34(6H, m), 2.94(1H, dd, J=5.0, 14.5 Hz), 3.07(1H, t, J=14.5 Hz), 3.15-3.52(2H, m), 4.15-5.20(4H, m), 7.03-7.35(5H, m), 7.63-7.75 (1H, m), 7.98-8.14(1H, m), 8.40-8.53(2H, m).

Example 26

Synthesis of tert-butyl 1-(1-(8-amino-2-oxo-1,2,3,4-tetrahydroquinolin-3-ylamino)-4-methyl-1-oxopentan-2-ylamino)-2-methyl-1-oxopropan-2-ylcarbamate

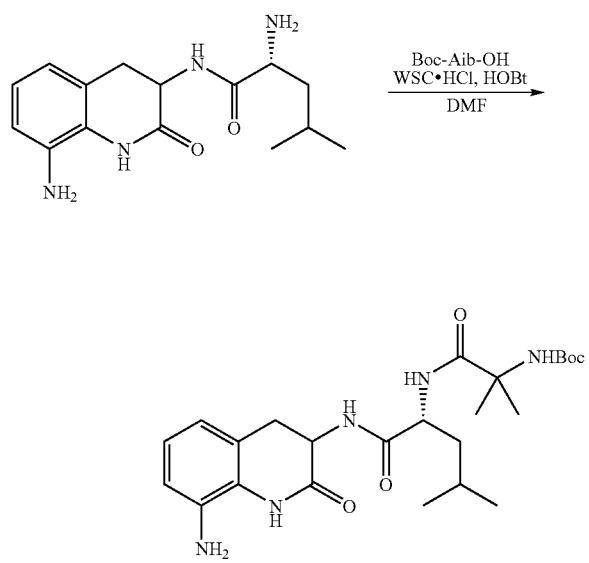

The procedure of Example 14(a) was repeated, except that N-tert-butoxycarbonyl-aminoisobutyric acid (554 mg) was used, whereby the title compound (1.1 g) was yielded.

MS(FAB)m/z476(M+H)$^+$ $^1$H-NMR(400 MHz, DMSO-d$_6$):

δ(ppm)0.83(3H, d, J=6.5 Hz), 0.86(3H, d, J=6.5 Hz), 1.28 (3H, s), 1.30(3H, s), 1.36(9H, s), 1.43-1.69(3H, m), 2.76-2.88 (2H, m), 4.29-4.40(2H, m), 5.05(2H, s), 6.42(1H, d, J=7.0 Hz), 6.54(1H, d, J=7.0 Hz), 6.69 (1H, t, J=8.0 Hz), 7.04(1H, br), 7.61(1H, d, J=6.0 Hz), 8.01(1H, d, J=5.0 Hz), 8.31(1H, s).

Example 27

Synthesis of tert-butyl 1-[(2R)-1-[8-(4-chlorobutanamido)-2-oxo-1,2,3,4-tetrahydroquinolin-3-ylamino]-4-methyl-1-oxopentan-2-ylamino]-2-methyl-1-oxopropan-2-ylcarbamate

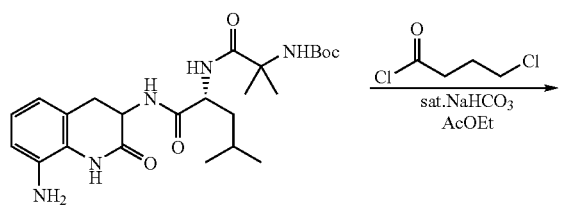

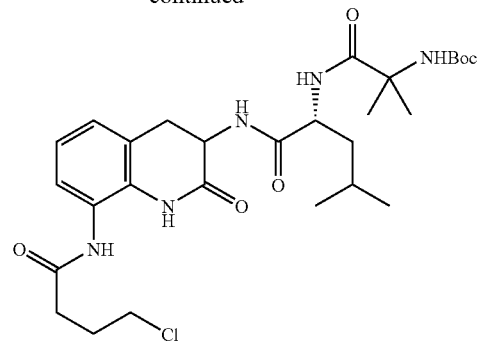

The procedure of Example 20 was repeated, except that tert-butyl 1-[(2R)-1-[8-amino-2-oxo-1,2,3,4-tetrahydroquinolin-3-ylamino]-4-methyl-1-oxopentan-2-ylamino]-2-methyl-1-oxopropan-2-ylcarbamate (8.2 g) was used, whereby the title compound (10.3 g) was yielded.

MS(FAB)m/z581(M+H)$^+$ $^1$H-NMR(400 MHz, DMSO-d$_6$):

δ(ppm)0.83(3H, d, J=6.5 Hz), 0.87(3H, d, J=6.5 Hz), 1.29 (3H, s), 1.31(3H, s), 1.36(9H, s), 1.4 4-1.72(3H, m), 1.98-2.08(2H, m), 2.48-2.58(2H, m), 2.85-3.06(2H, m), 3.71(2H, t, J=6.5 Hz), 4.24-4.48(2H, m), 6.94(1H, t, J=7.5 Hz), 6.98-7.15(2H, m), 7.32(1H, d, J=8.0 Hz), 7.52-7.69(1H, m), 8.02-8.20(1H, m), 9.35(1H, s), 9.69(1H, s).

Example 28

Synthesis of tert-butyl 2-methyl-1-[(2R)-4-methyl-1-oxo-1-[2-oxo-8-(2-oxopyrrolidin-1-yl)-1,2,3,4-tetrahydroquinolin-3-ylamino]pentan-2-ylamino]-1-oxopropan-2-ylcarbamate

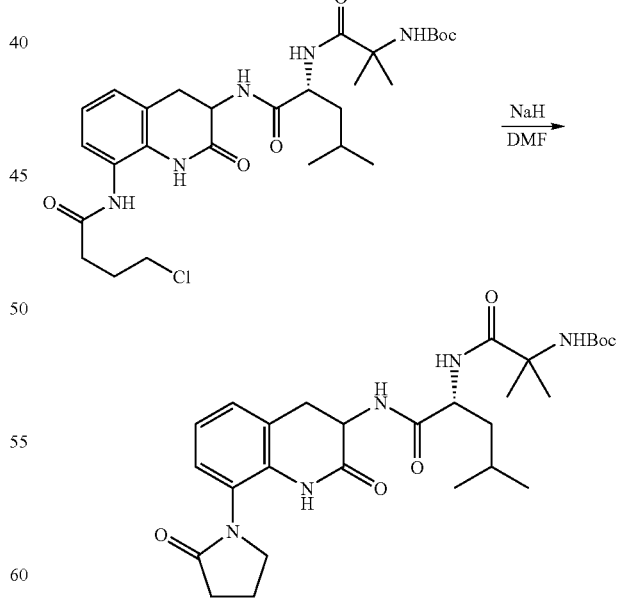

The procedure of Example 21 was repeated, except that tert-butyl 1-[(2R)-1-[8-(4-chlorobutanamido)-2-oxo-1,2,3,4-tetrahydroquinolin-3-ylamino]-4-methyl-1-oxopentan-2-ylamino]-2-methyl-1-oxopropan-2-ylcarbamate (10.0 g) was used, whereby the title compound (7.05 g) was yielded.

MS(FAB)m/z544(M+H)+

¹H-NMR(400 MHz, DMSO-d₆):

δ(ppm)0.83(3H, d, J=6.0 Hz), 0.87(3H, d, J=6.0 Hz), 1.28 (3H, s), 1.31(3H, s), 1.36(9H, s), 1.44-1.72(3H, m), 2.08-2.19(2H, m), 2.40(2H, t, J=8.0 Hz), 2.92(1H, t, J=15.0 Hz), 3.01(1H, dd, J=6.5, 15.0 Hz), 3.55-3.74(2H, m), 4.25-4.48 (2H, m), 6.99(1H, t, J=8.0 Hz), 7.06(1H, br s), 7.11(1H, d, J=8.0 Hz), 7.18(1H, d, J=8.0 Hz), 7.52-7.71(1H, m), 8.00-8.16(1H, m), 9.77(1H, s).

Example 29

Synthesis of tert-butyl 2-methyl-1-[(2R)-4-methyl-1-oxo-1-[2-oxo-8-(2-oxopyrrolidin-1-yl)-1-(thiophen-2-ylmethyl)-1,2,3,4-tetrahydroquinolin-3-ylamino]pentan-2-ylamino]-1-oxopentan-2-ylcarbamate

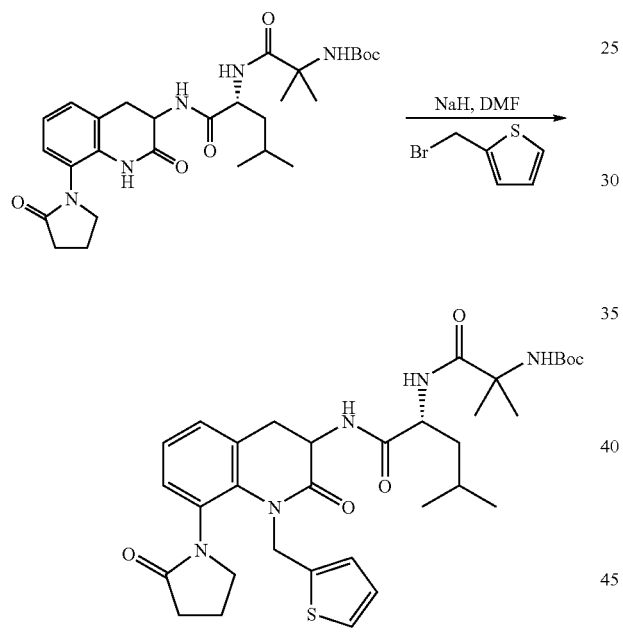

The procedure of Example 8 was repeated, except that tert-butyl 2-methyl-1-[(2R)-4-methyl-1-oxo-1-[2-oxo-8-(2-oxopyrrolidin-1-yl)-1,2,3,4-tetrahydroquinolin-3-ylamino]pentan-2-ylamino]-1-oxopentan-2-ylcarbamate (3.0 g) was used, whereby the title compound (3.73 g) was yielded.

MS(FAB)m/z640(M+H)+

¹H-NMR(400 MHz, DMSO-d₆):

δ(ppm)0.83(3H, d, J=6.0 Hz), 0.86(3H, d, J=6.0 Hz), 1.29 (3H, s), 1.31(3H, s), 1.35(9H, s), 1.40-1.72(3H, m), 1.74-2.48 (4H, m), 2.65-2.79(1H, m), 2.82-2.88(1H, m), 3.23-3.75(2H, m), 4.25-4.82(3H, m), 5.30-5.61(1H, m), 6.77(1H, br s), 6.82-6.88(1H, m), 6.93-7.08(1H, br s), 7.13(1H, t, J=7.5 Hz), 7.22 (2H, t, J=7.5 Hz), 7.32(1H, d, J=5.0 Hz), 7.53-7.71(1H, m), 8.10-8.25(1H, m).

Example 30

Synthesis of (2R)-2-(2-amino-2-methylpropanamido)-4-methyl-N-[2-oxo-8-(2-oxopyrrolidin-1-yl)-1-(thiophen-2-ylmethyl)-1,2,3,4-tetrahydroquinolin-3-yl]pentanamide

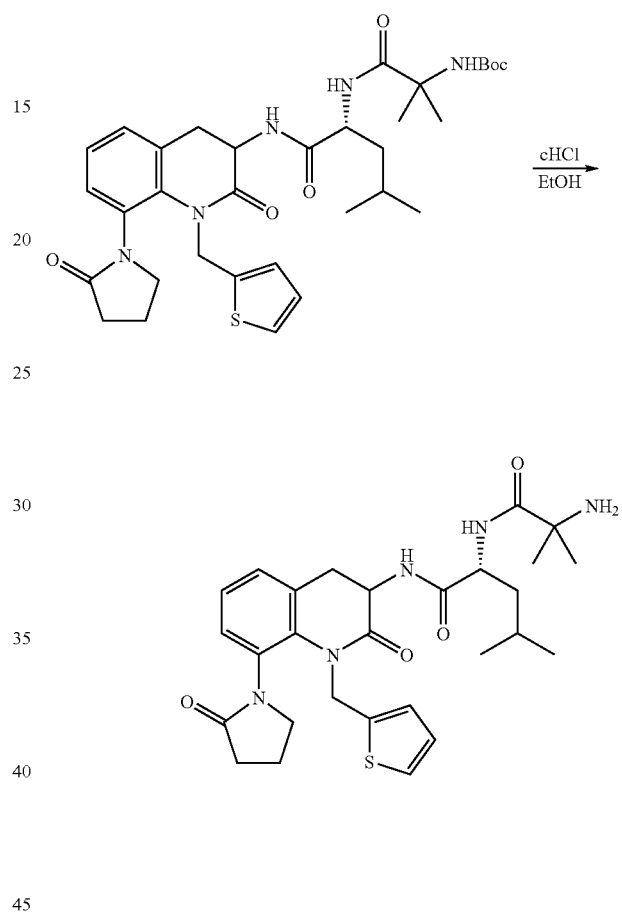

The procedure of Example 25(a) was repeated, except that tert-butyl 2-methyl-1-[(2R)-4-methyl-1-oxo-1-[2-oxo-8-(2-oxopyrrolidin-1-yl)-1-(thiophen-2-ylmethyl)-1,2,3,4-tetrahydroquinolin-3-ylamino]pentan-2-ylamino]-1-oxopentan-2-ylcarbamate (3.50 g) was used, whereby the title compound (2.02 g) was yielded.

MS(FAB)m/z640(M+H)+

¹H-NMR(400 MHz, DMSO-d₆):

δ(ppm)0.87(3H, d, J=6.0 Hz), 0.89(3H, d, J=6.0 Hz), 1.19 (6H, s), 1.43-1.67(3H, m), 1.68-2.28(4H, m), 2.29-2.50(2H, m), 2.73(1H, t, J=14.5 Hz), 2.86(1H, dd, J=5.0, 14.5 Hz), 3.20-3.80(2H, m), 4.32-4.90(3H, m), 5.18-5.61(1H, m), 6.78 (1H, br s), 6.84-6.91(1H, m), 7.13(1H, t, J=7.5 Hz), 7.17-7.29 (2H, m), 7.33(1H, d, J=5.0 Hz), 7.96-8.18(1H, br s), 8.49(1H, d, J=7.5 Hz).

Example 31

Synthesis of tert-butyl 1-((2R)-1-(8-amino-2-oxo-1-(pyridin-2-ylmethyl)-1,2,3,4-tetrahydroquinolin-3-ylamino)-4-methyl-1-oxopentan-2-ylamino)-2-methyl-1-oxopropan-2-ylcarbamate

Example 32

Synthesis of tert-butyl 1-((2R)-1-(8-(ethylamino)-2-oxo-1-(pyridin-2-ylmethyl)-1,2,3,4-tetrahydroquinolin-3-ylamino)-4-methyl-1-oxopentan-2-ylamino)-2-methyl-1-oxopropan-2-ylcarbamate

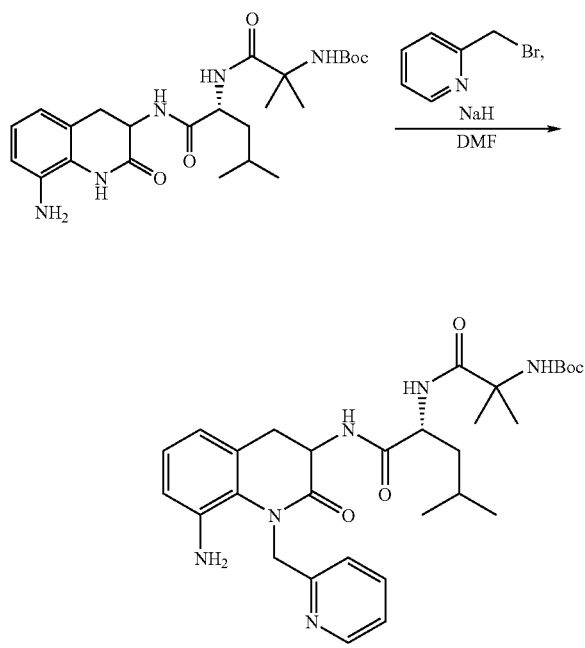

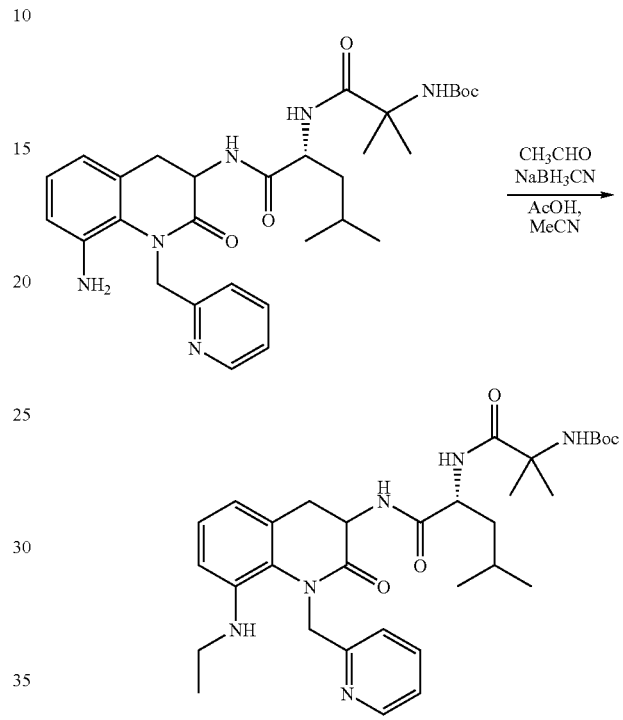

tert-Butyl 1-(1-(8-amino-2-oxo-1,2,3,4-tetrahydroquinolin-3-ylamino)-4-methyl-1-oxopentan-2-ylamino)-2-methyl-1-oxopropan-2-ylcarbamate (1.04 g) and 2-(bromomethyl)pyridine hydrobromide (553 mg) were sequentially added to N,N-dimethylformaldehyde (7.5 mL), and sodium hydride (174 mg) was added in two portions to the mixture under cooling on ice, followed by stirring for two hours. The resultant mixture was extracted with ethyl acetate and water, and the aqueous layer was further extracted with ethyl acetate. The organic layers were combined, and the combined organic layer was dried over sodium sulfate. The solvent was evaporated under reduced pressure, and the thus-recovered residue was purified through silica gel column chromatography (hexane:ethyl acetate=1:2), whereby the title compound (393 mg) was yielded.

MS(FAB)m/z567(M+H)$^+$ $^1$H-NMR(400 MHz, DMSO-d$_6$):

δ(ppm)0.80(3H, d, J=6.5 Hz), 0.83(3H, d, 6.5 Hz), 1.25 (3H, s), 1.28(3H, s), 1.34(9H, s), 1.40-1.45(1H, m), 1.50-1.66 (2H, m), 2.72(1H, dd, J=5.0, 10.0 Hz), 2.94(1H, t, J=14.0 Hz), 4.24-4.33(2H, m), 4.95(1H, d, J=15.5 Hz), 5.06(1H, d, J=15.5 Hz), 5.51(2H, s), 6.51(1H, d, J=7.5 Hz), 6.66(1H, d, J=8.0 Hz), 6.82(1H, t, J=8.0 Hz), 6.99 (1H, br), 7.23(1H, dd, J=2.0, 5.0 Hz), 7.31(1H, d, J=8.0 Hz), 7.53-7.61(1H, m), 7.71-7.75 (1H, m), 7.98-8.03(1H, m), 8.44(1H, d, J=10.0 Hz).

tert-Butyl 1-((2R)-1-(8-amino-2-oxo-1-(pyridin-2-ylmethyl)-1,2,3,4-tetrahydroquinolin-3-ylamino)-4-methyl-1-oxopentan-2-ylamino)-2-methyl-1-oxopropan-2-ylcarbamate (59 mg) and acetaldehyde (29 μL) were sequentially added to acetonitrile (730 μL), and sodium cyanoborohydride (7 mg) and acetic acid (18 μL) were added to the mixture under cooling on ice, followed by stirring for 5 minutes. The resultant mixture was extracted with ethyl acetate and saturated aqueous sodium bicarbonate solution, and the aqueous layer was further extracted with ethyl acetate. The organic layers were combined, and the combined organic layer was washed with saturated aqueous sodium chloride solution, followed by drying over sodium sulfate. The solvent was evaporated under reduced pressure, and the thus-recovered residue was purified through silica gel column chromatography (hexane:ethyl acetate=1:1), whereby the title compound (58 mg) was yielded.

MS(FAB)m/z595(M+H)$^+$ $^1$H-NMR(400 MHz, DMSO-d$_6$):

δ(ppm)0.79(3H, d, J=6.5 Hz), 0.83(3H, d, J=6.5 Hz), 1.10 (3H, t, J=7.0 Hz), 1.25(3H, s), 1.28(3H, s), 1.35(9H, s), 1.39-1.45(1H, m), 1.50-1.66(2H, m), 2.74(1H, dd, J=5.0, 10.0 Hz), 2.88-3.10(3H, m), 4.22-4.32(2H, m), 4.89(2H, s), 6.35(1H, br), 6.56(1H, d, J=7.5 Hz), 6.61(1H, d, J=8.0 Hz), 6.92-7.03 (2H, m), 7.27(1H, dd, J=2.0, 5.0 Hz), 7.35(1H, d, J=8.0 Hz), 7.55-7.62(1H, m), 7.74-7.80(1H, m), 7.96-8.03(1H, m), 8.48 (1H, d, J=4.0 Hz).

Example 33

Synthesis of (2R)-2-(2-amino-2-methylpropanamido)-N-(8-(ethylamino)-2-oxo-1-(pyridin-2-ylmethyl))-1,2,3,4-tetrahydroquinolin-3-yl)-4-methylpentanamide

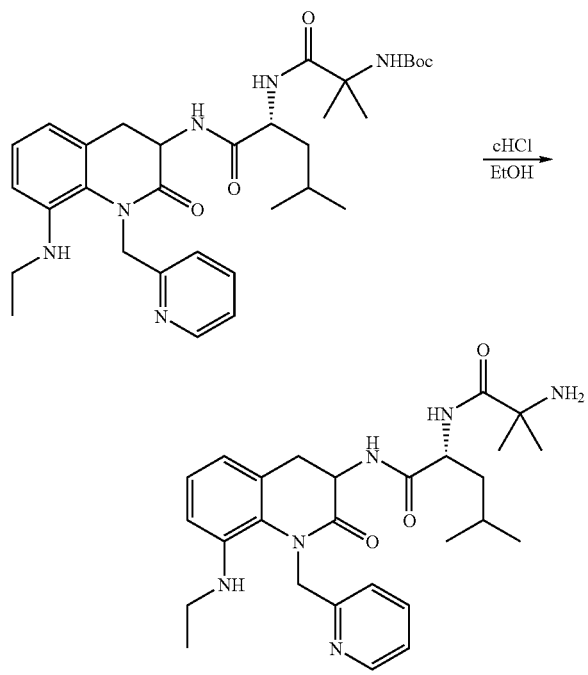

The procedure of Example 25(a) was repeated, except that tert-butyl 1-((2R)-1-(8-(ethylamino)-2-oxo-1-(pyridin-2-ylmethyl)-1,2,3,4-tetrahydroquinolin-3-ylamino)-4-methyl-1-oxopentan-2-ylamino)-2-methyl-1-oxopropan-2-ylcarbamate (67 mg) was used, whereby the title compound (52 mg) was yielded.

MS(FAB)m/z495(M+H)$^+$ $^1$H-NMR(400 MHz, DMSO-d$_6$):

δ(ppm)0.85(3H, d, J=7.0 Hz), 0.87(3H, d, J=7.0 Hz), 1.10 (3H, t, J=7.0 Hz), 1.15(3H, s), 1.17(3H, s), 1.43-1.59(3H, m), 1.98-2.05(2H, m), 2.74(1H, dd, J=5.0, 10.0 Hz), 2.91-3.11 (3H, m), 4.29-4.42(2H, m), 4.92(2H, s), 6.28-6.35(1H, m), 6.56(1H, d, J=7.5 Hz), 6.61(1H, d, J=8.0 Hz), 6.98(1H, t, J=7.5 Hz), 7.27(1H, dd, J=2.0, 5.0 Hz), 7.37(1H, d, J=8.0 Hz), 7.73-7.80(1H, m), 8.03(1H, br), 8.32(1H, t, J=4.0 Hz), 8.47 (1H, d, J=4.5 Hz).

Example 34(a)

Synthesis of (2R)-2-(2-amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide hydrochloride

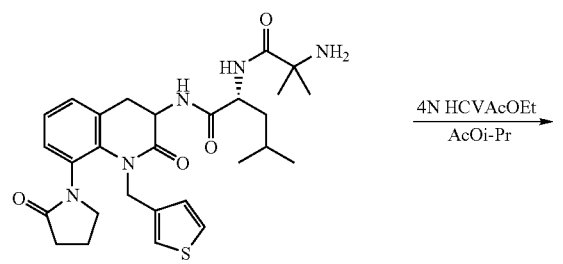

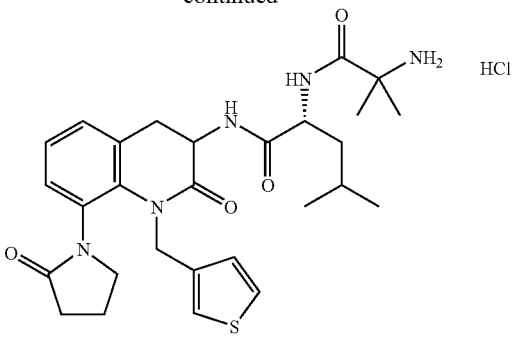

(2R)-2-(2-Amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (1.5 g) was dissolved in isopropyl acetate (68.5 mL), and 4N hydrochloric acid in ethyl acetate (0.95 mL) was added thereto. The mixture was stirred at 55° C. for one hour, and then left to stand to cool to room temperature. The formed precipitates were recovered through filtration, washed with isopropyl acetate, and dried under reduced pressure, whereby the title compound (1.47 g) was yielded.

$^1$H-NMR(400 MHz, DMSO-d$_6$, 80° C.)

δ(ppm)0.88(3H, d, J=6.0 Hz), 0.91(3H, d, J=6.0 Hz), 1.53-1.70(9H, m), 1.90-2.06(2H, m), 2.25-2.39(2H, m), 2.80(1H, t, J=14.5 Hz), 2.94(1H, dd, J=5.0, 14.5 Hz), 3.37-3.43(1H, m), 3.77-3.79(1H, m), 4.38-4.49(2H, m), 4.58(1H, d, J=16.0 Hz), 5.17(1H, d, J=16.0 Hz), 6.79-6.80(1H, m), 7.04-7.19 (4H, m), 7.32-7.34(1H, m), 7.98(1H, d, J=7.0 Hz), 8.10-8.25 (3H, m).

Example 34(b)

Synthesis of 2-amino-2-methyl-N-[(2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]propanamide hydrochloride

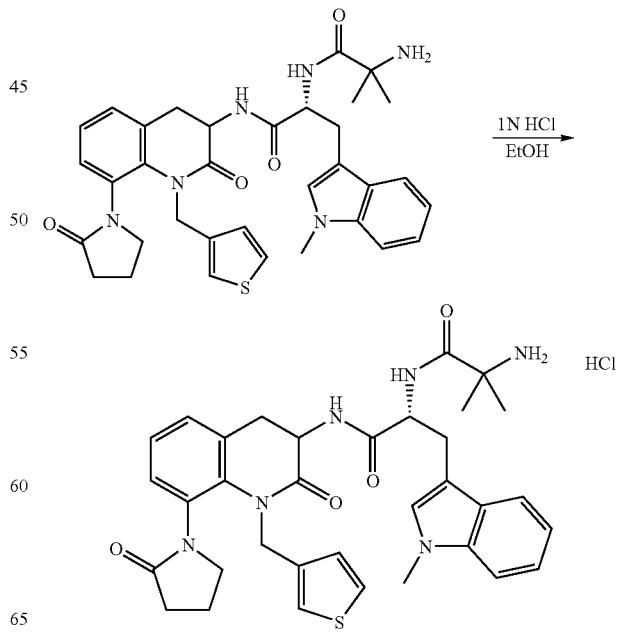

2-Amino-2-methyl-N-[(2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl] propanamide (116 mg) was dissolved in ethanol (1.0 mL), and 1N hydrochloric acid (161 μL) was added thereto. Subsequently, the solvent was evaporated under reduced pressure, whereby the title compound (103 mg) was yielded.

$^1$H-NMR(400 MHz, DMSO-d$_6$, 80° C.):

δ(ppm)1.36(3H, s), 1.51(3H, s), 1.89-2.04(2H, m), 2.24-2.38(2H, m), 2.69(1H, t, J=14.0 Hz), 2.80(1H, dd, J=5.0, 10.0 Hz), 3.10(1H, dd, J=5.0, 9.0 Hz), 3.23(1H, dd, J=5.5, 9.0 Hz), 3.38-3.42(1H, m), 3.71(3H, s), 3.76-3.78(1H, m), 4.36-4.43 (1H, m), 4.58(1H, d, J=15.5 Hz), 4.65-4.71(1H, m), 5.17(1H, d, J=15.5 Hz), 6.79(1H, d, J=5.0 Hz), 6.98-7.03(2H, m), 7.09-7.19(5H, m), 7.32-7.35(2H, m), 7.64(1H, d, J=8.0 Hz), 8.05(1H, d, J=5.0 Hz), 8.15(3H, s), 8.28 (1H, d, J=8.0 Hz).

Example 34(c)

Synthesis of 2-amino-N-[(2R)-3-(1-ethyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-methylpropanamide hydrochloride

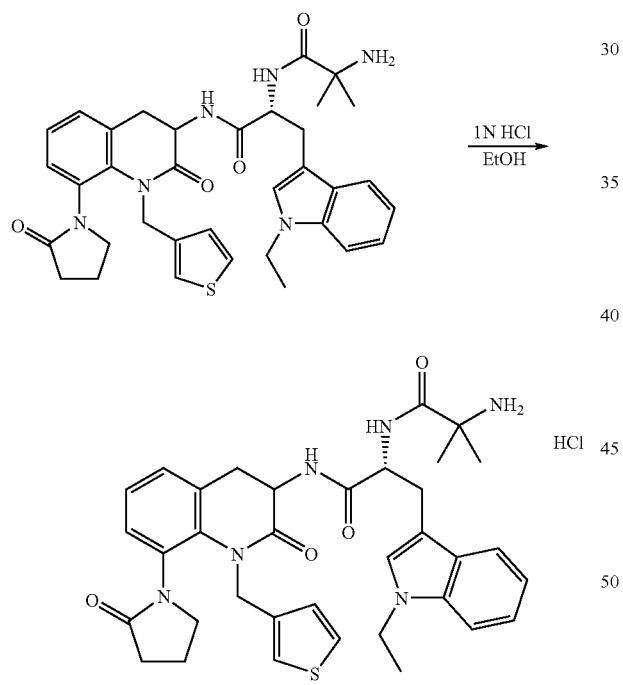

The procedure of Example 34(b) was repeated, except that 2-amino-N-[(2R)-3-(1-ethyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-methylpropanamide (233 mg) was used, whereby the title compound (210 mg) was yielded.

$^1$H-NMR (400 MHz, DMSO-d$_6$):

δ(ppm)1.26-1.36(6H, m), 1.47(3H, s), 1.82-2.41(4H, m), 2.69-2.81(2H, m), 3.03(1H, dd, J=10.5 Hz, 14.0 Hz), 3.18 (1H, dd, J=5.0, 14.0H z), 3.40-3.53(2H, m), 4.09-4.20(2H, m), 4.33-4.82(3H, m), 5.00-5.22(1H, m), 6.80(1H, d, J=4.5 Hz), 7.01(1H, t, J=7.5 Hz), 7.06-7.26(6H, m), 7.40-7.46(2H, m), 7.76(1H, d, J=8.0 Hz), 8.04(3H, s), 8.50(1H, d, J=8.5 Hz), 8.64 (1H, d, J=8.0 Hz).

Example 34(d)

Synthesis of 2-amino-N-[(2R)-3-[1-(2-fluoroethyl)-1H-indol-3-yl]-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-methylpropanamide hydrochloride

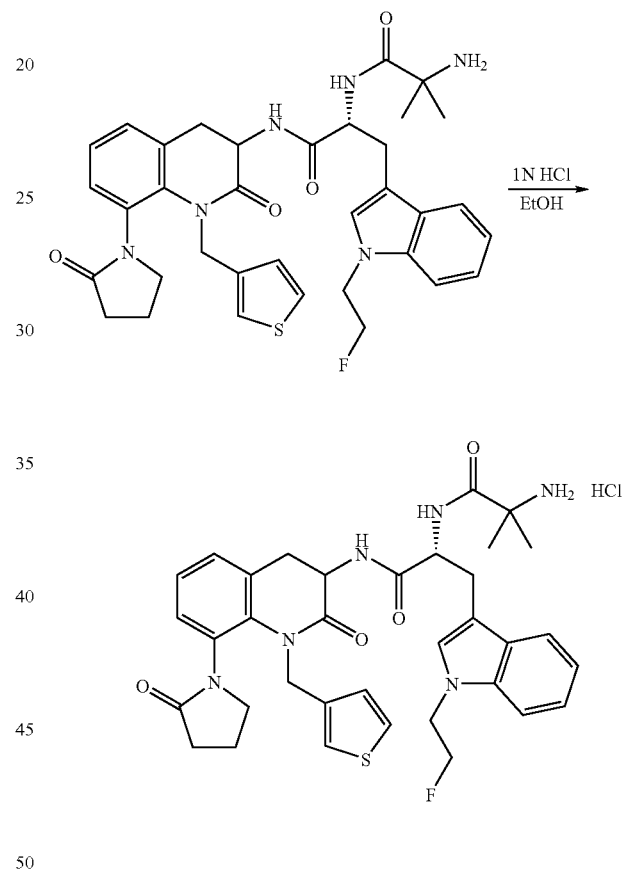

The procedure of Example 34(b) was repeated, except that 2-amino-N-[(2R)-3-[1-(2-fluoroethyl)-1H-indol-3-yl]-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-methylpropanamide (205 mg) was used, whereby the title compound (210 mg) was yielded.

$^1$H-NMR(400 MHz, DMSO-d$_6$, 80° C.):

δ(ppm)1.35(3H, s), 1.49(3H, s), 1.82-2.08(2H, m), 2.23-2.38(2H, m), 2.61-2.71(1H, m), 2.79(1H, dd, J=5.0, 15.0 Hz), 3.02-3.29(2H, m), 3.34-3.58(1H, m), 3.72-3.85(1H, m), 4.33-4.49(3H, m), 4.52-4.66(2H, m), 4.67-4.78(2H, m), 5.17(1H, d, J=15.5 Hz), 6.74-6.81(1H, m), 7.03(2H, t, J=7.0 Hz), 7.06-7.22(5H, m), 7.30-7.36(1H, m), 7.41(1H, d, J=8.0 Hz), 7.67 (1H, d, J=8.0 Hz), 7.92-8.09(4H, m), 8.20(1H, d, J=8.0 Hz).

Example 34(e)

Synthesis of 2-amino-2-methyl-N-[(2R)-1-oxo-1-[2-oxo-8-(2-oxopyrrolidin-1-yl)-1-(thiophen-3-ylmethyl)-1,2,3,4-tetrahydroquinolin-3-ylamino]-3-(1-propyl-1H-indol-3-yl)propan-2-yl]propanamide hydrochloride

Example 34(f)

Synthesis of 2-amino-N-[(2R)-3-(1-isopropyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-methylpropanamide hydrochloride

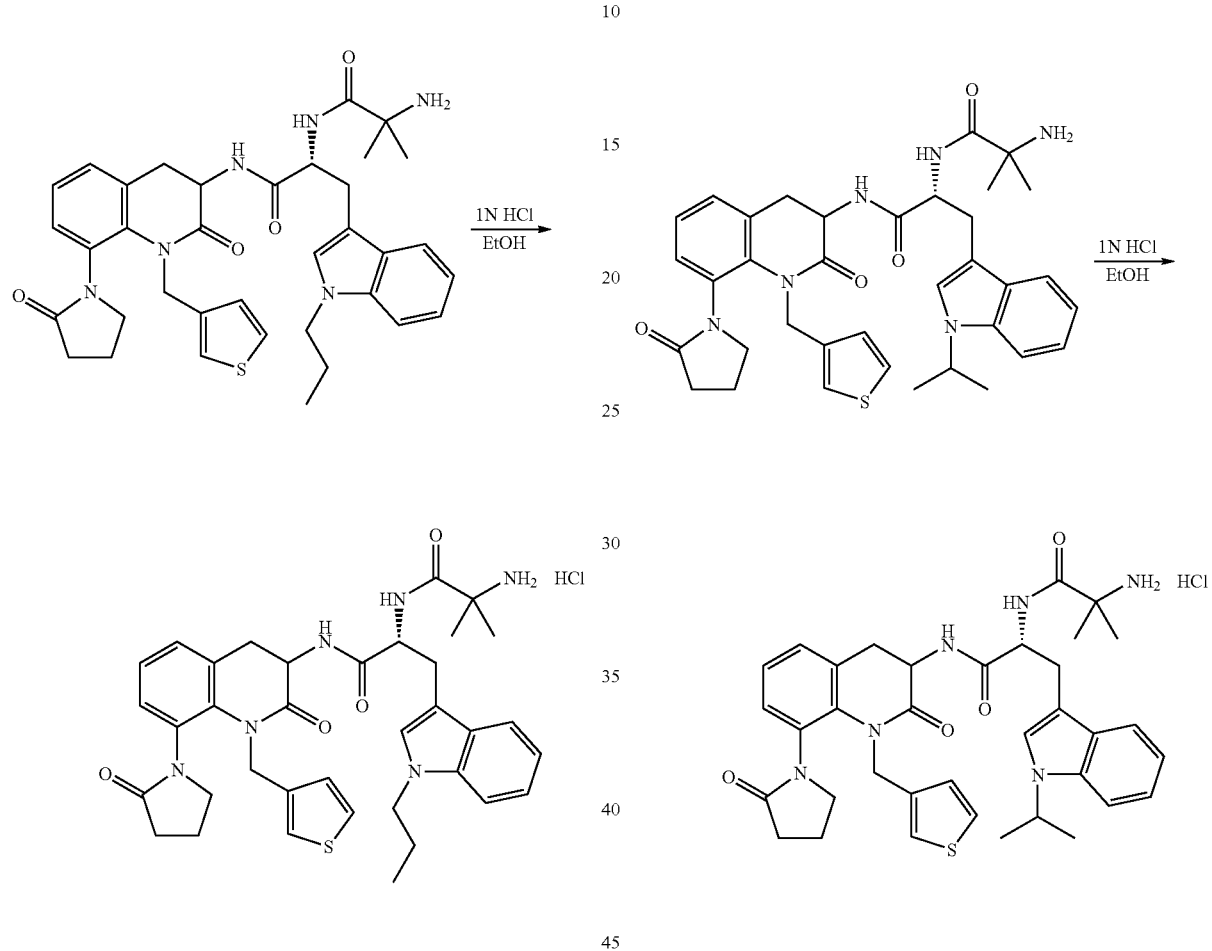

The procedure of Example 34(b) was repeated, except that 2-amino-2-methyl-N-[(2R)-1-oxo-1-[2-oxo-8-(2-oxopyrrolidin-1-yl)-1-(thiophen-3-ylmethyl)-1,2,3,4-tetrahydroquinolin-3-ylamino]-3-(1-propyl-1H-indol-3-yl)propan-2-yl]propanamide (260 mg) was used, whereby the title compound (266 mg) was yielded.

$^1$H-NMR(400 MHz, DMSO-d$_6$, 80° C.):

δ(ppm)0.86(3H, t, J=7.5 Hz), 1.35(3H, s), 1.50(3H, s), 1.71-1.81(2H, m), 1.83-2.09(2H, m), 2.23-2.39(2H, m), 2.65 (1H, t, J=14.0 Hz), 2.78(1H, dd, J=5.0, 15.0 Hz), 3.01-3.28 (2H, m), 3.33-3.45(1H, m), 3.71-3.86(1H, m), 4.00-4.08(2H, m), 4.37-4.47(1H, m), 4.57(1H, d, J=15.5 Hz), 4.67-4.76(1H, m), 5.17(1H, d, J=15.5 Hz), 6.74-6.81(1H, m), 6.95-7.04(2H, m), 7.05-7.23(5H, m), 7.29-7.40(2H, m), 7.64(1H, d, J=8.0 Hz), 7.95-8.14(4H, m), 8.21(1H, d, J=8.0 Hz).

The procedure of Example 34(b) was repeated, except that 2-amino-N-[(2R)-3-(1-isopropyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]-2-methylpropanamide (337 mg) was used, whereby the title compound (298 mg) was yielded.

$^1$H-NMR(400 MHz, DMSO-d$_6$, 80° C.):

δ(ppm)1.33(3H, s), 1.39-1.49(9H, m), 1.83-2.08(2H, m), 2.23-2.40(2H, m), 2.56-2.69(1H, m), 2.76(1H, dd, J=5.0, 15.0 Hz), 3.04-3.14(1H, m), 3.18-3.26(1H, m), 3.34-3.49 (1H, m), 3.51-3.86(1H, m), 4.35-4.47(1H, m), 4.57(1H, d, J=15.5 Hz), 4.62-4.76(2H, m), 5.17(1H, d, J=15.5 Hz), 6.74-6.80(1H, m), 6.96-7.03(2H, m), 7.06-7.22(4H, m), 7.29 (1H, s), 7.31-7.36(1H, m), 7.41(1H, d, J=8.0 Hz), 7.47-7.76 (4H, m), 8.02(1H, d, J=7.0 Hz), 8.06-8.27(1H, m).

Example 34(g)

Synthesis of (2R)-2-((R)-2-aminopropanamido)-4-methyl-N-[2-oxo-8-(2-oxopyrrolidin-1-yl)-1-(thiophen-3-ylmethyl)-1,2,3,4-tetrahydroquinolin-3-yl]pentanamide hydrochloride

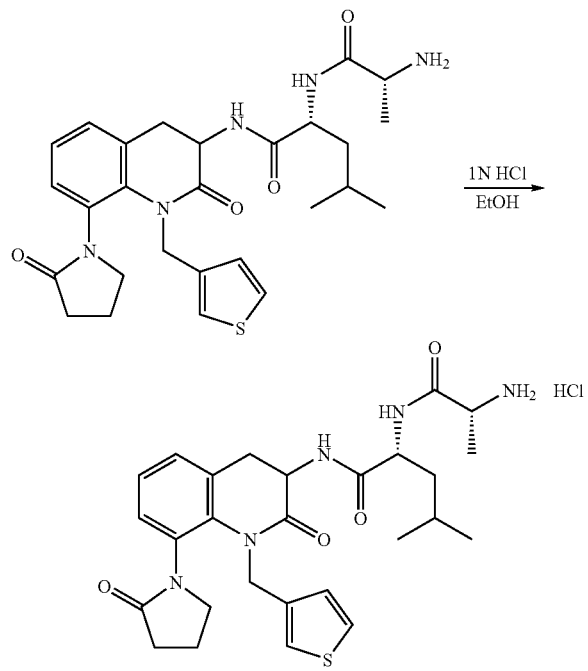

The procedure of Example 34(b) was repeated, except that (2R)-2-((R)-2-aminopropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (50 mg) was used, whereby the title compound (48 mg) was yielded.

¹H-NMR(400 MHz, DMSO-$d_6$, 80° C.):
δ(ppm)0.90(6H, t, J=6.5 Hz), 1.38(3H, d, J=7 Hz), 1.54 (2H, m), 1.67(1H, m), 1.9-2.0(2H, m), 2.30(2H, m), 2.78(1H, t, J=15 Hz), 2.91(1H, m), 3.40(1H, m), 3.77(1H, m), 3.88(1H, m), 4.45(2H, m), 4.58(1H, d, J=15.5 Hz), 5.16(1H, d, J=15.5 Hz), 6.80(1H, d, J=5 Hz), 7.03(1H, br s), 7.09-7.20(3H, m), 7.34(1H, m), 7.83-8.07(4H, m), 8.29(1H, br s).

Example 34(h)

Synthesis of (2R)-2-((R)-2-amino-2-methylbutanamido)-4-methyl-N-[2-oxo-8-(2-oxopyrrolidin-1-yl)-1-(thiophen-3-ylmethyl)-1,2,3,4-tetrahydroquinolin-3-yl]pentanamide hydrochloride

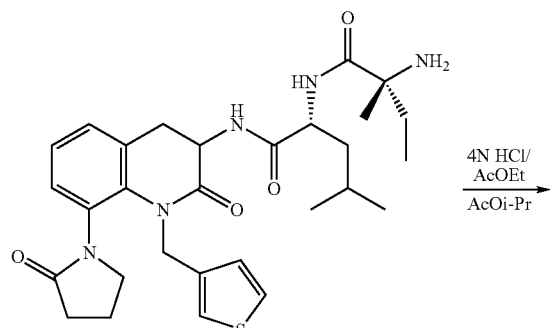

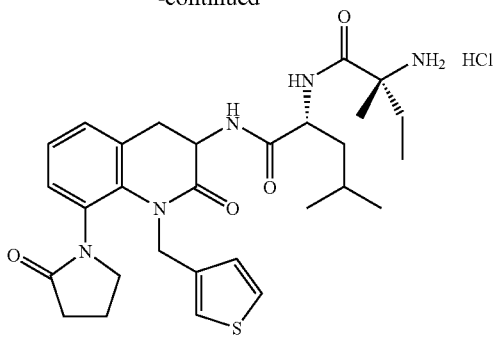

The procedure of Example 34(a) was repeated, except that (2R)-2-((R)-2-amino-2-methylbutanamido)-4-methyl-N-[2-oxo-8-(2-oxopyrrolidin-1-yl)-1-(thiophen-3-ylmethyl)-1,2,3,4-tetrahydroquinolin-3-yl]pentanamide (5.57 g) was used, whereby the title compound (5.55 g) was yielded.

¹H-NMR(400 MHz, DMSO-$d_6$):
δ(ppm)0.82-0.93(9H, m), 1.47(3H, s), 1.50(1H, m), 1.64 (2H, m), 1.75(1H, m), 2.05(1H, m), 2.30(2H, br s), 2.83(2H, m), 4.50(1H, br s), 4.54(2H, br s), 6.80(1H, d, J=5 Hz), 7.09(1H, br s), 7.14(1H, m), 7.23(1H, m), 7.42(1H, m), 8.08 (2H, br s), 8.36(1H, d, J=8 Hz), 8.45(1H, d, J=6.5 Hz).

Example 34(i)

Synthesis of (2R)-2-amino-2-methyl-N-[(2R)-3-(1-methyl-1H-indol-3-yl)-1-oxo-1-[2-oxo-8-(2-oxopyrrolidin-1-yl)-1-(thiophen-3-ylmethyl)-1,2,3,4-tetrahydroquinolin-3-ylamino]propan-2-yl]butanamide hydrochloride

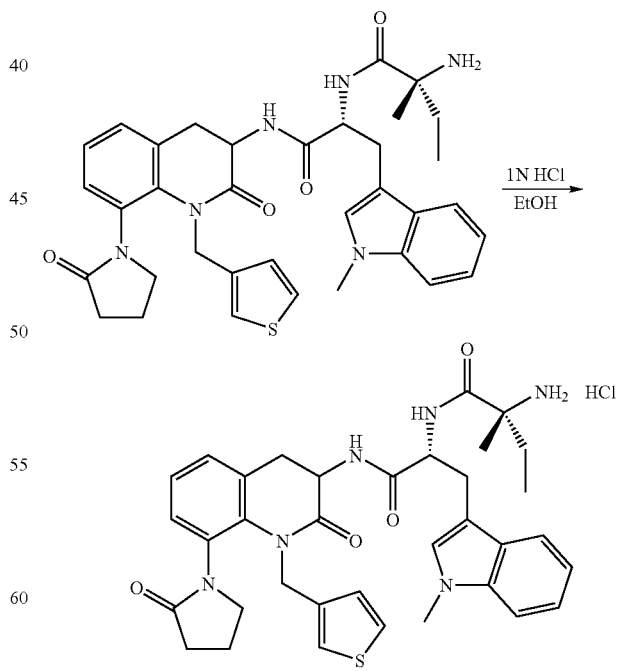

The procedure of Example 34(b) was repeated, except that (2R)-2-amino-2-methyl-N-[(2R)-3-(1-methyl-1H-indol-3-yl)-1-oxo-1-[2-oxo-8-(2-oxopyrrolidin-1-yl)-1-(thiophen-3- ylmethyl)-1,2,3,4-tetrahydroquinolin-3-ylamino]propan-2-yl]butanamide (8.4 g) was used, whereby the title compound (6.56 g) was yielded.

$^1$H-NMR(400 MHz, DMSO-d$_6$, 80° C.):

δ(ppm)0.82(3H, t, J=7.5 Hz), 1.34(3H, s), 1.76-1.83(1H, m), 1.85-2.08(3H, m), 2.25-2.39(2H, m), 2.65(1H, t, J=14.0 Hz), 2.80(1H, dd, J=5.0, 10.0 Hz), 3.09(1H, dd, J=5.0, 9.0 Hz), 3.21(1H, dd, J=5.5, 9.0 Hz), 3.37-3.43(1H, m), 3.71 (3H, s), 3.73-3.82(1H, m), 4.39-4.43(1H, m), 4.56(1H, d, J=15.6 Hz), 4.65-4.75(1H, m), 5.17(1H, d, J=15.5 Hz), 6.78 (1H, d, J=5.0 Hz), 6.99-7.06(2H, m), 7.09-7.19(5H, m), 7.32-7.35(2H, m), 7.65(1H, d, J=8.0 Hz), 7.80-7.98(3H, m), 8.01 (1H, d, J=7.0 Hz), 8.17-8.25(1H, m).

Example 34(j)

Synthesis of (2R)-2-(2-amino-2-methylpropanamido)-4-methyl-N-[2-oxo-8-(2-oxopyrrolidin-1-yl)-1-(pyridin-2-ylmethyl)-1,2,3,4-tetrahydroquinolin-3-yl]pentanamide hydrochloride

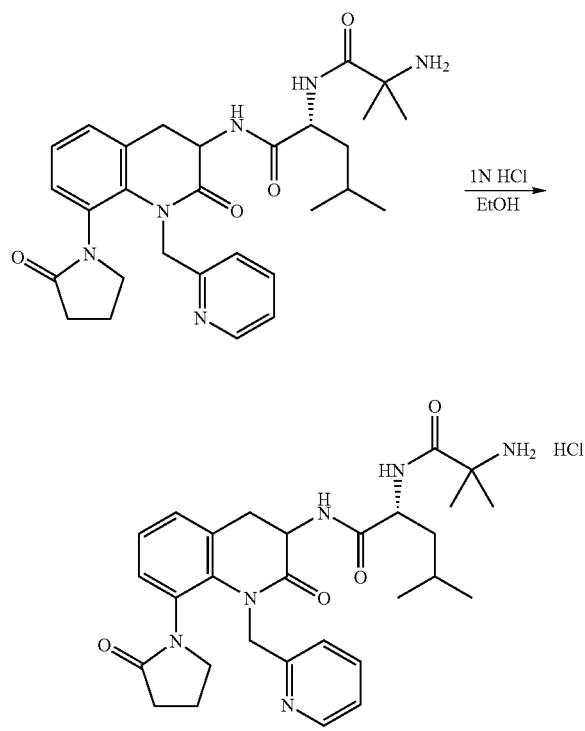

The procedure of Example 34(a) was repeated, except that (2R)-2-(2-amino-2-methylpropanamido)-4-methyl-N-[2-oxo-8-(2-oxopyrrolidin-1-yl)-1-(pyridin-2-ylmethyl)-1,2,3,4-tetrahydroquinolin-3-yl]pentanamide (74 mg) was used, whereby the title compound (55 mg) was yielded.

$^1$H-NMR(400 MHz, DMSO-d$_6$, 80° C.):

δ(ppm)0.87(3H, d, J=6.5 Hz), 0.89(3H, d, J=6.5 Hz), 1.19 (3H, s), 1.20(3H, s), 1.48-1.81(4H, m), 1.85-1.98(2H, m), 2.13-2.29(2H, m), 2.94-3.09(4H, m), 3.35-3.43(1H, m), 3.66-3.79(1H, m), 4.37(1H, dd, J=5.5, 8.5 Hz), 4.43-4.53(1H, m), 4.74(1H, d, J=16.5 Hz), 5.14(1H, d, J=16.5 Hz), 7.05-7.24 (5H, m), 7.64(1H, dt, J=2.0, 7.5 Hz), 7.70-8.30(1H, br), 7.94 (1H, d, J=7.0 Hz), 8.39(1H, d, J=5.0 Hz).

Example 34(k)

Synthesis of (2R)-2-(2-amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (R)-(−)-mandelate

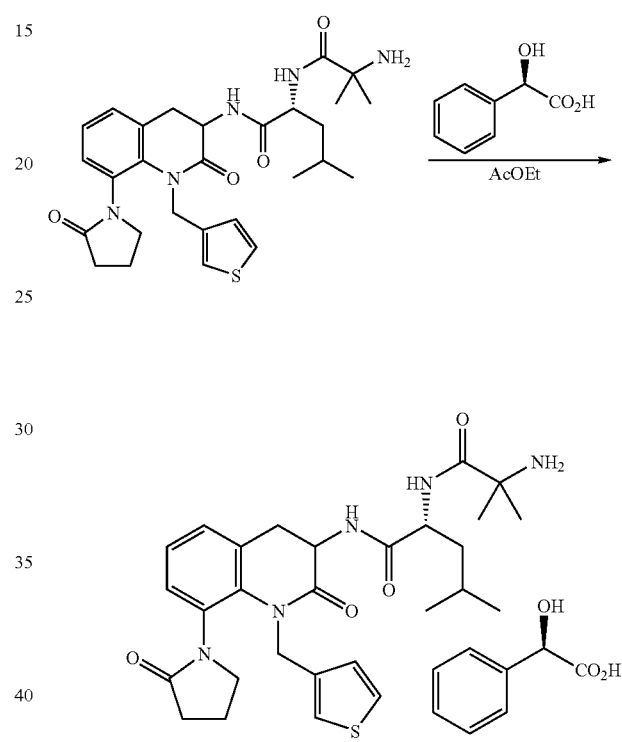

(2R)-2-(2-Amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (542 mg) was dissolved in ethyl acetate (6.5 mL), and (R)-(−)-mandelic acid (141 mg) was added thereto. The mixture was stirred at 70° C. for 10 minutes, and then left to stand to cool to room temperature. The formed precipitates were recovered through filtration, washed with ethyl acetate, and dried under reduced pressure, whereby the title compound (589 mg) was yielded.

Mp: 183-185° C.

$^1$H-NMR(400 MHz, DMSO-d$_6$:

δ(ppm)0.87(3H, d, J=6.5 Hz), 0.90(3H, d, J=6.5 Hz), 1.36 (3H, s), 1.37(3H, s), 1.43-1.66(4H, m), 1.85-2.42(3H, m), 2.70-2.95(2H, m), 3.10-4.10(2H, m), 4.35-4.80(3H, m), 4.60 (1H, s), 4.98-5.27(1H, m), 6.30-7.00(3H, br), 6.81(1H, d, J=5.0 Hz), 7.05-7.28(8H, m), 7.33-7.45(3H, m), 8.29(1H, d, J=8.0 Hz), 8.48(1H, d, J=7.5 Hz).

Example 34(l)

Synthesis of (2R)-2-(2-amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (S)-(+)-mandelate

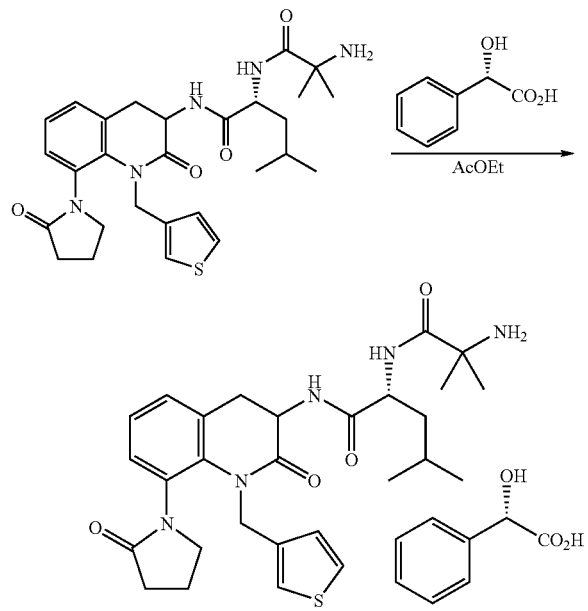

The procedure of Example 34(k) was repeated, except that (2R)-2-(2-amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (33 mg) and (S)-(+)-mandelic acid (8.5 mg) were used, whereby the title compound (24 mg) was yielded.

Mp: 171-173° C.

$^1$H-NMR(400 MHz, DMSO-d$_6$):

δ(ppm)0.87(3H, d, J=6.0 Hz), 0.90(3H, d, J=6.0 Hz), 1.36 (3H, s), 1.36(3H, s), 1.44-1.65(4H, m), 1.85-2.05(1H, m), 2.20-2.40(2H, m), 2.73-2.97(2H, m), 3.20-4.10(2H, m), 4.35-4.80(3H, m), 4.62(1H, s), 5.00-5.20(1H, m), 6.40-7.00(3H, br), 6.80(1H, d, J=5.0 Hz), 7.05-7.28(8H, m), 7.33-7.44(3H, m), 8.28(1H, d, J=8.0 Hz), 8.46(1H, d, J=7.5 Hz).

Example 34(m)

Synthesis of (2R)-2-(2-amino-2-methylpropanamido)-4-methyl-N-[2-oxo-8-(2-oxopyrrolidin-1-yl)-1-(thiophen-2-ylmethyl)-1,2,3,4-tetrahydroquinolin-3-yl]pentanamide hydrochloride

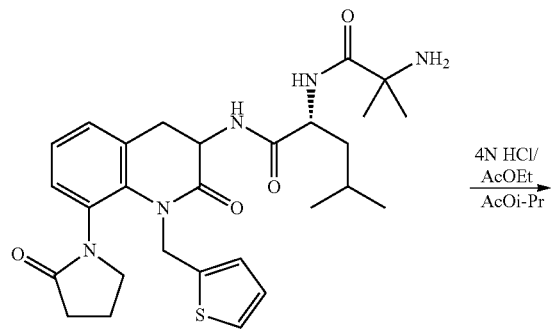

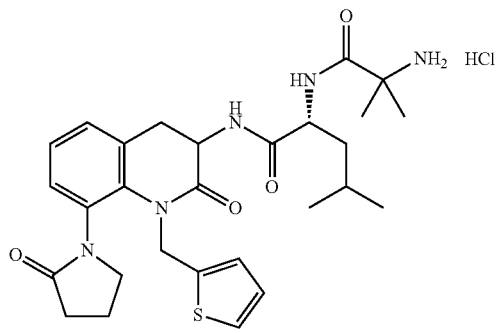

The procedure of Example 34(a) was repeated, except that (2R)-2-(2-amino-2-methylpropanamido)-4-methyl-N-[2-oxo-8-(2-oxopyrrolidin-1-yl)-1-(thiophen-2-ylmethyl)-1,2,3,4-tetrahydroquinolin-3-yl]pentanamide (1.0 g) was used, whereby the title compound (933 mg) was yielded.

$^1$H-NMR(400 MHz, DMSO-d$_6$):

δ(ppm)0.87(3H, d, J=6.0 Hz), 0.90(3H, d, J=6.0 Hz), 1.43-1.77(9H, m), 1.92-2.27(2H, m), 2.31-2.48(2H, m), 2.73(1H, t, J=14.5 Hz), 2.87(1H, dd, J=5.0, 14.5 Hz), 3.28-3.75(2H, m), 4.31-4.92(3H, m), 5.23-5.65(1H, br s), 6.75-6.89(2H, m), 7.11-7.27(3H, m), 7.34(1H, d, J=5.0 Hz), 8.30(3H, br s), 8.40(1H, d, J=8.5 Hz), 8.51(1H, d, J=7.5 Hz).

Example 35

(2R)-2-(2-Amino-2-methylpropanamido)-N-[1-benzyl-2-oxo-8-(2-oxopyrrolidin-1-yl)-1,2,3,4-tetrahydroquinolin-3-yl]-4-methylpentanamide hydrochloride

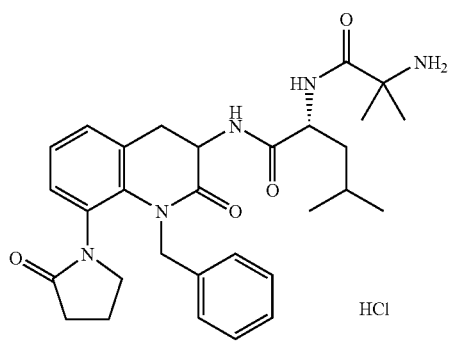

$^1$H-NMR(400 MHz, DMSO-d$_6$, 80° C.):

δ(ppm)0.88(3H, d, J=6.0 Hz), 0.91(3H, d, J=6.0 Hz), 1.52-1.80(10H, m), 1.84-1.98(1H, m), 2.13-2.32(2H, m), 2.85(1H, t, J=14.5 Hz), 2.98(1H, dd, J=5.0, 14.5 Hz), 3.32-3.40(1H, m), 3.64-3.83(1H, m), 4.41-4.52(2H, m), 4.65(1H, d, J=16.0 Hz), 5.08(1H, d, J=16.0 Hz), 7.03-7.28(8H, m), 7.99(1H, d, J=7.0 Hz), 8.11-8.38(4H, m).

Example 36

(2R)-2-(2-Amino-2-methylpropanamido)-N-[1-benzyl-2-oxo-8-(2-oxopiperidin-1-yl)-1,2,3,4-tetrahydroquinolin-3-yl]-4-methylpentanamide hydrochloride

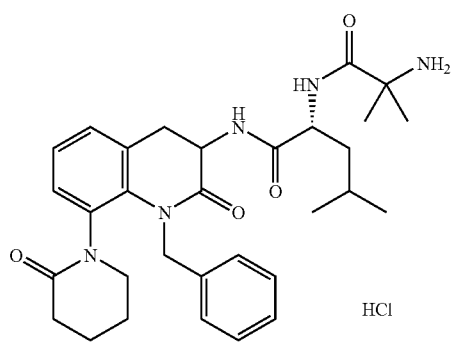

¹H-NMR(400 MHz, DMSO-d₆):

δ(ppm)0.84-0.91(6H, m), 1.25-2.39(14H, m), 2.81-3.90 (7H, m), 4.31-5.19(4H, m), 7.04-7.33(8H, m), 8.18-8.38(2H, m).

Example 37

(2R)-2-(2-Amino-2-methylpropanamido)-N-[1-benzyl-8-(2,5-dioxopyrrolidin-1-yl)-2-oxo-1,2,3,4-tetrahydroquinolin-3-yl]-4-methylpentanamide hydrochloride

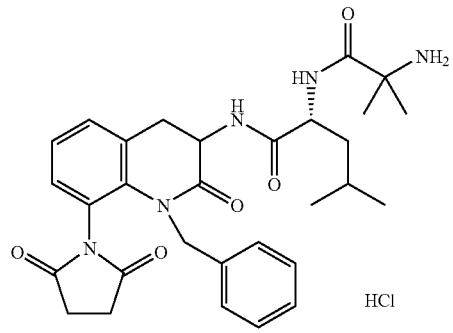

¹H-NMR (400 MHz, DMSO-d₆, 80° C.):

δ(ppm) 0.87(3H, d, J=6.5 Hz), 0.91(3H, d, J=6.5 Hz), 1.24-1.38(1H, m), 1.44-1.73(9H, m), 1.94-2.05(1H, m), 2.28-2.39(1H, m), 2.52-2.63(1H, m), 2.95-3.10(2H, m), 4.30(1H, d, J=17.0 Hz), 4.50-4.62(2H, m), 4.98(1H, d, J=17.0 Hz), 6.97(2H, d, J=7.0 Hz), 7.11-7.15(1H, m), 7.21-7.36(4H, m), 7.43(1H, d, J=7.0 Hz), 8.23(3H, br s), 8.41(1H, d, J=8.5 Hz), 8.54(1H, d, J=8.0 Hz).

Example 38

2-Amino-N-[(2R)-1-[1-benzyl-2-oxo-8-(2-oxopyrrolidin-1-yl)-1,2,3,4-tetrahydroquinolin-3-ylamino]-3-(1H-indol-3-yl)-1-oxopropan-2-yl]-2-methylpropanamide hydrochloride

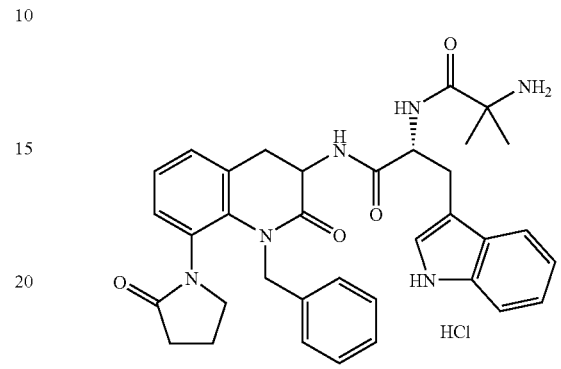

¹H-NMR (400 MHz, DMSO-d₆, 80° C.):

δ(ppm) 1.34(3H, s), 1.49(3H, s), 1.65-1.69(1H, m), 1.83-1.95(1H, m), 2.14-2.30(2H, m), 2.74-2.85(2H, m), 3.03-3.48 (3H, m), 3.64-3.78(1H, m), 4.43-4.50(1H, m), 4.63-4.73(2H, m), 5.10(1H, d, J=16.0 Hz), 6.96(1H, t, J=7.5 Hz), 7.03-7.24 (10H, m), 7.32(1H, d, J=8.0 Hz), 7.63(1H, d, J=8.0 Hz), 8.04-8.15(4H, m), 8.22(1H, d, J=8.0 Hz), 10.62(1H, s).

Example 39

(2R)-2-((R)-2-Amino-3-(4-hydroxyphenyl)propanamido)-N-(8-(diethylamino)-2-oxo-1-(pyridin-2-ylmethyl)-1,2,3,4-tetrahydroquinolin-3-yl)-4-methylpentanamide hydrochloride

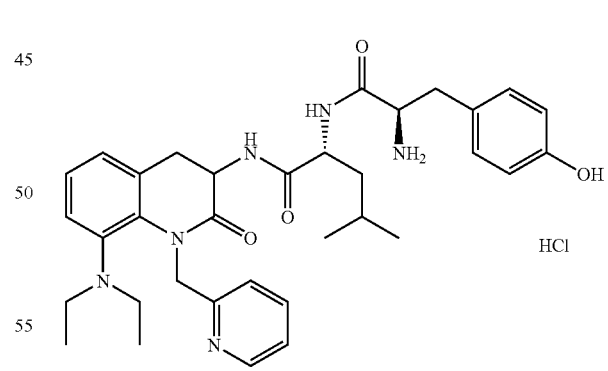

MS(FAB)m/z601(M+H)⁺

¹H-NMR(400 MHz, DMSO-d₆):

δ(ppm)0.75-1.03(12H, m), 1.43-1.55(2H, m), 1.59-1.71 (1H, m), 2.70-3.09(8H, m), 3.97(1H, br), 4.40-4.49(1H, m), 4.56(1H, dd, J=6.5, 8.5 Hz), 5.44(1H, d, J=16.0 Hz), 5.86(1H, d, J=16.0 Hz), 6.67(2H, d, J=12.5 Hz), 6.92-7.36(7H, m), 7.59-7.66(1H, m), 8.11(3H, br), 8.36(1H, d, J=4.5 Hz), 8.60 (1H, d, J=7.5 Hz), 8.67(1H, d, J=8.5 Hz), 9.34(1H, s).

Example 40

(2R)—N-(8-Acetamido-2-oxo-1-(pyridin-2-ylmethyl)-1,2,3,4-tetrahydroquinolin-3-yl)-2-(2-amino-2-methylpropanamido)-4-methylpentanamide

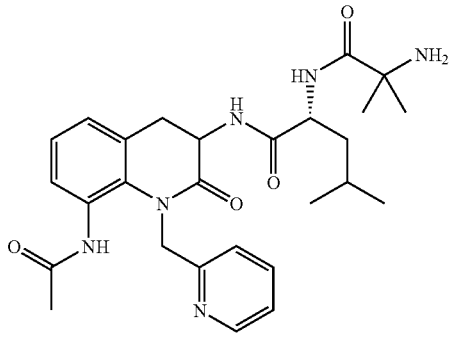

MS(FAB)m/z509(M+H)+

¹H-NMR(400 MHz, DMSO-d₆):

δ(ppm)0.86(3H, d, J=6.5 Hz), 0.88(3H, d, J=6.5 Hz), 1.15 (3H, s), 1.16(3H, s), 1.44-1.60(3H, m), 1.81(3H, s), 1.95-2.17 (2H, m), 2.88(1H, dd, J=5.0, 10.5 Hz), 3.05(1H, t, J=14.5 Hz), 4.35-4.47(2H, m), 4.87(1H, d, J=16.0 Hz), 5.02(1H, d, J=16.0 Hz), 7.06(1H, t, J=8.0 Hz), 7.12(1H, d, J=7.5 Hz), 7.21-7.29(2H, m), 7.41(1H, d, J=7.5 Hz), 7.70-7.77(1H, m), 8.03 (1H, br), 8.41(1H, d, J=8.0 Hz), 8.46(1H, d, J=4.0 Hz), 10.00 (1H, s).

Example 41

2-Amino-N-((1R)-2-(8-(dimethylamino)-2-oxo-1-(pyridin-2-ylmethyl)-1,2,3,4-tetrahydroquinolin-3-ylamino)-2-oxo-1-phenylethyl)-2-methylpropanamide hydrochloride

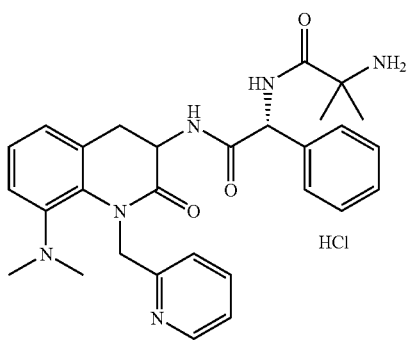

MS(FAB)m/z515(M+H)+

¹H-NMR(400 MHz, DMSO-d₆:

δ(ppm)1.50(3H, s), 1.53(3H, s), 2.51-2.69(6H, s), 2.76 (1H, dd, J=5.0, 10.0 Hz), 3.00(1H, t, J=14.5 Hz), 4.48-4.58 (1H, m), 5.42(1H, d, J=16.0 Hz), 5.53(1H, d, J=16.0 Hz), 5.81(1H, d, J=8.0 Hz), 6.84-6.99(3H, m), 7.10-7.18(2H, m), 7.29-7.41(3H, m), 7.48(2H, d, J=7.5 Hz), 7.61-7.68(1H, m), 8.22(3H, br), 8.35(1H, d, J=4.0 Hz), 8.82(1H, d, J=8.5 Hz), 8.89(1H, d, J=8.0 Hz).

Example 42

(2R)-2-(2-Amino-2-methylpropanamido)-N-(8-(N-ethylacetamido)-2-oxo-1-(pyridin-2-ylmethyl)-1,2,3,4-tetrahydroquinolin-3-yl)-4-methylpentanamide hydrochloride

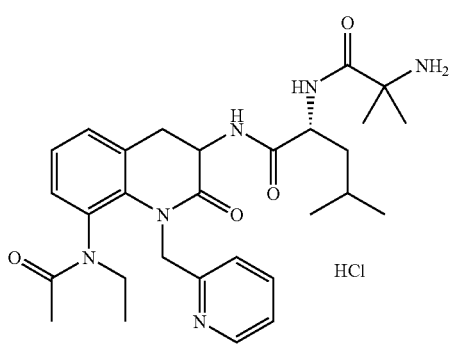

MS(FAB)m/z537(M+H)+

¹H-NMR(400 MHz, DMSO-d₆):

δ(ppm)0.81-0.94(9H, m), 1.08-1.75(9H, m), 2.80-3.20 (3H, m), 3.93-4.04(1H, m), 4.53-4.62(2H, m), 4.69-5.68(2H, m), 7.06-7.38(5H, m), 7.67-7.77(1H, m), 8.14(3H, br), 8.30-8.58(3H, m).

Example 43

(2R)-2-(2-Amino-2-methylpropanamido)-N-[8-(diethylamino)-2-oxo-1-(pyridin-2-ylmethyl)-1,2,3,4-tetrahydroquinolin-3-yl]-4-(methylthio)butanamide hydrochloride

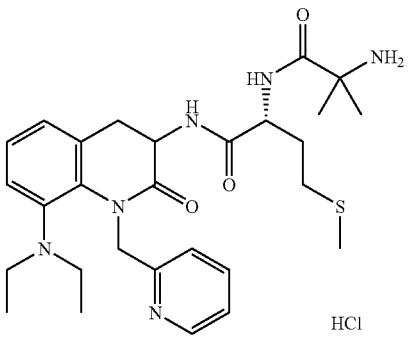

MS(FAB)m/z541(M+H)+

¹H-NMR(400 MHz, DMSO-d₆:

δ(ppm)0.75-0.85(3H, m), 0.93-1.03(3H, m), 1.47(3H, s), 1.49(3H, s), 1.83-2.08(2H, m), 2.06(3H, s), 2.35-2.55(2H, m), 2.86-3.18(6H, m), 4.28-4.48(1H, m), 4.54-4.63(1H, m), 5.41(1H, d, J=16.0 Hz), 5.85(1H, d, J=16.0 Hz), 6.92-7.05

(3H, m), 7.09(1H, d, J=7.5 Hz), 7.12-7.22(1H, m), 7.62-7.72 (1H, m), 8.16(3H, br s), 8.37(1H, s), 8.39(1H, s), 8.44(1H, d, J=7.5 Hz).

Example 44

2-Amino-N-[(2R)-3-(benzyloxy)-1-[8-(diethylamino)-2-oxo-1-(pyridin-2-ylmethyl)-1,2,3,4-tetrahydroquinolin-3-ylamino]-1-oxopropan-2-yl]-2-methylpropanamide hydrochloride

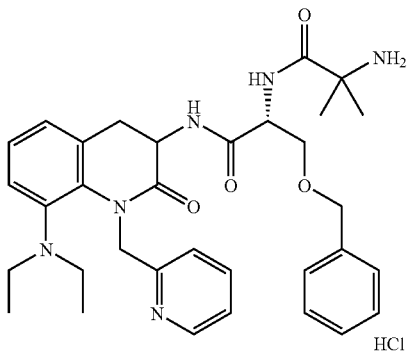

MS(FAB)m/z587(M+H)$^+$
$^1$H-NMR(400 MHz, DMSO-d$_6$):
δ(ppm)0.73-0.87(3H, m), 0.93-1.07(3H, m), 1.49(3H, s), 1.49(3H, s), 2.83-3.20(6H, m), 3.62-3.75(2H, m), 4.37-4.57 (3H, m), 4.82-4.91(1H, m), 5.41(1H, d, J=16.0 Hz), 5.85(1H, d, J=16.0 Hz), 6.88-7.17(5H, m), 7.27-7.39(5H, m), 7.60-7.67(1H, m), 8.15(3H, br s), 8.36(1H, d, J=4.0 Hz), 8.49(1H, d, J=8.0 Hz), 8.54(1H, d, J=7.5 Hz).

Example 45

2-Amino-N-[(2R)-3-(4-chlorophenyl)-1-[8-(dimethylamino)-2-oxo-1-(pyridin-2-ylmethyl)-1,2,3,4-tetrahydroquinolin-3-ylamino]-1-oxopropan-2-yl]-2-methylpropanamide hydrochloride

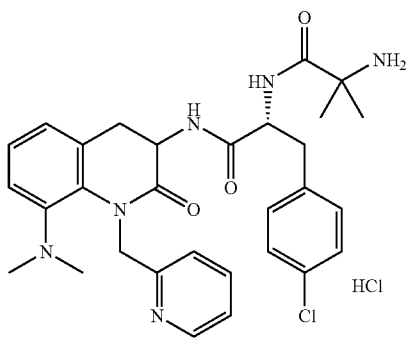

MS(FAB)m/z564(M+H)$^+$
$^1$H-NMR (400 MHz, DMSO-d$_6$):
δ(ppm)1.25(3H, s), 1.44(3H, s), 2.63(6H, br s), 2.80-2.90 (2H, m), 2.98-3.10(2H, m), 3.35-3.48(1H, m), 4.46-4.56(1H, m), 4.76-4.85(1H, m), 5.43(1H, d, J=16.0 Hz), 5.54(1H, d, J=16.0 Hz), 6.87-7.03(3H, m), 7.09-7.17(2H, m), 7.30-7.40 (4H, m), 7.64(1H, t, J=7.5 Hz), 8.04(3H, br s), 8.35(1H, d, J=4.5 Hz), 8.51(1H, d, J=9.0 Hz), 8.71(1H, d, J=7.5 Hz).

Example 46

(2R)-2-(2-Aminoacetamido)-N-[8-(diethylamino)-1-(furan-2-ylmethyl)-2-oxo-1,2,3,4-tetrahydroquinolin-3-yl]-4-methylpentanamide hydrochloride

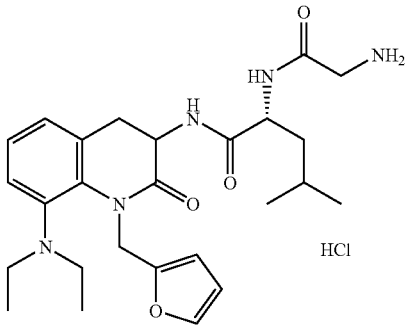

MS(FAB)m/z484(M+H)$^+$
$^1$H-NMR(400 MHz, DMSO-d$_6$):
δ(ppm)0.70-0.88(3H, m), 0.89(3H, d, J=7.0 Hz), 0.90(3H, d, J=7.0 Hz), 1.00-1.20(3H, m), 1.42-1.72(3H, m), 2.70-2.80 (2H, m), 2.85-3.30(4H, m), 3.52-3.65(2H, m), 4.30-4.42(1H, m), 4.50-4.63(1H, m), 5.42(1H, d, J=15.5 Hz), 5.72(1H, d, J=15.5 Hz), 5.92(1H, d, J=3.0 Hz), 6.24(1H, dd, J=2.0, 3.0 Hz), 6.89(1H, d, J=6.5 Hz), 6.97-7.07(2H, m), 7.41(1H, d, J=1.0 Hz), 8.04(3H, br s), 8.56(1H, d, J=8.0 Hz), 8.66(1H, d, J=8.0 Hz).

Example 47

(2R)-2-(3-Amino-3-methylbutanamido)-N-[8-(diethylamino)-2-oxo-1-(pyridin-2-ylmethyl)-1,2,3,4-tetrahydroquinolin-3-yl]-4-methylpentanamide hydrochloride

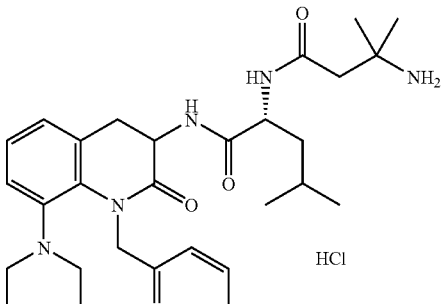

MS(FAB)m/z537(M+H)$^+$
$^1$H-NMR(400 MHz, DMSO-d$_6$):
δ(ppm)0.73-0.83(3H, m), 0.87(3H, d, J=6.5 Hz), 0.90(3H, d, J=6.5 Hz), 0.90-1.02(3H, m), 1.26(3H, s), 1.26(3H, s), 1.41-1.68(3H, m), 2.81-3.19(6H, m), 3.30-3.50(2H, m), 4.38-4.55(2H, m), 5.41(1H, d, J=16.5 Hz), 5.88(1H, d, J=16.5 Hz), 6.92-7.08(3H, m), 7.16(1H, d, J=7.5 Hz), 7.27(1H, br s), 7.79(1H, br s), 8.05(3H, br s), 8.40-8.56(2H, m).

Example 48

(2R,4R)—N-[(2R)-1-[8-(Diethylamino)-2-oxo-1-(pyridin-2-ylmethyl)-1,2,3,4-tetrahydroquinolin-3-ylamino]-4-methyl-1-oxopentan-2-yl]-4-hydroxypyrrolidin-2-carboxamide hydrochloride

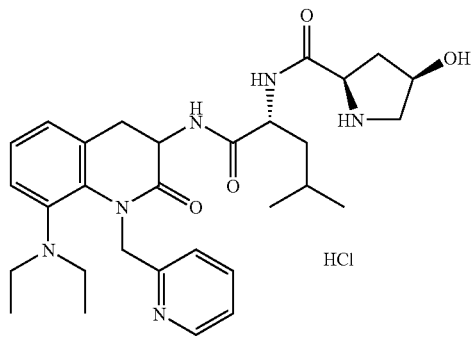

MS(FAB)m/z551(M+H)+

¹H-NMR(400 MHz, DMSO-d₆:

δ(ppm)0.75-0.84(3H, m), 0.89(3H, d, J=7.0 Hz), 0.90(3H, d, J=7.0 Hz), 0.93-1.01(3H, m), 1.45-1.68(3H, m), 1.80-1.90 (1H, m), 2.83(1H, dd, J=5.0, 15.0 Hz), 2.88-3.28(8H, m), 4.16-4.26(1H, m), 4.30-4.38(1H, m), 4.41-4.61(2H, m), 5.23-5.45(1H, br), 5.41(1H, d, J=16.0 Hz), 5.86(1H, d, J=16.0 Hz), 6.92-7.05(3H, m), 7.10(1H, d, J=8.0 Hz), 7.16-7.23(1H, m), 7.63-7.75(1H, m), 8.40(1H, d, J=4.5 Hz), 8.48-8.61(2H, m), 8.65(1H, d, J=8.5 Hz), 9.92(1H, br s).

Example 49

Synthesis of N-[2-oxo-8-(2-oxopyrrolidin-1-yl)-1,2,3,4-tetrahydroquinolin-3-yl]acetamide

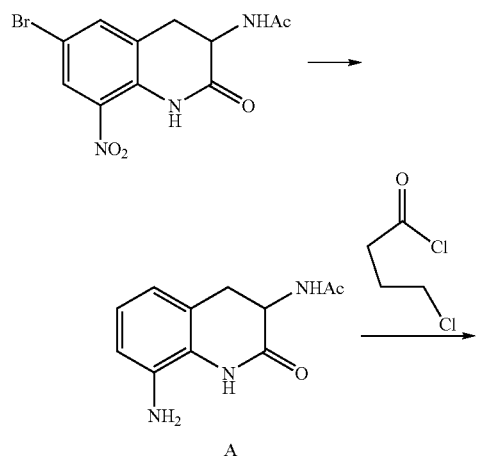

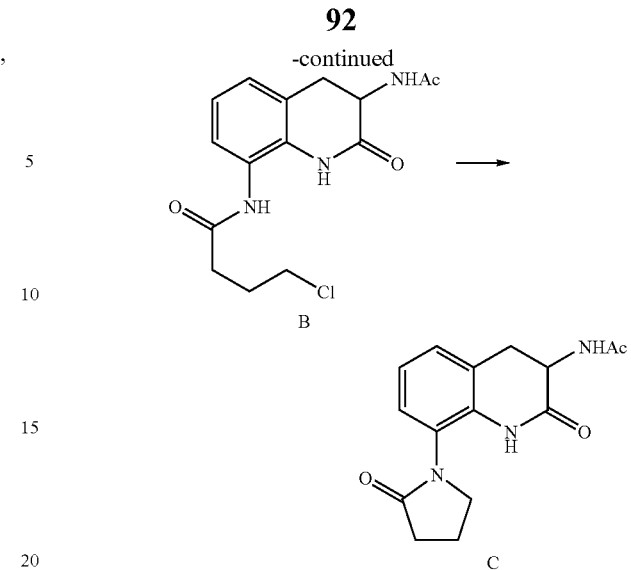

Diisopropylethylamine (258.5 g) was dissolved in N-methylpyrrolidone (1476.6 mL), and the solution was heated at 50° C. To the mixture were added Pd—C (35.06 g) and N-(6-bromo-8-nitro-2-oxo-1,2,3,4-tetrahydroquinolin-3-yl) acetamide (328 g). The reactor was washed with N-methylpyrrolidone (262.5 mL), and the wash liquid was combined with the mixture. The resultant mixture was purged with hydrogen three times, and then stirred vigorously for three hours while maintaining the internal temperature between 70-80° C. (formation of Compound A). The reaction mixture was cooled to 25° C., and then filtered through Celite. The filtered solid was washed with N-methylpyrrolidone (328 mL) twice. To the filtrate was added 4-chlorobutyryl chloride (141.0 g) at room temperature, and the mixture was stirred for 1.5 hours (formation of Compound B). To the resultant mixture was added dropwise 25% aqueous sodium hydroxide solution (480 g) over 10 minutes, and the mixture was stirred for one hour (formation of Compound C). Stirring was continued overnight, and 2-propanol (4.8 L) was added to the resultant mixture, followed by stirring for one hour. The formed precipitates were recovered through vacuum filtration, and the thus-recovered residue was washed with 2-propanol (480 mL×2), whereby the title compound (280.7 g) was yielded as a powdery compound. The powdery compound contained 33.5% of inorganic salts.

Compound B Ms(FAB)m/z310(M+H)+

¹H-NMR(400 MHz, DMSO-d₆):

δ(ppm)1.91(3H, s), 2.07(2H, t, J=6.7 Hz), 2.53(2H, t, J=7.0 Hz), 2.91(1H, t, J=14.4 Hz), 3.04(1H, dd, J=6.3, 14.4 Hz), 3.69(2H, t, J=6.5 Hz), 4.41-4.45(1H, m), 6.92(1H, t, J=7.7 Hz), 7.01(1H, d, J=7.4 Hz), 7.35(1H, d, J=7.4 Hz), 7.84(1H, d, J=7.8 Hz), 9.17(1H, s), 9.34(1H, s).

Compound C Ms(FAB)m/z288(M+H)+

¹H-NMR(400 MHz, DMSO-d₆):

δ(ppm)1.92(3H, s), 2.07-2.19(1H, m), 2.42(1H, t, J=7.8 Hz), 2.90(1H, t, J=15.0 Hz), 3.04(1H, dd, J=6.3, 15.0 Hz), 3.58-3.71(2H, m), 4.41-4.48(1H, m), 6.99(1H, t, J=7.5 Hz), 7.11(1H, d, J=7.5 Hz), 7.17(1H, d, J=7.5 Hz), 8.25(1H, d, J=7.5 Hz), 9.74(1H, s).

Example 50

Synthesis of 3-(bromomethyl)thiophene

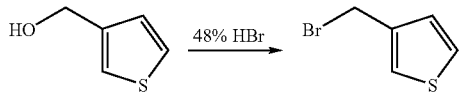

48% Hydrobromic acid (147.6 g) was cooled on ice, and 3-hydroxymethylthiophene (10 g) was added thereto, followed by stirring for 30 minutes. The organic layer was separated, and then washed with saturated aqueous sodium bicarbonate solution. The resultant mixture was subjected to vacuum distillation (4.5 mmHg) at 46-48° C., whereby the title compound (5.2 g) was yielded.

Ms(FAB)m/z178(M+H)$^+$
$^1$H-NMR(400 MHz, DMSO-d$_6$):
δ(ppm)4.72(2H, s), 7.16(1H, dd, J=1.0, 5.0 Hz), 7.55(1H, J=3.0, 5.0 Hz), 7.62(1H, d, J=3.0 Hz).

Example 51

Synthesis of N-(2-oxo-8-(2-oxopyrrolidin-1-yl)-1-(thiophen-3-ylmethyl)-1,2,3,4-tetrahydroquinolin-3-yl)acetamide

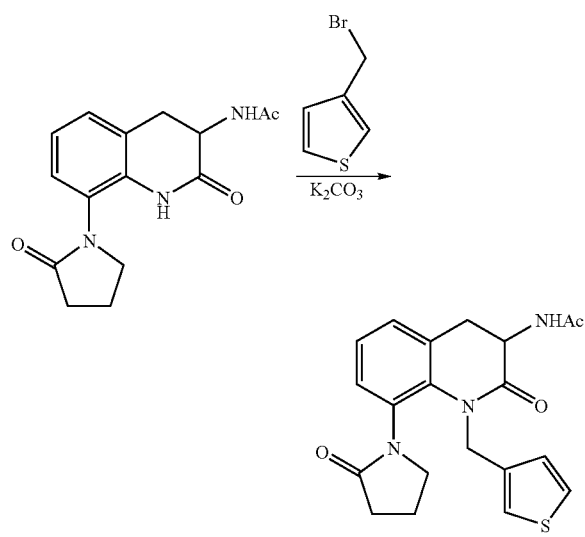

Methyl ethyl ketone (5 mL) was added to a mixture of N-(2-oxo-8-(2-oxopyrrolidin-1-yl)-1,2,3,4-tetrahydroquinolin-3-yl)acetamide (500 mg) and potassium carbonate powder (265 mg), and 3-(bromomethyl)thiophene was added thereto. The mixture was stirred at an internal temperature of 79° C. for 20.5 hours, and then left to stand at room temperature. The mixture was partitioned between saturated aqueous sodium chloride solution (2 mL) and ethyl acetate (1 mL), and the aqueous layer was extracted with ethyl acetate (2 mL+1 mL). The organic layers were combined, and the solvent was evaporated under reduced pressure. Ethyl acetate (1.5 mL) and toluene (2.5 mL) were added to the thus-recovered residue, and the precipitated crystals were recovered through filtration. The container of the reaction mixture was washed with a mixture of ethyl acetate and toluene (3:5) (0.5 mL×2). The thus-recovered crystals were washed with a mixture of ethyl acetate and toluene (3:5) (1.0 mL×2), and then dried under reduced pressure at 60° C., whereby ethyl acetate solvates of the title compound (510 mg) were yielded.

Ms(FAB)m/z384(M+H)$^+$
$^1$H-NMR(400 MHz, DMSO-d$_6$, 80° C.):
δ(ppm)1.92(3H, s), 1.95-2.07(2H, m), 2.22-2.39(2H, m), 2.75(1H, t, J=14.4 Hz), 2.93(1H, dd, J=5.1, 14.4 Hz), 3.34-3.40(1H, m), 3.72-3.79(1H, m), 4.41-4.47(1H, m), 4.57(1H, d, J=15.6 Hz), 5.17(1H, d, J=15.7 Hz), 6.79(1H, dd, J=1.0, 4.9 Hz), 7.03(1H, dd, J=1.0, 2.6 Hz), 7.10(1H, t, J=7.6 Hz), 7.15-7.17(2H, m), 7.32(1H, dd, J=3.0, 4.9 Hz), 7.87(1H, d, J=6.8 Hz).

Example 52

Synthesis of 3-amino-8-(2-oxopyrrolidin-1-yl)-1-(thiophen-3-ylmethyl)-3,4-dihydroquinolin-2(1H)-one

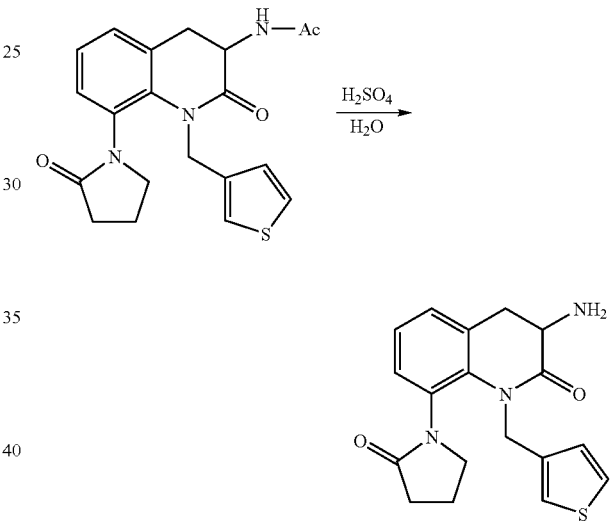

Sulfuric acid (470.6 mL) was added to water (5.65 L) at room temperature, and N-(2-oxo-8-(2-oxopyrrolidin-1-yl)-1-(thiophen-3-ylmethyl)-1,2,3,4-tetrahydroquinolin-3-yl)acetamide (561.5 g) was added thereto at an internal temperature of 41-43° C. The mixture was heated at an internal temperature of 80 to 92° C. for four hours while being stirred. Under cooling on ice, 25% sodium hydroxide (2,715 g) was added dropwise to the reaction mixture at an internal temperature of 50° C. or lower, to thereby adjust the pH of the mixture to 7. Ethyl acetate (1.0 L) was added to the resultant mixture while being stirred, and 25% sodium hydroxide (300 g) was added thereto at an internal temperature of 50° C. or lower, to thereby adjust the pH of the mixture to 10. An additional ethyl acetate (1.83 L) was added to the mixture, and stirring was performed for five minutes, to thereby partition the mixture. Ethyl acetate (2.83 L) was added to the aqueous layer at an internal temperature of 30° C. or lower, and stirring was performed for five minutes, to thereby partition the mixture. An additional ethyl acetate (2.83 L) was added to the aqueous layer, and the above-described extraction procedure was repeated. The ethyl acetate layers were combined, and the combined ethyl acetate layer was concentrated under reduced pressure, to thereby evaporate ethyl acetate (6.8 L). The reaction mixture was left to stand overnight in a refrigerator, and the crystals that precipitated were recovered through filtration. The thus-recovered crystals were washed with ethyl acetate (566 mL). The thus-obtained solid was dried in air overnight and then at 60° C. under reduced pressure, whereby the title compound (389.2 g) was yielded as pale yellow crystals.

Example 53

Synthesis of tert-butyl (2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylcarbamate

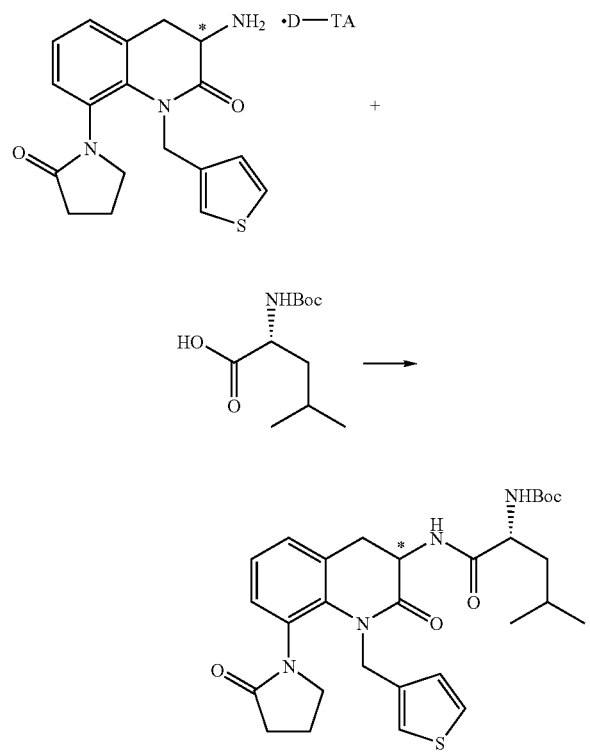

N-tert-Butoxycarbonyl-D-leucine monohydrate (25.00 g) was dissolved in tetrahydrofuran (224 mL), and triethylamine (20.30 g) and isobutyl chlorocarbonate (13.06 g) were sequentially added thereto at 5° C. or lower under cooling on ice. To the mixture was added 3-amino-8-(2-oxopyrrolidin-1-yl)-1-(thiophen-3-ylmethyl)-3,4-dihydroquinolin-2(1H)-one D-(−)-tartrate (44.80 g) in an aqueous sodium hydroxide solution (a mixture of 25% aqueous sodium hydroxide solution (14.58 g) and water (89.6 g)) at 5° C. or lower. The mixture was stirred for 10 minutes under cooling on ice, and then the temperature was raised to room temperature. Saturated aqueous sodium chloride solution (44.8 g) was added to the reaction mixture to partition the mixture, and the aqueous layer was further extracted with tetrahydrofuran (224 mL). The organic layers were combined, and the combined organic layer was concentrated to half volume, whereby a solution of the title compound in tetrahydrofuran was yielded.

Example 54

Synthesis of (2R)-2-amino-4-methyl-N-[2-oxo-8-(2-oxopyrrolidin-1-yl)-1-(thiophen-3-ylmethyl)-1,2,3,4-tetrahydroquinolin-3-yl]pentanamide

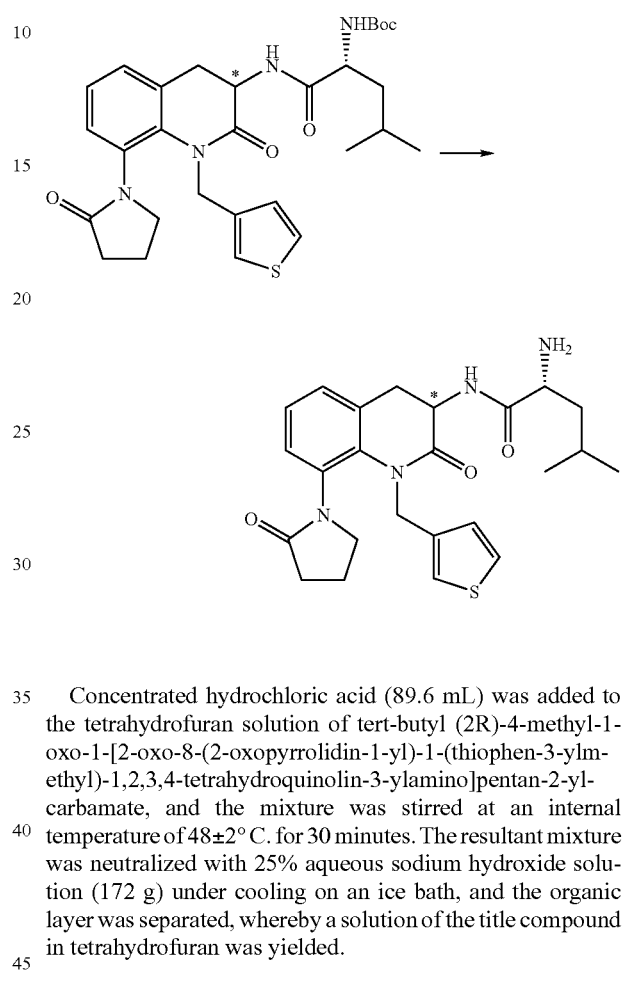

Concentrated hydrochloric acid (89.6 mL) was added to the tetrahydrofuran solution of tert-butyl (2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylcarbamate, and the mixture was stirred at an internal temperature of 48±2° C. for 30 minutes. The resultant mixture was neutralized with 25% aqueous sodium hydroxide solution (172 g) under cooling on an ice bath, and the organic layer was separated, whereby a solution of the title compound in tetrahydrofuran was yielded.

Example 55

Synthesis of tert-butyl 2-methyl-1-[(2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylamino]-1-oxopropan-2-ylcarbamate

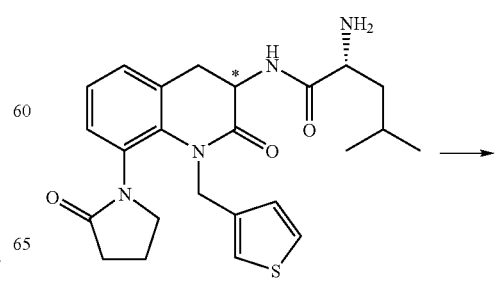

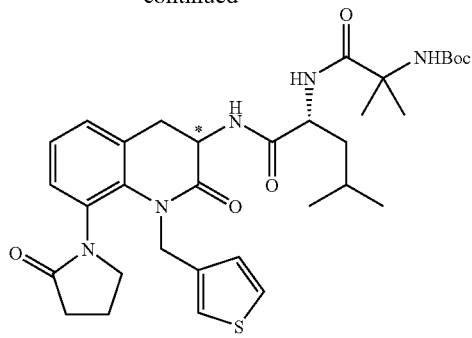

To the tetrahydrofuran solution of (2R)-2-amino-4-methyl-N-[2-oxo-8-(2-oxopyrrolidin-1-yl)-1-(thiophen-3-ylmethyl)-1,2,3,4-tetrahydroquinolin-3-yl]pentanamide were sequentially added 2-(tert-butoxycarbonylamino)-2-methylpropanoic acid (20.4 g), 1-hydroxybenzotriazole (15.3 g), and 1-ethyl-3-(3-dimethylaminopropyl)carbodiimide hydrochloride (19.2 g) under cooling on ice, and the mixture was stirred at room temperature for two hours. Saturated aqueous sodium chloride solution was added to the resultant mixture, and the organic layer was separated, whereby a solution of the title compound in tetrahydrofuran was yielded.

Example 56

Synthesis of (2R)-2-(2-amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide

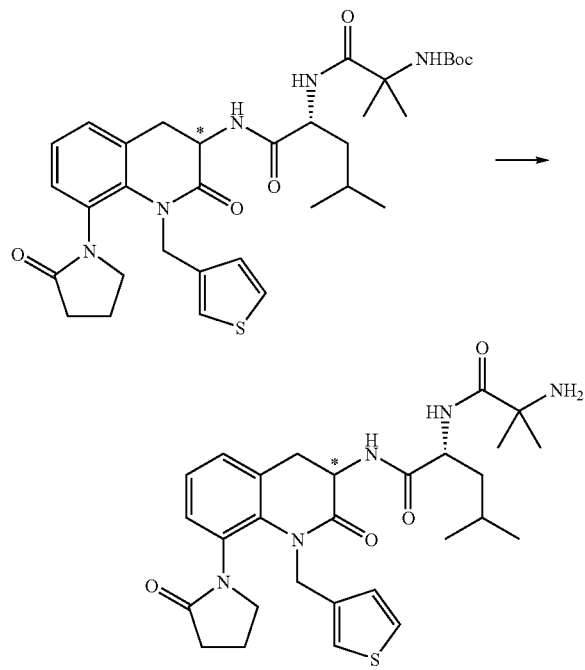

Concentrated hydrochloric acid (89.6 mL) was added to the tetrahydrofuran solution of tert-butyl 2-methyl-1-[(2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylamino]-1-oxopropan-2-ylcarbamate, and the mixture was stirred at an internal temperature of 48±2° C. for 30 minutes. The mixture was neutralized with 25% aqueous sodium hydroxide solution (172 g) under cooling on an ice bath. The organic layer was separated, and then concentrated under reduced pressure, whereby the title compound (49.36 g) was yielded.

Example 57

Synthesis of (2R)-2-(2-amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (R)-(−)-mandelate

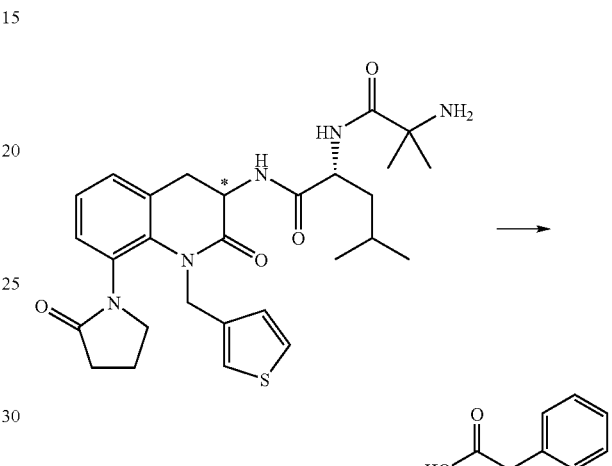

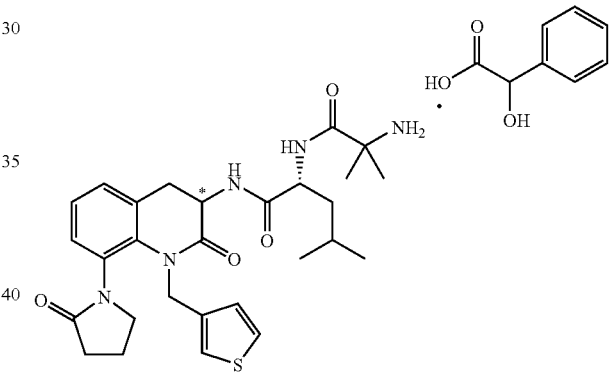

(2R)-2-(2-Amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (540 mg) was dissolved in toluene (5.4 mL), and a solution of D-(−)-mandelic acid (152 mg) in isopropanol (1.6 mL) was added thereto, followed by stirring at room temperature for 18 hours. The formed precipitates were recovered through filtration, washed with a mixture of toluene and isopropanol (1:1), and dried under reduced pressure, whereby the title compound (502 mg) was yielded.

Example 58

Synthesis of N-(8-nitro-2-oxo-1,2,3,4-tetrahydroquinolin-3-yl)acetamide

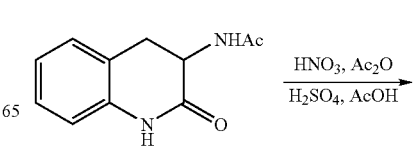

-continued

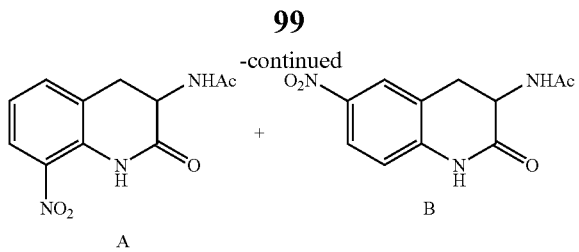

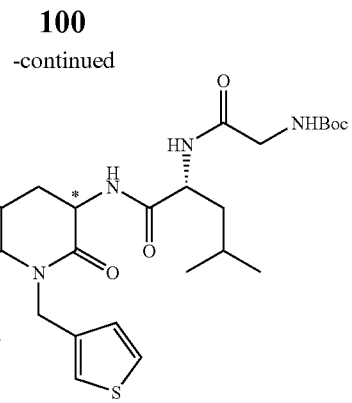

Fuming nitric acid (2 mL) was added dropwise to acetic anhydride (81 mL) at an internal temperature of 8° C. or lower, and sulfuric acid (81 μL) and a solution of N-(2-oxo-1,2,3,4-tetrahydroquinolin-3-yl)acetamide (8.1 g) in acetic acid (81 mL) were sequentially added thereto, followed by stirring at room temperature for 3.5 hours. Diisopropyl ether (162 mL) was added to the mixture, and stirring was performed under cooling on ice for 30 minutes. The formed precipitates were recovered through filtration, washed with diisopropyl ether, and dried under reduced pressure, whereby a mixture of the title compound (A) and N-(8-nitro-2-oxo-1,2,3,4-tetrahydroquinolin-3-yl)acetamide (B) (A:B=1:1) (7.15 g) was yielded.

Compound A

MS(FAB)m/z250(M+H)$^+$ $^1$H-NMR(400 MHz, DMSO-d$_6$):

δ(ppm)1.92(3H, s), 3.04(1H, t, J=15.2 Hz), 3.21(1H, dd, J=5.1, 15.2 Hz), 4.59-4.65(1H, m), 7.18(1H, t, J=7.4 Hz), 7.66(1H, d, J=7.4 Hz), 8.02(1H, d, J=8.4 Hz), 8.34(1H, d, J=8.0 Hz), 9.99(1H, s).

Compound B

MS(FAB)m/z250(M+H)$^+$ $^1$H-NMR(400 MHz, DMSO-d$_6$:

δ(ppm)1.91(3H, s), 2.99(1H, t, J=15.1 Hz), 3.21(1H, dd, J=6.5, 15.1 Hz), 4.54-4.61(1H, m), 7.03(1H, d, J=10.7 Hz), 8.11(1H, dd, J=2.5, 8.8 Hz), 8.17(1H, d, J=2.5 Hz), 8.28(1H, d, J=8.8 Hz), 10.92(1H, s).

Example 59

Synthesis of tert-butyl 2-methyl-1-[(2R)-4-methyl-1-oxo-1-[2-oxo-8-(2-oxopyrrolidin-1-yl)-1-(thiophen-3-ylmethyl)-1,2,3,4-tetrahydroquinolin-3-ylamino]pentan-2-ylamino]-1-oxopropan-2-ylcarbamate

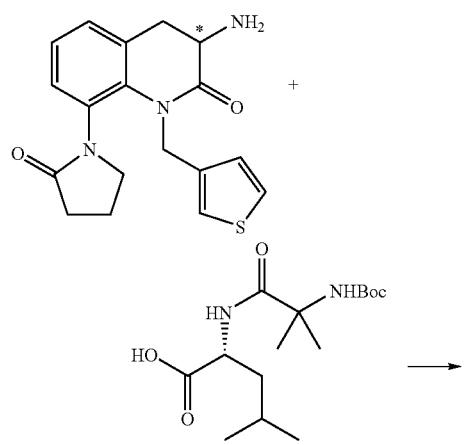

3-Amino-8-(2-oxopyrrolidin-1-yl)-1-(thiophen-3-ylmethyl)-3,4-dihydroquinolin-2(1H)-one (200 mg) and (R)-2-(2-(tert-butoxycarbonylamino)-2-methylpropanamido)-4-methylpentanoic acid (200 mg) were dissolved in dichloromethane (2 mL), and to the solution was added dropwise a solution of 1-ethyl-3-(3-dimethylaminopropyl)carbodiimide hydrochloride (126 mg), 3-hydroxy-4-oxo-3,4-dihydro-1,2,3-benzotriazine (107 mg), and triethylamine (42 μL) in dichloromethane (2 mL) over 10 minutes under cooling on ice, followed by stirring at room temperature for 18 hours. The solvent was evaporated, and the thus-recovered residue was dissolved in ethyl acetate. The solution was sequentially washed with saturated aqueous sodium bicarbonate solution and saturated aqueous sodium chloride solution, and the organic layer was dried over sodium sulfate. The solvent was evaporated under reduced pressure, and the thus-recovered residue was purified through silica gel column chromatography (hexane:ethyl acetate (1:1), chloroform:methanol (10:1)), whereby the title compound (342 mg) was yielded.

Example 60

Synthesis of (R)-2-(2-(tert-butoxycarbonylamino)-2-methylpropanamido)-4-methylpentanoic Acid Methyl Ester

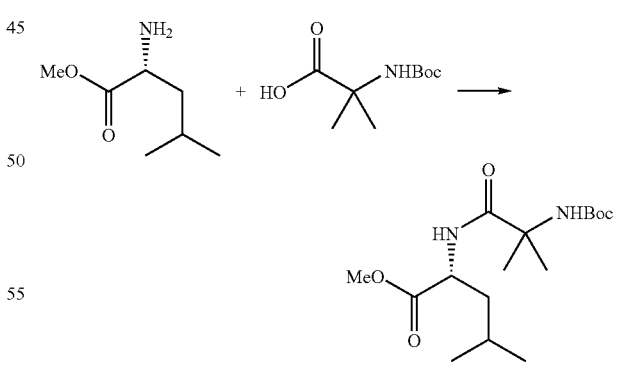

2-(tert-Butoxycarbonylamino)-2-methylpropanoic acid (22.4 g) and D-leucine methyl ester hydrochloride (20.0 g) were dissolved in N,N-dimethylformamide (224 mL), and triethylamine (11.1 g) was added dropwise thereto under cooling on ice. To the mixture were sequentially added 1-hydroxybenzotriazole (14.9 g) and 1-ethyl-3-(3-dimethylaminopropyl)carbodiimide hydrochloride (19.1 g), and stirring was performed for two hours. Water (224 mL) was added to the reaction mixture, and the formed precipitates were recovered through filtration, whereby the title compound (57.8 g) was yielded as wet crystals.

¹H-NMR(400 MHz, DMSO-d₆):
δ(ppm)0.83(6H, dd, J=6.3, 16.1 Hz), 1.28(3H, s), 1.29 (3H, s), 1.36(9H, s), 1.41-1.45(1H, m), 1.58-1.68(2H, m), 3.59(3H, s), 4.23-4.29(1H, m), 6.78(1H, s), 7.68(1H, d, J=8.0 Hz).

Example 61

Synthesis of (R)-2-(2-(tert-butoxycarbonylamino)-2-methylpropanamido)-4-methylpentanoic Acid

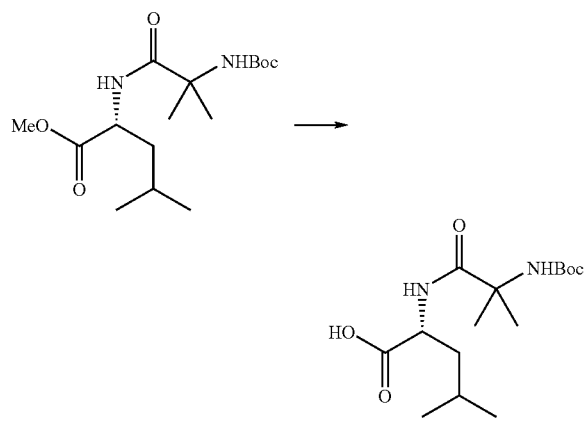

(R)-2-(2-(tert-Butoxycarbonylamino)-2-methylpropanamido)-4-methylpentanoic acid methyl ester as wet crystals (57.8 g) (dry weight: 36.3 g) was suspended in tert-butyl methyl ether (182 g), and 25% aqueous sodium hydroxide solution (52.8 g) was added dropwise thereto. The mixture was heated at 40° C. on an oil bath while being stirred for 20 minutes. The reaction mixture was neutralized with concentrated hydrochloric acid (27.5 mL) under cooling on ice. The organic layer was separated, washed with saturated aqueous sodium chloride solution, and dried over sodium sulfate. The solvent was evaporated, whereby the title compound (22.2 g) was yielded.

¹H-NMR(400 MHz, DMSO-d₆:
δ(ppm)0.83(6H, dd, J=6.5, 13.9 Hz), 1.29(3H, s), 1.30 (3H, s), 1.36(9H, s), 1.41-1.49(1H, m), 1.56-1.69(2H, m), 4.18-4.24(1H, m), 6.82(1H, s), 7.46(1H, d, J=8.0 Hz), 12.35 (1H, br s).

Example 62

Synthesis of tert-butyl 6-bromo-8-nitro-2-oxo-1,2,3,4-tetrahydroquinolin-3-ylcarbamate

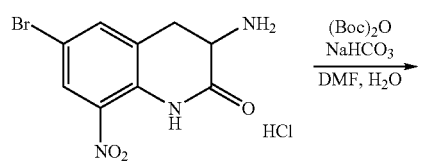

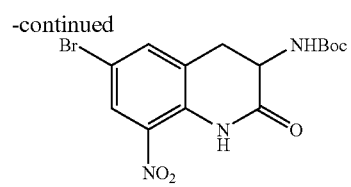

3-Amino-6-bromo-8-nitro-3,4-dihydroquinolin-2(1H)-one hydrochloride (1.08 g) was added to N,N-dimethylformamide (9.8 mL), and a solution of sodium bicarbonate (518 mg) in water (6.5 mL) was added dropwise thereto under cooling on ice. Subsequently, (Boc)₂O (706 mg) was added to the mixture, and stirring was performed at room temperature for 24 hours. The formed precipitates were recovered through filtration, washed with water, and dried under reduced pressure, whereby the title compound (1.1 g) was yielded as a powdery compound.

Example 63

Synthesis of tert-butyl 2-oxo-8-(2-oxopyrrolidin-1-yl)-1,2,3,4-tetrahydroquinolin-3-ylcarbamate

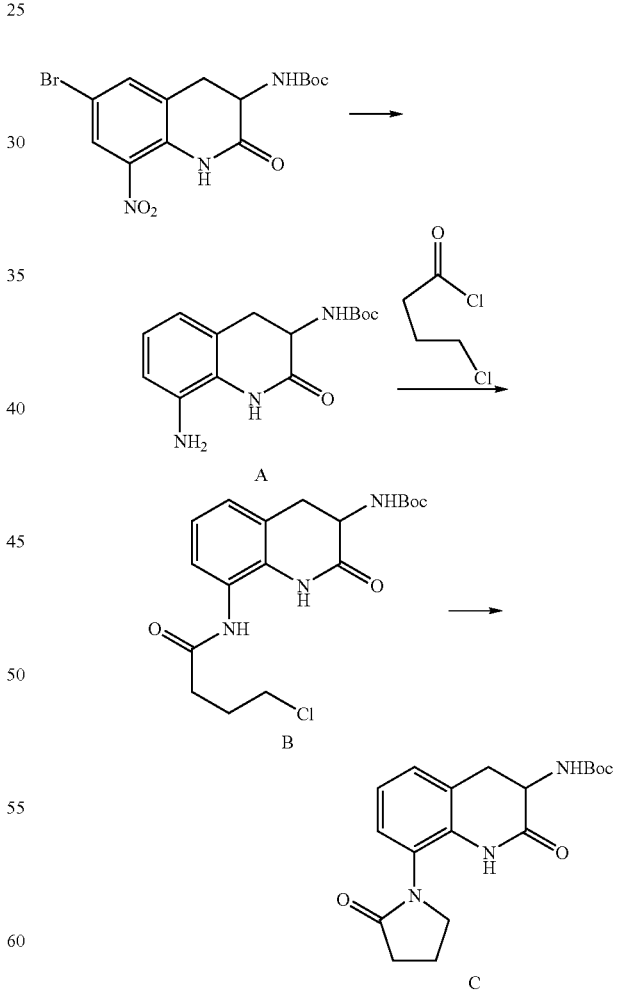

tert-Butyl 6-bromo-8-nitro-2-oxo-1,2,3,4-tetrahydroquinolin-3-ylcarbamate (200 g) was suspended in N-methylpyrrolidone (520 mL), and diisopropylethylamine (136.6 g) and 10% Pd—C (water content: 52.5%) (12.6 g) were added thereto. The reactor was washed with N-methylpyrrolidone (200 mL), and the wash liquid was combined with the mixture. The resultant mixture was purged with hydrogen three times, and the mixture was stirred vigorously for four hours while maintaining the internal temperature at 50-56° C. (formation of Compound A). The resultant mixture was cooled to 25° C., and the mixture was filtered through Celite. The filtered solid was washed with N-methylpyrrolidone (20 mL) three times. The filtrate was cooled to 8° C., and 4-chlorobutyryl chloride (80.3 g) was added dropwise thereto, followed by stirring at 14-17° C. for 20 minutes (formation of Compound B). To the resultant mixture was added dropwise 25% aqueous sodium hydroxide solution (265.2 g) over 12 minutes, and the mixture was stirred for 1.5 hours (formation of Compound C). Water (720 mL) was added to the resultant mixture, and stirring was continued for one hour. The formed precipitates were recovered through vacuum filtration, and the thus-recovered residue was washed three times with water (200 mL), whereby the title compound (154 g) (water content: 14%) was yielded as a powdery compound.

Example 64

Synthesis of tert-butyl 2-oxo-8-(2-oxopyrrolidin-1-yl)-1-(thiophen-3-ylmethyl)-1,2,3,4-tetrahydroquinolin-3-ylcarbamate

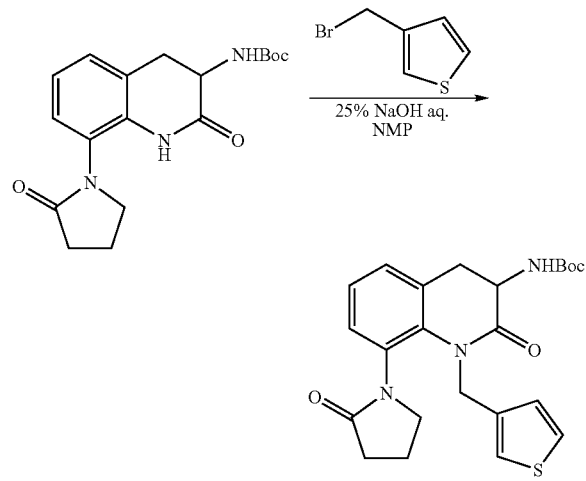

t-Butyl 2-oxo-8-(2-oxopyrrolidin-1-yl)-1,2,3,4-tetrahydroquinolin-3-ylcarbamate (128 g) (water content: 14%) was added to N-methylpyrrolidone (308 mL). The reactor was washed with N-methylpyrrolidone (88 mL), and the wash liquid was combined with the mixture. To the resultant mixture was added dropwise 25% aqueous sodium hydroxide solution (56 g) under cooling on ice. The reactor was washed with N-methylpyrrolidone (22 mL), and the wash liquid was combined with the mixture. Subsequently, 3-bromomethylthiophene (62 g) was added dropwise to the mixture. The reactor was washed with N-methylpyrrolidone (22 mL), and the wash liquid was combined with the mixture. The resultant reaction mixture was stirred at 14-22° C. for one hour, and water (880 mL) was added thereto under cooling on ice, followed by stirring for 30 minutes. The formed precipitates were recovered through filtration, and the thus-recovered residue was washed four times with water (110 mL) and once with toluene (110 mL). Toluene (1120 mL) was added to the thus-obtained powdery solid, and the mixture was heated at 80 to 89° C. to dissolve the solid matter. Subsequently, the mixture was filtered while being heated, and the filtrate was stirred at room temperature for 20 minutes. The formed precipitates were recovered through filtration, washed with toluene (70 mL), and dried under reduced pressure, whereby the title compound (145 g) (toluene content: 8%) was yielded as a powdery compound.

Example 65

Synthesis of 3-amino-8-(2-oxopyrrolidin-1-yl)-1-(thiophen-3-ylmethyl)-3,4-dihydroquinolin-2(1H)-one

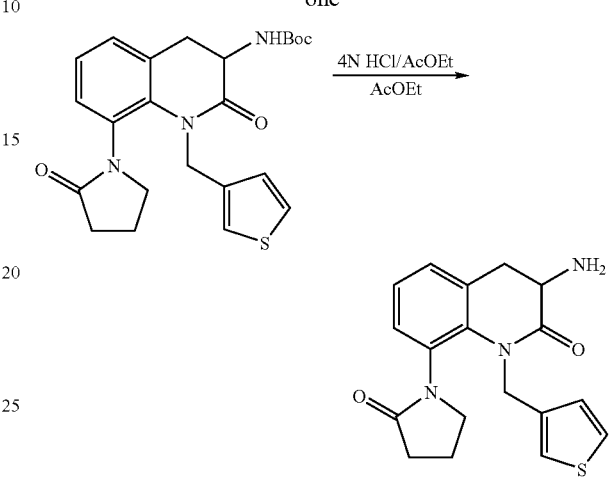

tert-Butyl 2-oxo-8-(2-oxopyrrolidin-1-yl)-1-(thiophen-3-ylmethyl)-1,2,3,4-tetrahydroquinolin-3-ylcarbamate (5.0 g) was suspended in ethyl acetate (30 mL), and 4N hydrochloric acid in ethyl acetate (28.3 mL) was added thereto, followed by stirring at 35-40° C. for one hour. The reaction mixture was added to a solution of potassium bicarbonate (11.3 g) in water (20 mL), and the mixture was partitioned at 45° C. The aqueous layer was extracted with ethyl acetate twice, and the organic layers were combined. The combined organic layer was concentrated under reduced pressure until precipitates were formed. The concentrated residue was stirred at room temperature for 30 minutes, and the formed precipitates were recovered through filtration. The thus-obtained solid was washed with ethyl acetate, and then dried under reduced pressure, whereby the title compound (2.93 g) was yielded as crystals.

Example 66

Synthesis of (2R)-2-(2-amino-2-methylpropanamido)-N-(8-(2-hydroxy-5-oxopyrrolidin-1-yl)-2-oxo-1-(thiophen-3-ylmethyl)-1,2,3,4-tetrahydroquinolin-3-yl)-4-methylpentanamide

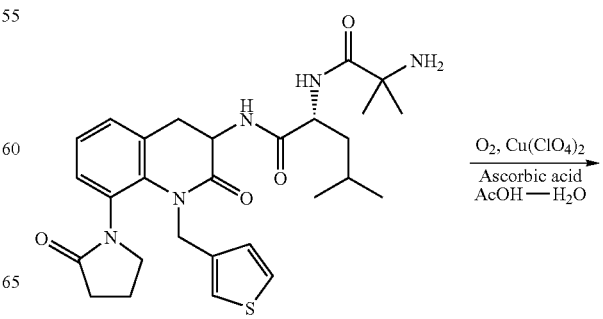

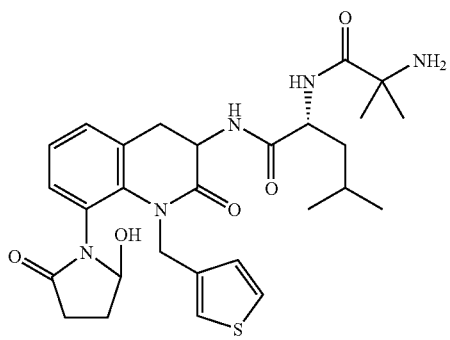

(2R)-2-(2-Amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (1.08 g) was dissolved in acetic acid (30 mL), and a solution of L-(+)-ascorbic acid (3.52 g) and Cu(ClO$_4$)$_2$.6H$_2$O (741 mg) in water (40 mL) was added thereto, followed by stirring at room temperature for 15 minutes while oxygen gas was bubbled into the mixture. Saturated aqueous sodium chloride solution was added to the reaction mixture, and the mixture was washed with ethyl acetate twice. Sodium bicarbonate (88.2 g) was added to the aqueous layer, and the mixture was extracted with chloroform twice. The organic layer was concentrated under reduced pressure, and the thus-recovered residue was purified through chromatography, whereby the title compound (0.5 mg) was yielded.

MS(FAB)m/z557(M+H)$^+$ $^1$H-NMR 400 MHz, CDCl$_3$, 50° C.):

δ(ppm) δ(ppm)0.95(3H, d, J=6.5 Hz), 0.98(3H, d, J=6.5 Hz), 1.33(3H, s), 1.35(3H, s), 1.38-1.92(7H, m), 2.22-2.33(1H, m), 2.55-2.68(2H, m), 3.22(1H, dd, J=5.0, 14.5 Hz), 3.30-3.60(1H, m), 4.42(1H, dt, J=5.5, 8.5 Hz), 4.53(1H, dt, J=5.5, 14.0 Hz), 4.80 (1H, d, J=14.5 Hz), 5.05(1H, d, J=14.5 Hz), 5.21-5.31(1H, m), 6.87(1H, dd, J=1.5, 5.0 Hz), 7.00-7.04(1H, m), 7.14-7.22(3H, m), 7.24-7.38(2H, m), 7.94(1H, d, J=8.5 Hz).

Example 67

Synthesis of tert-butyl 1-((2R)-1-(8-(2,5-dioxopyrrolidin-1-yl)-2-oxo-1-(thiophen-3-ylmethyl)-1,2,3,4-tetrahydroquinolin-3-ylamino)-4-methyl-1-oxopentan-2ylamino)-2-methyl-1-oxopropan-2-ylcarbamate

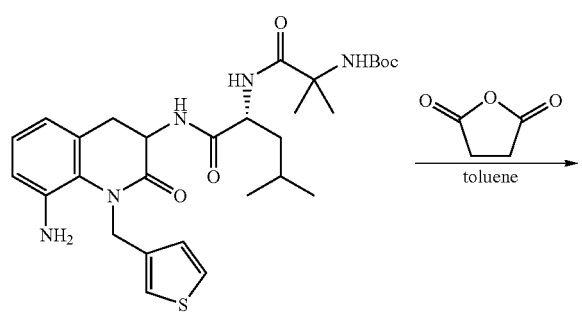

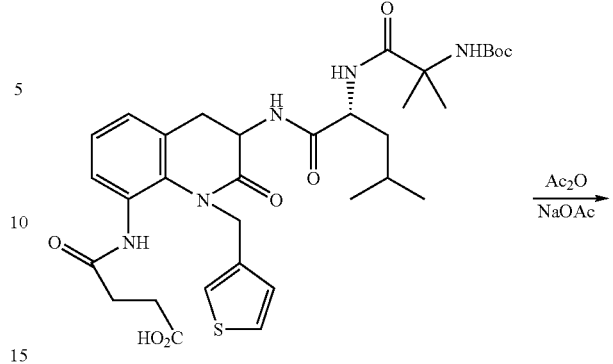

A

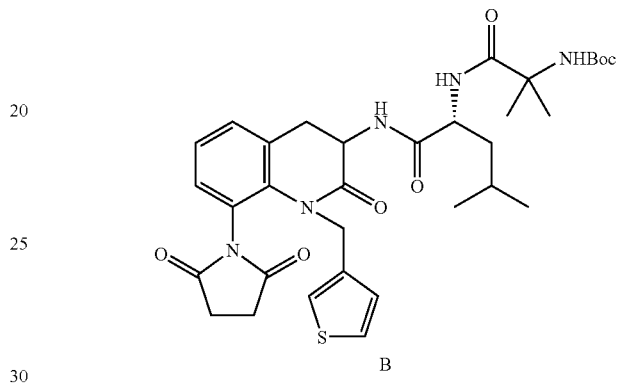

B tert-Butyl 1-((2R)-1-(8-amino-2-oxo-1-(thiophen-3-ylmethyl)-1,2,3,4-tetrahydroquinolin-3-ylamino)-4-methyl-1-oxopentan-2-ylamino)-2-methyl-1-oxopropan-2-ylcarbamate (100 mg) and succinic anhydride (21 mg) were added to toluene (1 mL), and the mixture was refluxed for two hours while being stirred. The reaction mixture was concentrated under reduced pressure, and the thus-recovered residue was purified through silica gel column chromatography (ethyl acetate, chloroform:methanol (5:1)), whereby the Compound A (114 mg) was yielded. The Compound A (110 mg), sodium acetate (75 mg), and acetic anhydride (1 mL) were added to toluene (1 mL), and the mixture was stirred at 80° C. for 20 minutes. The mixture was cooled to room temperature, and water was added thereto. The mixture was extracted with ethyl acetate twice, and the organic layers were combined. The combined organic layer was dried over sodium sulfate, and the solvent was evaporated under reduced pressure, whereby the title compound (100 mg) was yielded.

Compound A

MS(FAB)m/z672(M+H)$^+$ $^1$H-NMR(400 MHz, DMSO-d$_6$):

δ(ppm)0.85(d, 3H, J=6.5 Hz), 0.88(d, 3H, J=6.6 Hz), 1.33(s, 3H), 1.35(s, 3H), 1.37(s, 9H), 1.49-1.71(m, 3H), 2.48-2.53(m, 4H), 2.71(t, 1H, J=14.8 Hz), 2.85(dd, 1H, J=5.1, 15.0 Hz), 4.28-4.38(m, 2H), 4.76(d, 1H, J=15.5 Hz), 5.30(d, 1H, J=15.5 Hz), 6.73(s, 1H), 6.74(dd, 1H, J=1.2, 5.0 Hz), 7.00-7.07(m, 2H), 7.24(dd, 1H, J=3.0, 6.8 Hz), 7.27(dd, 1H, J=3.0, 5.0 Hz), 7.33 (d, 1H, J=8.1 Hz), 7.83(d, 1H, J=7.1 Hz), 9.43(s, 1H), 11.5(br s, 1H).

Compound B

MS(FAB)m/z654(M+H)$^+$ $^1$H-NMR(400 MHz, DMSO-d$_6$):

δ(ppm) 0.83(d, 3H, J=6.3 Hz), 0.87(d, 3H, J=6.4 Hz), 1.29(s, 3H), 1.31(s, 3H), 1.35(s, 9H), 1.43-1.53(m, 1H), 1.55-1.78(m, 3H), 2.26-2.37(m, 1H), 2.42-2.50(m, 1H), 2.64-2.73

(m, 1H), 2.97(m, 2H), 4.30-4.51(m, 3H), 4.78(d, 1H, J=16.0 Hz), 6.76(dd, 1H, J=1.0, 4.8 Hz), 6.94(d, 1H, J=1.5 Hz), 7.01(br s, 1H), 7.12(dd, 1H, J=1.3, 7.9 Hz), 7.22(t, 1H, J=7.6 Hz), 7.41(d, 1H, J=6.5 Hz), 7.47(dd, 1H, J=3.0, 4.9 Hz), 7.62(br s, 1H), 8.15(br s, 1H).

Example 68

Synthesis of (2R)-2-(2-amino-2-methylpropanamido)-N-(8-(2,5-dioxopyrrolidin-1-yl)-2-oxo-1-(thiophen-3-ylmethyl)-1,2,3,4-tetrahydroquinolin-3-yl)-4-methylpentanamide

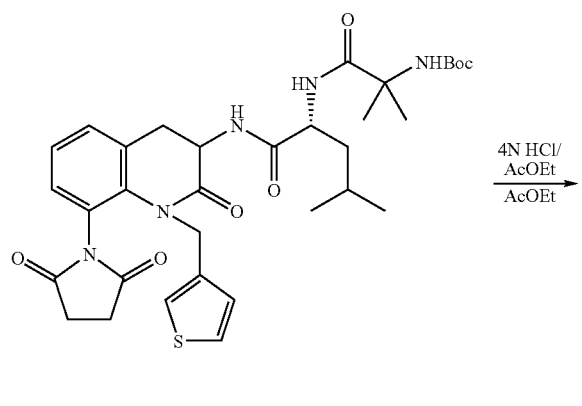

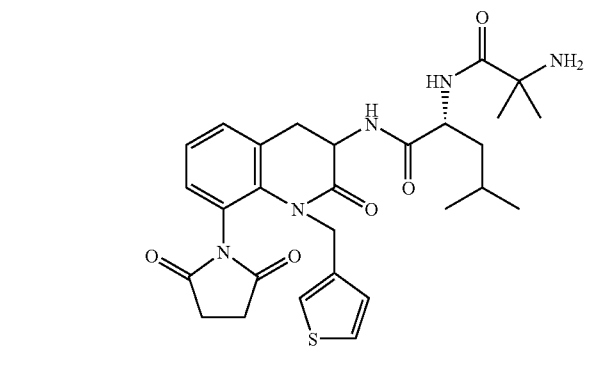

tert-Butyl 1-((2R)-1-(8-(2,5-dioxopyrrolidin-1-yl)-2-oxo-1-(thiophen-3-ylmethyl)-1,2,3,4-tetrahydroquinolin-3-ylamino)-4-methyl-1-oxopentan-2-ylamino)-2-methyl-1-oxopropan-2-ylcarbamate (30 mg) was added to ethyl acetate (0.3 mL), and 4N hydrochloric acid in ethyl acetate (230 μL) was added thereto, followed by stirring at 50° C. for six hours. Saturated aqueous sodium bicarbonate solution was added to the reaction mixture, and the mixture was extracted with ethyl acetate twice. The organic layers were combined, and the combined organic layer was dried over sodium sulfate. The solvent was evaporated under reduced pressure, whereby the title compound (17 mg) was yielded.

MS(FAB)m/z554(M+H)+

$^1$H-NMR(400 MHz, CDCl$_3$, 50° C.):

δ(ppm)0.94(d, 3H, J=7.0 Hz), 0.96(d, 3H, J=6.9 Hz), 1.36 (s, 3H), 1.38(s, 3H), 1.48(s 2H), 1.53-1.85(m, 4H), 2.25(ddd, 1H, J=3.8, 9.8, 18.2 Hz), 2.40(ddd, 1H, J=3.9, 9.8, 18.2 Hz), 2.58(ddd, 1H, J=4. 8, 10.0, 13.4 Hz), 2.76(t, 1H, J=14.0 Hz), 3.48(dd, 1H, J=5.3, 15.1 Hz), 4.37(d, 1H, J=16.5 Hz), 4.43-4.49(m, 1H), 4.67(dt, 1H, J=5.3, 13.4 Hz), 5.04(d, 1H, J=16.3 Hz), 6.85(dd, 1H, J=1.0, 5.0 Hz), 6.90(d, 1H, J=7.9 Hz), 6.93-6.97(m, 1H), 7.19(t, 1H, J=7.7 Hz), 7.22(br s, 1H), 7.25-7.31(m, 1H), 7.91(d, 1H, J=8.3 Hz).

Example 69

Synthesis of (2R)-2-(2-amino-2-methylpropanamido)-N-(8-(2,5-dioxopyrrolidin-1-yl)-2-oxo-1-(thiophen-3-ylmethyl)-1,2,3,4-tetrahydroquinolin-3-yl)-4-methylpentanamide hydrochloride

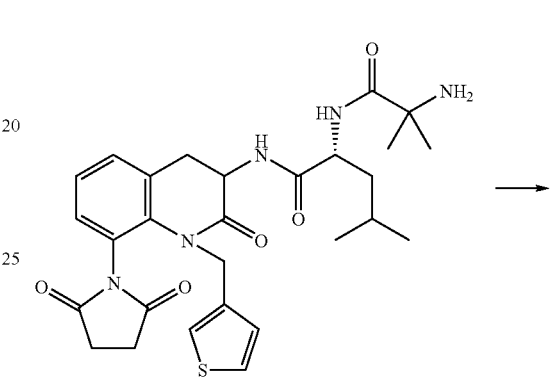

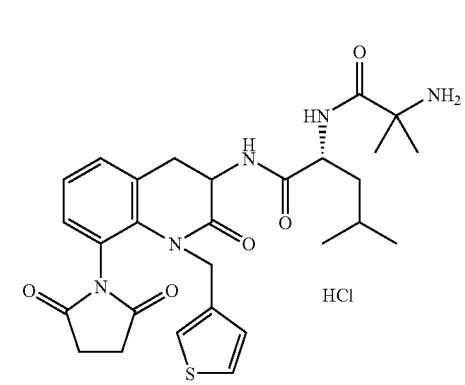

(2R)-2-(2-Amino-2-methylpropanamido)-N-(8-(2,5-dioxopyrrolidin-1-yl)-2-oxo-1-(thiophen-3-ylmethyl)-1,2,3,4-tetrahydroquinolin-3-yl)-4-methylpentanamide (14 mg) was dissolved in ethanol (1 mL), and concentrated hydrochloric acid (35% aqueous hydrochloric acid solution) (25 μL) was added thereto. The solvent was evaporated under reduced pressure, whereby the title compound (16 mg) was yielded.

$^1$H-NMR(400 MHz, DMSO-d$_6$):

δ(ppm)0.87(d, 3H, J=6.3 Hz), 0.91(d, 3H, J=6.3 Hz), 1.48 (s, 3H), 1.50(s, 3H), 1.52-1.82(m, 4H), 2.28-2.37(m, 1H), 2.43-2.52(m, 1H), 2.65-2.74(m, 1H), 2.98(d, 2H, J=9.5 Hz), 4.41-4.62(m, 3H), 4.79(d, 1H, J=16.7 Hz), 6.77(dd, 1H, J=1.2, 5.0 Hz), 6.95-6.98(m, 1H), 7.13(dd, 1H, J=1.4, 7.9 Hz), 7.23(t, 1H, J=7.6 Hz), 7.39-7.43(m, 1H), 7.48(dd, 1H, J=2.9, 4.9 Hz), 8.17(br s, 3H), 8.38(d, 1H, J=8.6 Hz), 8.50(d, 1H, J=7.7 Hz).

Example 70

Synthesis of (2R)-2-(2-amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide hydrochloride

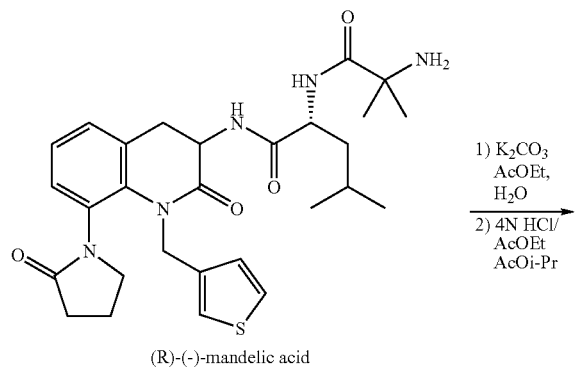

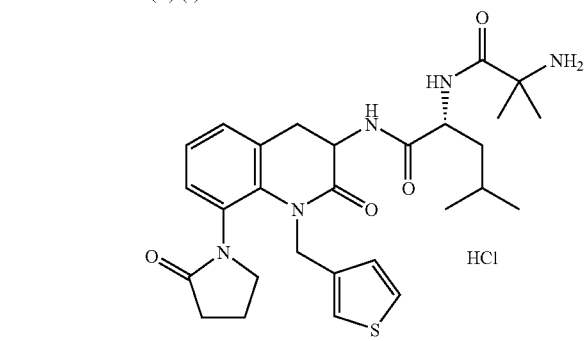

Potassium carbonate (46.7 g) was dissolved in water (585 mL), and ethyl acetate (500 mL) and (2R)-2-(2-amino-2-methylpropanamido)-4-methyl-N-[2-oxo-8-(2-oxopyrrolidin-1-yl)-1-(thiophen-3-ylmethyl)-1,2,3,4-tetrahydroquinolin-3-yl]pentanamide (R)-(−)-mandelate (117 g) were added thereto, followed by stirring at room temperature for 10 minutes. The resultant mixture was partitioned, and the aqueous layer was extracted with ethyl acetate twice. The organic layers were combined, and the combined organic layer was washed with saturated aqueous sodium chloride solution, followed by drying over sodium sulfate. The solvent was evaporated under reduced pressure, and the thus-recovered residue was treated as described in Example 34(a), whereby the title compound (98.9 g) was yielded.

Comparative Example 1

(2R)-2-(2-Amino-2-methylpropanamido)-N-(1-benzyl-2-oxo-1,2,3,4-tetrahydroquinolin-3-yl)-4-methylpentanamide hydrochloride

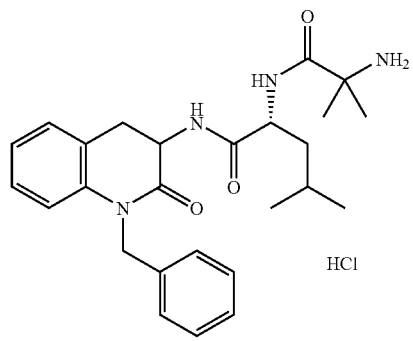

The procedures described in Example 4, Example 11(a), Example 12(a), and Example 16 were repeated, except that N-(2-oxo-1,2,3,4-tetrahydroquinolin-3-yl)acetamide obtainable by the procedure described in a publicly known literature [J. Chem. Soc., 1080 (1965)], was used, whereby the title compound was yielded.

MS(FAB)m/z451(M+H)$^+$ $^1$H-NMR(400 MHz, DMSO-d$_6$):

δ(ppm)0.88(3H, d, J=6.0 Hz), 0.91(3H, d, J=6.0 Hz), 1.45-1.75(9H, m), 2.97-3.10(2H, m), 4.53-4.68(2H, m), 5.12(1H, d, J=16.5 Hz), 5.23(1H, d, J=16.5 Hz), 6.97-7.04(2H, m), 7.15-7.35(7H, m), 8.24(3H, br s), 8.40(1H, d, J=8.5 Hz), 8.53(1H, d, J=7.5 Hz).

Test Example 1

Measurement of Agonistic Activity by Use of a Cell Line Satably Expressing Human GHS-R1a (Method of Experiment)

CHO-K1 cells were transfected with human GHS-R1a genes, to thereby provide cells stably expressing GHS-R1a (hGHS-R1a/CHO), and the agonistic activity of each compound was evaluated by use of the cells based on percent increase in intracellular calcium as an index.

The hGHS-R1a/CHO cells were inoculated at 6×10$^4$ cells/well in a 96-well plate (Clear bottom/Black plate, product of Corning), and cultured in Ham's F12 medium containing 10% fetal bovine serum at 37° C. and 5% CO$_2$ for 18 hours. After culture, the medium was removed, and then the hGHS-R1a/CHO cells were cultured for two hours in a Hanks' balanced salt solution/HEPES (HBSS/HEPES, 100 μL) containing a calcium fluorescent indicator (4 μM Fluo-3AM, product of Dojin), 2 mM Probenecid, 0.1% Pluronic F-127, and 0.1% BSA, whereby the indicator was incorporated into the cells. After washing the cells, HBSS/HEPES (175 μL/well) containing 2 mM Probenecid and 0.1% BSA was added to the plate, and the fluorescence before and after addition of each test compound was determined by means of FLEXstation (Ex: 485 nm, Em: 525 nm, product of Molecular Devices). Each test compound was multi-fold diluted with dimethyl sulfoxide and then diluted with HBSS/HEPES containing 2 mM Probenecid, 0.04% Pluronic F-127, and 0.1% BSA, to thereby attain a final concentration of interest. The thus-diluted solution (25 μL/well) was added to the wells.

The agonistic activity was calculated by the following formula, and the EC$_{50}$ (concentration of compound at which 50% agonistic activity is obtained) of each test compound was obtained from a dose-response curve.

Agonistic activity(%)=(A−B)/(C−D)×100

A: Fluorescence intensity after addition of test compound

B: Fluorescence intensity before addition of test compound

C: Fluorescence intensity after addition of 100 nM ghrelin

D: Fluorescence intensity before addition of ghrelin

As shown in Table 1, all the tested compounds fall within the scope of compound (1) of the present invention exhibit potent GHS-R agonistic activity. In particular, such potent GHS-R agonistic activities were 100-fold to 1.000-fold potent with respect to tetrahydroisoquinoline derivatives having no amino group at 8-position thereof.

TABLE 1

Agonistic activity on human GHS-R

| Compounds | GHS-R agonistic activity (EC$_{50}$: nM) |
|---|---|
| Example 34a | 0.38 |
| Example 34k | 0.47 |
| Example 34l | 0.37 |
| Example 35 | 0.9 |
| Example 36 | 1.1 |
| Example 34m | 1.5 |
| Example 37 | 1 |
| Example 34g | 2.75 |
| Example 25h | 6.13 |
| Example 25j | 4.13 |
| Example 34h | 0.74 |
| Example 34b | 0.052 |
| Example 25l | <0.1 |
| Example 38 | 0.1 |
| Example 34i | 0.2 |
| Example 34c | 0.02 |
| Example 34f | 1.13 |
| Example 34d | 0.22 |
| Example 34e | 0.07 |
| Example 47 | 18.2 |
| Example 40 | 80 |
| Example 41 | 11.3 |
| Example 39 | 12.9 |
| Example 66 | 0.45 |
| Human ghrelin | 0.70 |
| Anamorelin hydrochloride | 0.15 |
| Comp. Ex. 1 | 149 |

Test Example 2

Bioavailability (Method of Experiment)
A test compound was administered to male rats intravenously (1 or 3 mg/kg) or perorally (30 mg/kg), and to male beagles intravenously or perorally (3 mg/kg). After administration, blood was collected at designated times, to thereby obtain plasma samples. The plasma level of the test compound was determined using LC-MS/MS, from which bioavailability (BA) was calculated (n=3).
(Results)
Compound of Example 34a exhibited a BA of 35% (anamorelin hydrochloride: 21%) in rats, and a BA of 84% (anamorelin hydrochloride: 19%) in dogs. Thus, the compound showed higher bioavailability compared to anamorelin hydrochloride.

Test Example 3

Distribution in the Brain (Method of Experiment)
Under anesthesia, a test drug was intravenously administered to male rats (1 to 4 mg/kg) and then intravenously administered (14 to 95 μg/kg) at a constant rate. At two hours after starting the infusion, when a steady state was thought to have been reached, the whole blood was collected from each rat and the brain was excised. The concentrations of test drug in brain samples and plasma samples were determined using LC-MS/MS, and the brain-to-plasma partition coefficient (Kp value) was calculated (n=6 or 9).
(Results)
Compound of Example 34a exhibited an average (in terms of drug concentration) Kp of 0.06 (anamorelin hydrochloride: 0.42). Thus, the compound exhibited considerably reduced distribution in the brain compared to anamorelin hydrochloride, and the drug virtually provided no adverse side effects in the brain.

Test Example 4

CYP3A4 Inhibitory Activity (Method of Experiment)
The in vitro CYP3A4 inhibitory activity was determined by use of human liver microsomes based on the midazolam hydroxylation activity as an index, and the Ki values were calculated.
(Results)
Compound of Example 34a exhibited an average (in terms of drug concentration) Ki of 86 μmol/L (anamorelin hydrochloride: 3 μmol/L). Thus, the compound exhibited lower CYP3A4 inhibitory activity compared to anamorelin hydrochloride, and prevented drug interaction with the enzyme.

Test Example 5

Toxicity Test: Single Oral Administration to Dogs

An encapsulated test drug was forcedly administered to beagles, and acute toxicity of the drug was studied.
(Method)
Compound of Example 34a was singly perorally administered to male beagles at a dose of 30 and 100 mg/kg. Separately, anamorelin hydrochloride was singly perorally administered to male beagles at a dose of 3, 10, and 30 mg/kg. General conditions of the beagles were observed, and hematologic and blood biochemical tests were carried out.
(Results)
In the Example 34a compound-administered groups, only slight vomiting was observed at a maximum dose (100 mg/kg). However, in the anamorelin-hydrochloride-administered groups, serious anomalous disorders in general conditions such as vomiting, infrequent pulse, tremble, and disorders in walking were observed at a dose of 30 mg/kg.
Thus, Compound of Example 34a did not exhibit anomalous disorders which anamorelin hydrochloride exhibits, confirming high safety of the compound.

Test Example

Improvement of Cachexia Induced by IL-1β

(Method of Experiment)
By use of model rats with IL-1β-induced cachexia, the effects of a test compound on ameliorating reduction in body weight and in food intake were examined.
SD rats (male, 8-week old, 270 to 340 g, Japan Charles River) were conditioned in a cage (one rat/cage), and were allowed water and a diet (CRF-1, product of Oriental Yeast Co., Ltd.) ad libitum. The illumination conditions employed in the house were as follows: 10:30 to 22:30 (dark) and 22:30 to 10:30 (light).
An osmotic pump (Mini-Osmotic Pump Model 2001, product of ALZET, filled with saline) was connected to a canula, and the canula was inserted into the cerebral ventricle of a rat. The rats obtained were conditioned for three days, and the osmotic pump was changed to another osmotic pump filled with recombinant mouse IL-1β (rmIL-1β). By means of the pump, rmIL-1β was continuously injected into the cerebral ventricle (5 μg/μL/hr), to thereby induce cachexia. Two days after starting of injection of IL-1β, a test compound dissolved in 0.5% methylcellulose solution was perorally administered to each rat just before switching-off the light. During the period of administration of the test compound, the body weight and the food intake were measured every 24 hours.

(Results)

Compound of Example 34a significantly suppressed reduction in body weight and in food intake, which would otherwise be caused by IL-1β, at a dose of 100 mg/kg, thereby ameliorating IL-1β-induced cachexia.

(Drug Preparation Example)

According to the Japanese Pharmacopoeia, compound of Example 34a (powder) (8 g), lactose (19.8 g), crystalline cellulose (6 g), hydroxypropyl cellulose (2 g), and crospovidone (4 g) were mixed, and the mixture was granulated by use of purified water as a granulation liquid. The granules obtained were dried to give a granular powder. Magnesium stearate (0.2 g) was added to the powder, to thereby prepare a powder for tablets. The powder was pelletized at an appropriate load, to thereby prepare tablets each containing 40 mg of compound of Example 34a (diameter: 8 mm, 200 mg/tablet).

The invention claimed is:

1. A 3,8-diaminotetrahydroquinoline derivative represented by formula (1a):

(1a)

wherein X represents $CH_2$, C=O, CH—OR, CH—SR, or CH—NRR';

m is a number of 1 or 2;

Ar represents a phenyl group, a naphthyl group, a 5-membered or 6-membered aromatic heterocyclic group having one or two elements selected from S, N, and O, or a condensed aromatic heterocyclic group formed between a benzene ring and a 5-membered or 6-membered heterocyclic ring having one or two elements selected from S, N, and O, wherein the phenyl, naphthyl, or aromatic heterocyclic groups may be substituted by 1 to 3 halogen atoms, a C1 to C6 alkyl group, or a C1 to C6 alkoxy group;

$R^1$ and $R^2$, which may be identical to or different from each other, each represent a hydrogen atom or a methyl group;

$R^3$ represents a C1 to C6 alkyl group, the alkyl group optionally being substituted by a methylthio or benzyloxy group, a phenyl group, a phenyl-$C_{1-4}$ alkyl group, or an indolyl-$C_{1-4}$ alkyl group, the phenyl group or the indolyl group optionally being substituted by a C1 to C6 alkyl group, a halogen atom, a hydroxyl group, or a C1 to C6 alkoxy group;

n is a number of 0 or 1;

$R^4$ and $R^5$, which may be identical to or different from each other, each represent a hydrogen atom, or a C1 to C6 linear, branched, or cyclic alkyl group, the alkyl group optionally being substituted by a halogen atom, a hydroxyl group, a C1 to C6 alkoxy group, a phenyl group, a benzyloxy group, or a hydroxyphenyl group, or $R^4$ or $R^5$, and $R^6$ or $R^7$ may be linked to the adjacent nitrogen atom to form a pyrrolidine ring or a piperidine ring, the pyrrolidine ring or the piperidine ring optionally being substituted by a hydroxyl group;

$R^6$ and $R^7$, which may be identical to or different from each other, each represent a hydrogen atom or a C1 to C6 alkyl group; and R and R', which may be identical to or different from each other, each represent a hydrogen atom or a C1 to C6 linear, branched, or cyclic alkyl group, or a salt thereof.

2. The compound or salt according to claim 1, wherein m is 1.

3. The compound or salt according to claim 1, wherein Ar is a phenyl group, a naphthyl group, a pyridyl group, a quinolyl group, an isoquinolyl group, a thienyl group, a furyl group, a pyrrolyl group, a benzothienyl group, a benzofuryl group, an indolyl group, a thiazolyl group, a pyrimidinyl group, a quinazolynyl group, an imidazolyl group, a benzimidazolyl group, or a benzothiazolyl group, wherein these rings may be substituted by 1 to 3 halogen atoms, a C1 to C6 alkyl group, or a C1 to C6 alkoxy group.

4. The compound or salt according to claim 1, wherein Ar is a phenyl group, a pyridyl group, a thienyl group, or a furyl group.

5. The compound or salt according to claim 1, wherein $R^3$ is a C1 to C6 alkyl group, a benzyl group, or an indolylmethyl group, the indolyl group optionally being substituted at the nitrogen atom thereof by a C1 to C6 alkyl group.

6. The compound or salt according to claim 1, wherein n is 0.

7. The compound or salt according to claim 1, wherein each of $R^4$ and $R^5$, which are identical to or different from each other, is a hydrogen atom, or a C1 to C4 linear, branched, or cyclic alkyl group.

8. The compound or salt according to claim 1, wherein each of $R^6$ and $R^7$ is a hydrogen atom.

9. The compound or salt according to claim 1, wherein $R^3$ is a C4 alkyl group.

10. The compound or salt according to claim 1, wherein each of $R^4$ and $R^5$, which are identical to or different from each other, is a hydrogen atom, a methyl group, or an ethyl group, or $R^4$ and $R^5$ are linked together to form a cyclobutyl group.

11. A drug containing a compound or salt as recited in claim 1.

12. A pharmaceutical composition comprising a compound or salt as recited in claim 1, and a pharmaceutically acceptable carrier.

* * * * *